United States Patent
Woods et al.

(10) Patent No.: US 8,716,297 B2
(45) Date of Patent: May 6, 2014

(54) CHEMICAL ENTITIES TO BE USED FOR WEE1 INHIBITION FOR THE TREATMENT OF CANCER

(75) Inventors: Keith W. Woods, Libertyville, IL (US); Chunqui Lai, Libertyville, IL (US); Thomas D. Penning, Elmhurst, IL (US); Julie M. Miyashiro, Morton Grove, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/547,314

(22) Filed: Jul. 12, 2012

(65) Prior Publication Data

US 2013/0018045 A1 Jan. 17, 2013

Related U.S. Application Data

(60) Provisional application No. 61/508,157, filed on Jul. 15, 2011.

(51) Int. Cl.
*A61K 31/522* (2006.01)
*C07D 239/70* (2006.01)

(52) U.S. Cl.
USPC ........................ 514/260.1; 544/255

(58) Field of Classification Search
USPC ............... 544/33, 250; 514/226.5, 267
See application file for complete search history.

(56) References Cited

FOREIGN PATENT DOCUMENTS

| WO | WO9828281 A1 | 7/1998 |
|---|---|---|
| WO | WO2005023807 A2 | 3/2005 |
| WO | WO2009151997 A1 | 12/2009 |
| WO | WO2010078421 A1 | 7/2010 |

OTHER PUBLICATIONS

Golub, 1999, Science, vol. 286, pp. 531-537.*
Targeted Cancer Therapies, http://www.cancer.gov/cancertopics/factsheet/therapy/targeted, accessed Jan. 12, 2011.*
De Witt Hamer, 2011, Clin Cancer Res, vol. 17, pp. 4200-4207.*
International Search Report and Written Opinion for Application No. PCT/US2012/046482, mailed on Oct. 15, 2012, 9 pages.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Glotzer M., et al., "Cyclin is Degraded by the Ubiquitin Pathway," Nature, 1991, vol. 349 (6305), pp. 132-138.
Hashimoto O., et al., "Cell cycle Regulation by the Wee1 Inhibitor PD0166285, Pyrido [2,3-d] Pyimidine, in the B16 Mouse Melanoma Cell Line," Bio Medical Center Cancer, 2006, vol. 6, pp. 292.
Hirai H., et al., "Small-molecule Inhibition of Wee1 Kinase by MK-1775 Selectively Sensitizes p53-deficient Tumor Cells to DNA-damaging Agents," Molecular Cancer Therapeutics, 2009, vol. 8 (11), pp. 2992-3000.
Leijen S., et al., "Abrogation of the G2 Checkpoint by Inhibition of Wee-1 Kinase Results in Sensitization of p53-deficient Tumor Cells to DNA-damaging Agents," Current Clinical Pharmacology, 2010, vol. 5 (3), pp. 186-191.
Lindqvist A., et al., "The Decision to Enter Mitosis: Feedback and Redundancy in the Mitotic Entry Network," Journal of Cell Biology, 2009, vol. 185 (2), pp. 193-202.
McGowan C.H., et al., "Human Wee1 Kinase Inhibits Cell Division by Phosphorylating p34cdc2 Exclusively on Tyr15," The EMBO Journal, 1993, vol. 12 (1), pp. 75-85.
Nurse P., "Universal Control Mechanism Regulating Onset of M-Phase," Nature, 1990, vol. 344 (6266), pp. 503-508.
O'Connell M.J., et al., "Chk1 is a Wee1 Kinase in the G2 DNA Damage Checkpoint Inhibiting Cdc2 by Y15 Phosphorylation," The EMBO Journal, 1997, vol. 16 (3), pp. 545-554.
Parker L.L., et al., "Inactivation of the p34cdc2-Cyclin B Complex by the Human WEE1 Tyrosine Kinase," Science, 1992, vol. 257 (5078), pp. 1955-1957.
Sabin E.A., et al., "High-Level Expression and in Vivo Processing of Chimeric Ubiquitin Fusion Proteins in *Saccharomyces cerevisiae*," Nature Biotechnology, 1989, vol. 7 (7), pp. 705-709.
Sancar A., et al., "Molecular Mechanisms of Mammalian DNA Repair and the DNA Damage Checkpoints," Annual Review of Biochemistry, 2004, vol. 73, pp. 39-85.
Stumpff J., et al., "*Drosophila* Wee1 Kinase Regulates Cdk1 and Mitotic Entry during Embryogenesis," Current Biology, 2004, vol. 14 (23), pp. 2143-2148.
Sutton, V.R. et al., "Bcl-2 Prevents Apoptosis Induced by Perforin and Granzyme B, but not That Mediated by Whole Cytotoxic Lymphocytes," Journal of Immunology, 1997, vol. 158 (12), pp. 5783-5790.
Wang Y., et al., "Knockdown of Chk1, Wee1 and Myt1 by RNA Interference Abrogates G2 Checkpoint and Induces Apoptosis," Cancer Biology & Therapy, 2004, vol. 3 (3), pp. 305-313.

* cited by examiner

*Primary Examiner* — Rebecca Anderson
*Assistant Examiner* — Karen Cheng
(74) *Attorney, Agent, or Firm* — Lisa V. Mueller; Michael Best & Friedrich LLP

(57) ABSTRACT

The present invention relates to compounds of formula (I) or pharmaceutical acceptable salts,

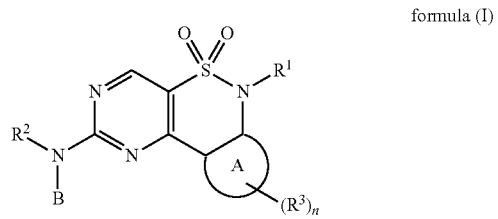

formula (I)

wherein $R^1$, $R^2$, $R^3$, A, B, and n are defined in the description. The present invention relates also to compositions containing compounds of formula (I) which are useful for inhibiting kinases such as wee-1 and methods of treating diseases such as cancer.

19 Claims, No Drawings

CHEMICAL ENTITIES TO BE USED FOR WEE1 INHIBITION FOR THE TREATMENT OF CANCER

CROSS-REFERENCE TO RELATED APPLICATIONS

This application claims priority to U.S. Provisional Application Ser. No. 61/508,157 filed Jul. 15, 2011, which is incorporated by reference in its entirety.

FIELD OF THE INVENTION

This invention pertains to compounds which inhibit the activity of Wee-1 kinase, methods of making the compounds, compositions containing the compounds, and methods of treatment using the compounds.

BACKGROUND OF THE INVENTION

In order to undergo proper cell division, eukaryotic cells must faithfully replicate their genome and then correctly segregate their chromosomes into two daughter cells. This process of cell division, also called the cell cycle, is a step-wise process that is governed by checkpoints to ensure genomic integrity. Upon completion of DNA replication (S-phase), cells enter a growth phase (G2-phase) prior to proceeding into mitosis for chromosome segregation (M-phase). A key regulator of mitosis is the kinase Cdk1 (as called Cdc2) (Nurse, P. (1990) Universal control mechanism regulating onset of M-phase. Nature 344, 503-508). Activation of Cdk1 results in the onset of mitosis, and its subsequent inactivation initiates the exit from mitosis. Cdk1 is activated by the binding of Cyclin A or Cyclin B. Both Cyclin A-Cdk1 and Cyclin B-Cdk1 complexes function to initiate mitosis (Lindqvist, A., et. Al. (2009) The decision to enter mitosis: feedback and redundancy in the mitotic entry network. The Journal of cell biology 185, 193-202). The degradation of Cyclin B triggers the inactivation of Cdk1, resulting in the mitotic exit and entry into a growth (G1) phase prior to beginning a new round of the cell cycle (Glotzer, M., et al. (1991) Cyclin is degraded by the ubiquitin pathway. Nature 349, 132-138).

In addition to Cyclins, Cdk1 is also regulated by Wee1, an atypical tyrosine kinase that phosphorylates Cdk1 on tyrosine 15 (Y15) and inactivates Cdk1 (McGowan, C. H., et al. (1993) Human Wee1 kinase inhibits cell division by phosphorylating p34cdc2 exclusively on Tyr15. The EMBO journal 12, 75-85; Parker, L. L., et al. (1992) Inactivation of the p34cdc2-cyclin B complex by the human WEE1 tyrosine kinase. Science 257, 1955-1957). Wee1 is a critical negative regulator of Cdk1 and functions at the G2-M phase checkpoint to ensure that DNA replication has been completed and the genome is not damaged prior to entering mitosis (O'Connell, et al. (1997) Chk1 is a wee1 kinase in the G2 DNA damage checkpoint inhibiting cdc2 by Y15 phosphorylation. The EMBO journal 16, 545-554). Loss of Wee1 can result in premature entry into mitosis, resulting in mitotic catastrophe and cell death (Stumpff, J., et al. (2004) Drosophila Wee1 kinase regulates Cdk1 and mitotic entry during embryogenesis. Curr Biol 14, 2143-2148). Furthermore, many cancers are defective in their G1-phase checkpoints and are reliant on G2-M phase checkpoints (Sancar, A., et al. (2004) Molecular mechanisms of mammalian DNA repair and the DNA damage checkpoints. Annual review of biochemistry 73, 39-85). Indeed, loss of expression of Wee1 has been shown to lead to the abrogation of the G2-M phase checkpoint and sensitize tumor cells to DNA damage, especially tumors that have lost their G1-phase checkpoint due to a deficiency in the p53 protein (Wang, Y., et al. (2004) Knockdown of Chk1, Wee1 and Myt1 by RNA interference abrogates G2 checkpoint and induces apoptosis. Cancer biology & therapy 3, 305-313).

Inhibitors of Wee1 have the potential to selectively cause lethality in cancerous cells that are defective in other cell cycle checkpoints, while sparing normal tissues that can activate other cell cycle checkpoints. Thus, small molecule inhibitors of Wee1 would be beneficial for therapeutic intervention in cancer and other cell proliferative disorders.

SUMMARY OF THE INVENTION

The present invention has numerous embodiments. One embodiment of this invention, therefore, pertains to compounds that have formula (I)

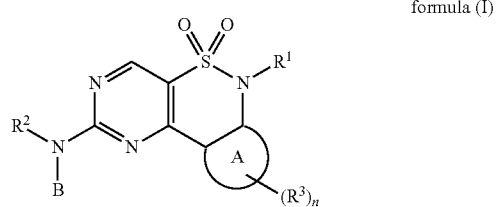

formula (I)

wherein A, B, $R^1$, $R^2$, $R^3$, and n are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2, 4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of formula (I):

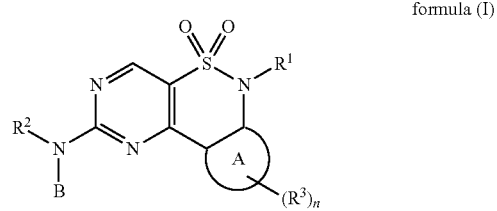

formula (I)

wherein

A is aryl or heteroaryl;

B is (a) $C_{3-8}$ cyloalkyl, phenyl, naphthyl, tetrahydronaphthyl, indenyl, or indanyl, wherein the $C_{3-8}$ cyloalkyl, phenyl, naphthyl, tetrahydronaphthyl, indenyl, or indanyl are optionally substituted with one or more $R^4$; or (b) 5-16 membered monocyclic, bicyclic, or tricyclic heterocyclyl, wherein the heterocyclyl is optionally substituted with one or more $R^5$;

$R^1$ is H, $C_{1-8}$-alkyl, $C_{2-8}$-alkenyl, $C_{2-8}$-alkynyl, $C_{3-8}$-cycloalkyl, aryl, heteroaryl, aryl-$C_{1-6}$-alkyl-, $C_{3-8}$ cycloalkyl-$C_{1-6}$-alkyl-, or heteroaryl-$C_{1-6}$-alkyl-; wherein the $C_{1-8}$-alkyl, $C_{2-8}$-alkenyl, $C_{2-8}$-alkynyl, alone or as part of another moiety, are optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$; and (b) the $C_{3-8}$-cycloalkyl, aryl, and heteroaryl, are optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$;

$R^2$ is H or $C_{1-6}$-alkyl;

$R^3$ is CN, $NO_2$, halo, $C_{1-6}$-alkyl, $C_{1-6}$-haloalkyl, $C_{1-6}$-hydroxyalkyl, $C_{1-6}$-aminoalkyl, $N(C_{1-6}$-alkyl$)_2$-$C_{1-6}$-alkyl, $C_{3-7}$ cycloalkyl, aryl, heteroaryl, heterocycloalkyl, —$OR^6$, —$C(O)R^6$, —$C(O)OR^6$, —$OC(O)R^6$, —$SR^6$, —$S(O)R^6$, —$SO_2R^6$, —$NR^7R^8$, —$NHC(O)R^6$, —$NHC(O)NHR^7$, —$NHC(O)OR^6$, —$NHSO_2R^6$, —$C(O)NR^7R^8$, or —$SO_2NHR^7R^8$, wherein the $R^3C_{3-7}$ cycloalkyl, aryl, heteroaryl, heterocycloalkyl are optionally substituted with one or more $R^9$;

$R^4$ is CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-; wherein the aryl, cycloalkyl, heteroaryl, or heterocycloalkyl, alone or as part of another moiety, are optionally substituted with one or more $R^{10}$;

$R^5$ is CN, $NO_2$, halo, $C_{1-6}$-alkyl, $C_{1-6}$-haloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$;

$R^6$ is hydrogen, $C_{1-6}$-alkyl, aryl, $C_{3-8}$ cycloalkyl, aryl, heteroaryl, or heterocycloalkyl, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^7$ is hydrogen, $C_{1-6}$-alkyl, aryl, $C_{3-8}$ cycloalkyl, aryl, heteroaryl, or heterocycloalkyl, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, aryl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^8$ is hydrogen or $C_{1-6}$-alkyl;

$R^9$ is CN, $NO_2$, halo, $C_{1-6}$-alkyl, $C_{1-6}$-haloalkyl, $OR_m$, $SR^m$, $C(O)R^m$, $C(O)NR^nR^o$, $C(O)OR^m$, $NR^nR^o$, $NR^nC(O)R^m$, $S(O)_2R^m$, $NR^nS(O)_2R^m$, or $S(O)_2NR^mR^o$;

$R^{10}$ is CN, $NO_2$, halo, $C_{1-6}$-alkyl, $C_{1-6}$-haloalkyl, $OR^p$, $SR^p$, $C(O)R^p$, $C(O)NR^qR^r$, $C(O)OR^p$, $NR^qR^r$, $NR^qC(O)R^p$, $S(O)_2R^p$, $NR^qS(O)_2R^p$, or $S(O)_2NR^qR^r$;

$R^a$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$, at each occurrence, are independently selected from the group consisting of H, $C_{1-6}$ alkyl, $C_{1-6}$ haloalkyl, aryl, $C_{3-8}$ cycloalkyl, heteroaryl, heterocycloalkyl;

$R^d$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^g$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^j$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^k$ and $R^l$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^m$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^n$ and $R^o$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^p$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^q$ and $R^r$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

n is 0, 1 or 2;

or a pharmaceutically acceptable salt or solvate thereof.

In one embodiment of formula (I), A is 5-8 membered aryl or heteroaryl. In yet another embodiment of formula (I), A is phenyl, pyridyl, pyrazyl, pyrimidinyl, pyridazinyl, furanyl, thiophenyl, or pyrazolyl.

In one embodiment of formula (I), A is phenyl and n is 0, 1, or 2. In another embodiment of formula (I), A is unsubstituted. In another embodiment of formula (I), n is 1.

In one embodiment of formula (I), A is

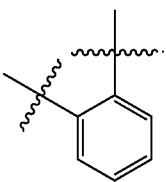 [SMILES: *c1ccccc1*]

In one embodiment of formula (I), A is

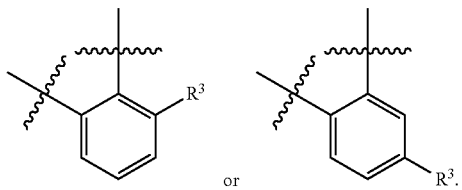

In another embodiment, $R^3$ is halo, —$OR^6$, —$C(O)OR^6$, —$C(O)NR^7R^8$, or —$NR^7R^8$. In another embodiment, $R^3$ is aryl or heteroaryl, wherein the aryl or heteroaryl is optionally substituted with one or more $R^9$, and $R^9$ is halo, $C_{1-6}$-alkyl, $C_{1-6}$-haloalkyl, $OR^m$, $C(O)R^m$, $C(O)NR''R^o$, $C(O)OR^m$, $NR''R^o$, or $NR''C(O)R^m$, and n is 1.

In one embodiment of formula (I), A is pyridyl and n is 0, 1, or 2. In another embodiment, the pyridyl ring is unsubstituted. In yet another embodiment, n is 1.

In one embodiment of formula (I), A is

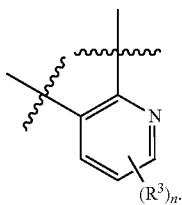

In yet another embodiment, n is 0.

In one embodiment of formula (I), A is thiophenyl and n is 0, 1, or 2. In another embodiment, the thiophenyl ring is unsubstituted. In yet another embodiment, n is 1.

In one embodiment of formula (I), A is

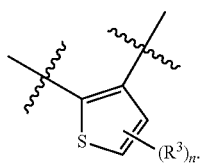

In yet another embodiment, n is 0.

In one embodiment of formula (I), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In another embodiment of formula (I), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (I), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH$=$CH_2$, $CH_2CH$=$CHCH_3$, or —$CH_2CH_2CH$=$CH_2$.

In one embodiment of formula (I), $R^1$ is aryl or aryl-$C_{1-6}$-alkyl, wherein the aryl, alone or as part of another moiety, is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$. In another embodiment, $R^1$ is phenyl or phenyl-$C_{1-6}$-alkyl, wherein the phenyl is optionally substituted with one, two or three $C_{1-6}$-alkyl, $C_{1-6}$-haloalkyl, or halogen.

In one embodiment of formula (I), $R^2$ is H.

In one embodiment of formula (I), B is $C_{3-8}$ cyloalkyl, wherein the $C_{3-8}$ cyloalkyl is unsubstituted. In another embodiment of formula (I), B is $C_{3-8}$ cyloalkyl, wherein $C_{3-8}$ cyloalkyl is substituted with one, two, or three substituents selected from the group consisting of halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^bS(O)_2R^g$, and $S(O)_2NR^hR^i$.

In another embodiment of formula (I), B is naphthyl, tetrahydronaphthyl, indenyl, or indanyl, wherein the naphthyl, tetrahydronaphthyl, indenyl, or indanyl is unsubstituted. In yet another embodiment of formula (I), B is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In one embodiment of formula (I), B is phenyl. In another embodiment of formula (I), B is phenyl, wherein the phenyl is unsubstituted. In another embodiment of formula (I), B is phenyl, wherein the phenyl is substituted with one, two, or three $R^4$, and $R^4$ is halo, $C_{1-6}$-alkyl, $C_{1-6}$ haloalkyl, $OR^g$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (I), $R^{10}$ is $C_{1-6}$-alkyl, $C_{1-6}$ haloalkyl, or $C(O)R^p$; $R^g$ is optionally substituted $C_{1-6}$ alkyl, $C_{1-6}$ haloalkyl, $C_{3-8}$ cycloalkyl; and $R^p$ is $C_{1-6}$ alkyl, $C_{1-6}$ haloalkyl, or $C_{3-8}$ cycloalkyl.

In one embodiment of formula (I), B is phenyl, wherein the phenyl is substituted with heterocycloalkyl and optionally one or two $R^4$, wherein $R^4$ is halo, $C_{1-6}$-alkyl, $C_{1-6}$ haloalkyl, or $OR^g$, wherein the heterocycloalkyl is optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (I), B is

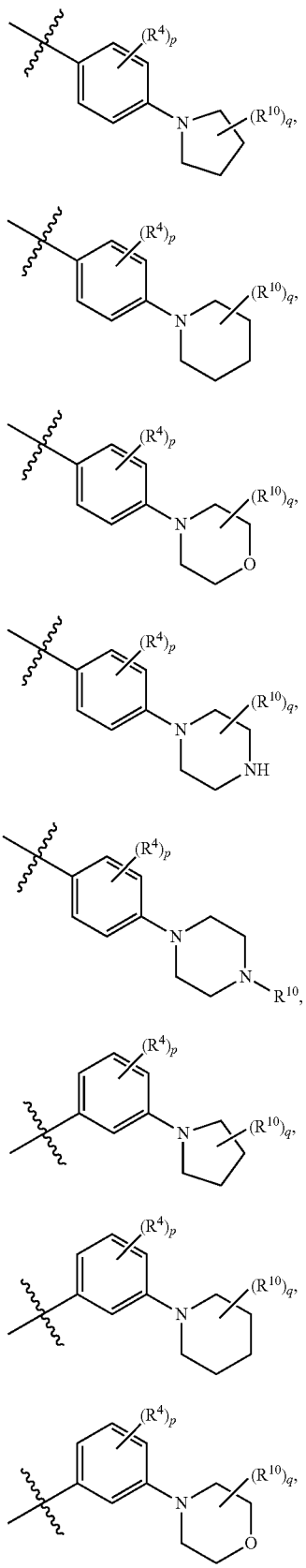

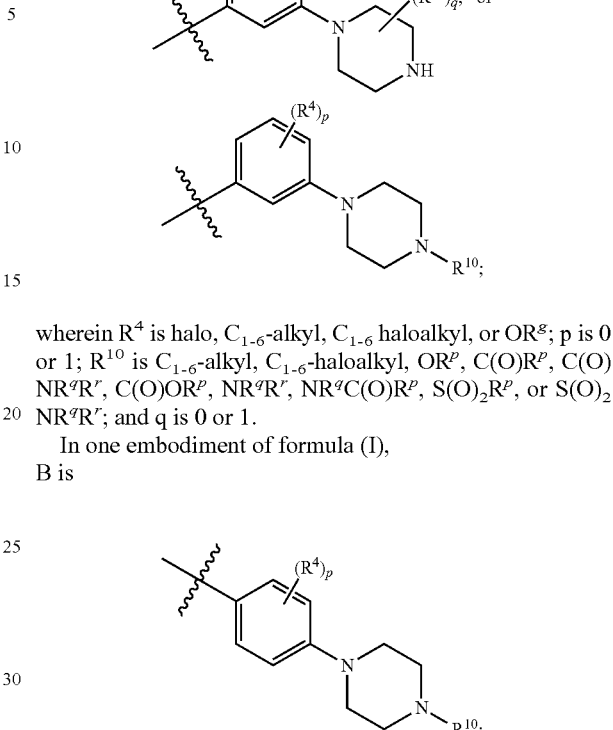

wherein $R^4$ is halo, $C_{1-6}$-alkyl, $C_{1-6}$ haloalkyl, or $OR^g$; p is 0 or 1; $R^{10}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and q is 0 or 1.

In one embodiment of formula (I),
B is

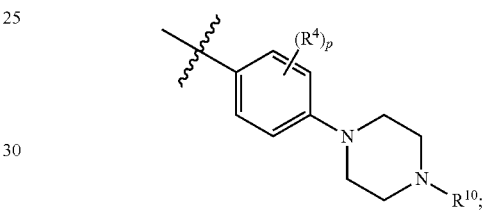

$R^4$ is halo, $C_{1-6}$-alkyl, $C_{1-6}$ haloalkyl, or $OR^g$; $R^{10}$ is $C_{1-6}$-alkyl and p is 0 or 1.

In one embodiment of formula (I), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (I), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (I), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment of formula (I), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (I), B is unsubstituted. In another embodiment of formula (I), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment of formula (I), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (I), B is unsubstituted. In another embodiment of formula (I), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

Specific embodiments contemplated as part of the invention include, but are not limited to, compounds of formula (I), for example:

6-allyl-N-[4-(4-methylpiperazin-1-yl)phenyl]-6H-pyrimido[5,4-c][2,1]benzothiazin-2-amine 5,5-dioxide,
N-[4-(4-methylpiperazin-1-yl)phenyl]-6-[(1E)-prop-1-en-1-yl]-6H-pyrimido[5,4-c][2,1]benzothiazin-2-amine 5,5-dioxide,
6-allyl-N-{4-[2-(diethylamino)ethoxy]phenyl}-6H-pyrimido[5,4-c][2,1]benzothiazin-2-amine 5,5-dioxide,
6-allyl-N-cyclohexyl-6H-pyrimido[5,4-c][2,1]benzothiazin-2-amine 5,5-dioxide,
1-{6-[(6-allyl-5,5-dioxido-6H-pyrimido[5,4-c][2,1]benzothiazin-2-yl)amino]-2,3-dihydro-1H-indol-1-yl}ethanone,
6-[(6-allyl-5,5-dioxido-6H-pyrimido[5,4-c][2,1]benzothiazin-2-yl)amino]-2H-1,4-benzoxazin-3(4H)-one,
6-allyl-N-[4-(pyridin-4-yl)phenyl]-6H-pyrimido[5,4-c][2,1]benzothiazin-2-amine 5,5-dioxide,
6-allyl-N-(1-methyl-1,2,3,4-tetrahydroquinolin-7-yl)-6H-pyrimido[5,4-c][2,1]benzothiazin-2-amine 5,5-dioxide,
6-allyl-N-[4-(4-methylpiperidin-1-yl)phenyl]-6H-pyrimido[5,4-c][2,1]benzothiazin-2-amine 5,5-dioxide,
1-(4-{4-[(6-allyl-5,5-dioxido-6H-pyrimido[5,4-c][2,1]benzothiazin-2-yl)amino]phenyl}piperazin-1-yl)ethanone,
6-allyl-N-[4-(piperidin-1-yl)phenyl]-6H-pyrimido[5,4-c][2,1]benzothiazin-2-amine 5,5-dioxide,
6-allyl-N-[2-(4-methylpiperazin-1-yl)phenyl]-6H-pyrimido[5,4-c][2,1]benzothiazin-2-amine 5,5-dioxide,
6-allyl-N-(4-cyclohexylphenyl)-6H-pyrimido[5,4-c][2,1]benzothiazin-2-amine 5,5-dioxide,
6-allyl-N-[4-(1H-imidazo[4,5-c]pyridin-2-yl)phenyl]-6H-pyrimido[5,4-c][2,1]benzothiazin-2-amine 5,5-dioxide,
6-allyl-N-[2-methoxy-4-(4-methylpiperazin-1-yl)phenyl]-6H-pyrimido[5,4-c][2,1]benzothiazin-2-amine 5,5-dioxide,
6-allyl-N-[4-(morpholin-4-yl)phenyl]-6H-pyrimido[5,4-c][2,1]benzothiazin-2-amine 5,5-dioxide,
6-allyl-N-(5,6,7,8-tetrahydronaphthalen-2-yl)-6H-pyrimido[5,4-c][2,1]benzothiazin-2-amine 5,5-dioxide,
6-allyl-N-[3-(4-methylpiperazin-1-yl)phenyl]-6H-pyrimido[5,4-c][2,1]benzothiazin-2-amine 5,5-dioxide,
6-allyl-N-[4-(1-methylpiperidin-4-yl)phenyl]-6H-pyrimido[5,4-c][2,1]benzothiazin-2-amine 5,5-dioxide,
6-allyl-N-[4-(1H-benzimidazol-2-yl)phenyl]-6H-pyrimido[5,4-c][2,1]benzothiazin-2-amine 5,5-dioxide,
6-allyl-N-[4-(1-methyl-1H-benzimidazol-2-yl)phenyl]-6H-pyrimido[5,4-c][2,1]benzothiazin-2-amine 5,5-dioxide,
6-allyl-N-(2,4,4-trimethyl-1,2,3,4-tetrahydroisoquinolin-7-yl)-6H-pyrimido[5,4-c][2,1]benzothiazin-2-amine 5,5-dioxide,
6-allyl-N-[4-(pyrimidin-2-yl)phenyl]-6H-pyrimido[5,4-c][2,1]benzothiazin-2-amine 5,5-dioxide,
6-allyl-N-phenyl-6H-pyrimido[5,4-c][2,1]benzothiazin-2-amine 5,5-dioxide,
6-allyl-N-[4-(piperazin-1-yl)phenyl]-6H-pyrimido[5,4-c][2,1]benzothiazin-2-amine 5,5-dioxide,
6-allyl-N-(1,2,3,4-tetrahydroisoquinolin-7-yl)-6H-pyrimido[5,4-c][2,1]benzothiazin-2-amine 5,5-dioxide,
6-allyl-N-(pyridin-4-yl)-6H-pyrimido[5,4-c][2,1]benzothiazin-2-amine 5,5-dioxide,
6-allyl-N-(2'-methyl-2',3'-dihydro-1'H-spiro[cyclopropane-1,4'-isoquinolin]-7'-yl)-6H-pyrimido[5,4-c][2,1]benzothiazin-2-amine 5,5-dioxide,
6-allyl-6H-pyrimido[5,4-c][2,1]benzothiazin-2-amine 5,5-dioxide,
6-allyl-N-(1,2,3,4-tetrahydroquinolin-7-yl)-6H-pyrimido[5,4-c][2,1]benzothiazin-2-amine 5,5-dioxide,
6-allyl-N-[3-fluoro-4-(piperazin-1-yl)phenyl]-6H-pyrimido[5,4-c][2,1]benzothiazin-2-amine 5,5-dioxide,
6-allyl-N-phenyl-6H-pyrido[2,3-c]pyrimido[4,5-e][1,2]thiazin-2-amine 5,5-dioxide,
6-allyl-N-(1,2,3,4-tetrahydroisoquinolin-7-yl)-6H-pyrido[2,3-c]pyrimido[4,5-e][1,2]thiazin-2-amine 5,5-dioxide,
6-allyl-N-[4-(piperazin-1-yl)phenyl]-6H-pyrido[2,3-c]pyrimido[4,5-e][1,2]thiazin-2-amine 5,5-dioxide,
1-{6-[(6-allyl-5,5-dioxido-6H-pyrido[2,3-c]pyrimido[4,5-e][1,2]thiazin-2-yl)amino]-2,3-dihydro-1H-indol-1-yl}ethanone,
6-allyl-N-[3-fluoro-4-(piperazin-1-yl)phenyl]-6H-pyrido[2,3-c]pyrimido[4,5-e][1,2]thiazin-2-amine 5,5-dioxide,
6-allyl-N-[4-(piperidin-4-yl)phenyl]-6H-pyrido[2,3-c]pyrimido[4,5-e][1,2]thiazin-2-amine 5,5-dioxide,
6-allyl-N-(1,2,3,4-tetrahydroquinolin-7-yl)-6H-pyrido[2,3-c]pyrimido[4,5-e][1,2]thiazin-2-amine 5,5-dioxide,
6-allyl-N-{4-[2-(diethylamino)ethoxy]phenyl}-6H-pyrido[2,3-c]pyrimido[4,5-e][1,2]thiazin-2-amine 5,5-dioxide,
6-allyl-N-[4-(4-methylpiperazin-1-yl)phenyl]-6H-pyrido[2,3-c]pyrimido[4,5-e][1,2]thiazin-2-amine 5,5-dioxide,
6-allyl-N-[3-chloro-4-(4-methylpiperazin-1-yl)phenyl]-6H-pyrido[2,3-c]pyrimido[4,5-e][1,2]thiazin-2-amine 5,5-dioxide,
6-allyl-N-[3-methyl-4-(piperazin-1-yl)phenyl]-6H-pyrido[2,3-c]pyrimido[4,5-e][1,2]thiazin-2-amine 5,5-dioxide,
{4-[(6-allyl-5,5-dioxido-6H-pyrido[2,3-c]pyrimido[4,5-e][1,2]thiazin-2-yl)amino]phenyl}(4-methylpiperazin-1-yl)methanone,
6-allyl-N-[2-methyl-4-(4-methylpiperazin-1-yl)phenyl]-6H-pyrido[2,3-c]pyrimido[4,5-e][1,2]thiazin-2-amine 5,5-dioxide,
6-allyl-N-[4-(pyrrolidin-3-yl)phenyl]-6H-pyrido[2,3-c]pyrimido[4,5-e][1,2]thiazin-2-amine 5,5-dioxide,
6-allyl-N-(1,2,3,4-tetrahydroisoquinolin-6-yl)-6H-pyrido[2,3-c]pyrimido[4,5-e][1,2]thiazin-2-amine 5,5-dioxide,
6-allyl-N-(2'-methyl-2',3'-dihydro-1'H-spiro[cyclopropane-1,4'-isoquinolin]-7'-yl)-6H-pyrido[2,3-c]pyrimido[4,5-e][1,2]thiazin-2-amine 5,5-dioxide,
6-allyl-N-[4-(hexahydropyrrolo[1,2-a]pyrazin-2(1H)-yl)phenyl]-6H-pyrido[2,3-c]pyrimido[4,5-e][1,2]thiazin-2-amine 5,5-dioxide,
6-allyl-N-(1-methyl-1,2,3,4-tetrahydroquinolin-7-yl)-6H-pyrido[2,3-c]pyrimido[4,5-e][1,2]thiazin-2-amine 5,5-dioxide, 6-allyl-N-[3-methyl-4-(4-methylpiperazin-1-yl)phenyl]-6H-pyrido[2,3-c]pyrimido[4,5-e][1,2]thiazin-2-amine 5,5-dioxide, 6-allyl-N-[4-(piperazin-1-yl)-3-(trifluoromethyl)phenyl]-6H-pyrido[2,3-c]pyrimido[4,5-e][1,2]thiazin-2-amine 5,5-dioxide, 6-allyl-N-[4-(morpholin-4-yl)phenyl]-6H-pyrido[2,3-c]pyrimido[4,5-e][1,2]thiazin-2-amine 5,5-dioxide, 6-allyl-N-[3-methyl-4-(4-methyl-1,4-diazepan-1-yl)phenyl]-6H-pyrido[2,3-c]pyrimido[4,5-e][1,2]thiazin-2-amine 5,5-dioxide, 6-allyl-N-(2',3'-dihydro-1'H-spiro[cyclopropane-1,4'-isoquinolin]-7'-yl)-6H-pyrido[2,3-c]pyrimido[4,5-e][1,2]thiazin-2-amine 5,5-dioxide, 6-methyl-N-[4-(4-methylpiperazin-1-yl)phenyl]-6H-pyrimido[4,5-e]thieno[3,2-c][1,2]thiazin-2-amine 5,5-dioxide, 6-methyl-N-[4-(4-methylpiperazin-1-yl)phenyl]-6H-pyrimido[5,4-c][2,1]benzothiazin-2-amine 5,5-dioxide, 6-methyl-N-[4-(morpholin-4-yl)phenyl]-6H-pyrimido[5,4-c][2,1]benzothiazin-2-amine 5,5-dioxide, 6-methyl-N-[4-(pyrrolidin-1-ylmethyl)phenyl]-6H-pyrimido[5,4-c][2,1]benzothiazin-2-amine 5,5-dioxide, 6-allyl-2-{[4-(4-methylpiperazin-1-yl)phenyl]amino}-6H-pyrimido[5,4-c][2,1]benzothiazine-7-carboxylic acid 5,5-dioxide, methyl 6-allyl-2-{[4-(4-methylpiperazin-1-yl)phenyl]amino}-6H-pyrimido[5,4-c][2,1]benzothiazine-7-carboxylate 5,5-dioxide, 6-allyl-N-methyl-2-{[4-(4-methylpiperazin-1-yl)phenyl]amino}-6H-pyrimido[5,4-c][2,1]benzothiazine-7-carboxamide 5,5-dioxide, 6-allyl-N-(2-hydroxyethyl)-2-{[4-(4-methylpiperazin-1-yl)phenyl]amino}-6H-pyrimido[5,4-c][2,1]benzothiazine-7-carboxamide 5,5-dioxide, 6-allyl-8-bromo-N-phenyl-6H-pyrimido[5,4-c][2,1]benzothiazin-2-amine 5,5-dioxide, 6-allyl-8-bromo-N-[4-(4-methylpiperazin-1-yl)phenyl]-6H-pyrimido[5,4-c][2,1]benzothiazin-2-amine 5,5-dioxide, methyl 2-{[4-(4-methylpiperazin-1-yl)phenyl]amino}-6H-pyrimido[5,4-c][2,1]benzothiazine-8-carboxylate 5,5-dioxide, 8-bromo-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-8-phenyl-6-propyl-6H-pyrimido[5,4-c][2,1]benzothiazin-2-amine 5,5-dioxide, N-[4-(4-methylpiperazin-1-yl)phenyl]-6-propyl-8-(pyridin-3-yl)-6H-pyrimido[5,4-c][2,1]benzothiazin-2-amine 5,5-dioxide, N-[4-(4-methylpiperazin-1-yl)phenyl]-6-propyl-8-(1H-pyrazol-4-yl)-6H-pyrimido[5,4-c][2,1]benzothiazin-2-amine 5,5-dioxide, 4-(2-{[4-(4-methylpiperazin-1-yl)phenyl]amino}-5,5-dioxido-6-propyl-6H-pyrimido[5,4-c][2,1]benzothiazin-8-yl)benzamide, N-cyclopropyl-4-(2-{[4-(4-methylpiperazin-1-yl)phenyl]amino}-5,5-dioxido-6-propyl-6H-pyrimido[5,4-c][2,1]benzothiazin-8-yl)benzamide, 8-(2-aminopyrimidin-5-yl)-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-6-propyl-8-(3-thienyl)-6H-pyrimido[5,4-c][2,1]benzothiazin-2-amine 5,5-dioxide, 4-(2-{[4-(4-methylpiperazin-1-yl)phenyl]amino}-5,5-dioxido-6-propyl-6H-pyrimido[5,4-c][2,1]benzothiazin-8-yl)phenol, N-[4-(4-methylpiperazin-1-yl)phenyl]-6-propyl-8-(pyridin-4-yl)-6H-pyrimido[5,4-c][2,1]benzothiazin-2-amine 5,5-dioxide, N-[4-(4-methylpiperazin-1-yl)phenyl]-6-propyl-8-(1H-pyrrolo[2,3-b]pyridin-3-yl)-6H-pyrimido[5,4-c][2,1]benzothiazin-2-amine 5,5-dioxide, methyl 2-{[4-(4-methylpiperazin-1-yl)phenyl]amino}-6-propyl-6H-pyrimido[5,4-c][2,1]benzothiazine-8-carboxylate 5,5-dioxide, 2-{[4-(4-methylpiperazin-1-yl)phenyl]amino}-6-propyl-6H-pyrimido[5,4-c][2,1]benzothiazine-8-carboxamide 5,5-dioxide, 2-(2-{[4-(4-methylpiperazin-1-yl)phenyl]amino}-5,5-dioxido-6-propyl-6H-pyrimido[5,4-c][2,1]benzothiazin-8-yl)propan-2-ol, N-cyclohexyl-2-{[4-(4-methylpiperazin-1-yl)phenyl]amino}-6-propyl-6H-pyrimido[5,4-c][2,1]benzothiazine-8-carboxamide 5,5-dioxide, N-methyl-2-{[4-(4-methylpiperazin-1-yl)phenyl]amino}-6-propyl-6H-pyrimido[5,4-c][2,1]benzothiazine-8-carboxamide 5,5-dioxide, N,N-dimethyl-2-{[4-(4-methylpiperazin-1-yl)phenyl]amino}-6-propyl-6H-pyrimido[5,4-c][2,1]benzothiazine-8-carboxamide 5,5-dioxide, N-(2-hydroxyethyl)-2-{[4-(4-methylpiperazin-1-yl)phenyl]amino}-6-propyl-6H-pyrimido[5,4-c][2,1]benzothiazine-8-carboxamide 5,5-dioxide, N-(2-methoxyethyl)-2-{[4-(4-methylpiperazin-1-yl)phenyl]amino}-6-propyl-6H-pyrimido[5,4-c][2,1]benzothiazine-8-carboxamide 5,5-dioxide, N-(trans-4-aminocyclohexyl)-2-{[4-(4-methylpiperazin-1-yl)phenyl]amino}-6-propyl-6H-pyrimido[5,4-c][2,1]benzothiazine-8-carboxamide 5,5-dioxide, 2-{[4-(4-methylpiperazin-1-yl)phenyl]amino}-6-propyl-N-(pyridin-3-ylmethyl)-6H-pyrimido[5,4-c][2,1]benzothiazine-8-carboxamide 5,5-dioxide, methyl 2-{[4-(4-methylpiperazin-1-yl)phenyl]amino}-6-phenyl-6H-pyrimido[5,4-c][2,1]benzothiazine-8-carboxylate 5,5-dioxide, methyl 6-(3-methylphenyl)-2-{[4-(4-methylpiperazin-1-yl)phenyl]amino}-6H-pyrimido[5,4-c][2,1]benzothiazine-8-carboxylate 5,5-dioxide, methyl 6-(3,5-dichlorophenyl)-2-{[4-(4-methylpiperazin-1-yl)phenyl]amino}-6H-pyrimido[5,4-c][2,1]benzothiazine-8-carboxylate 5,5-dioxide, methyl 6-[3,5-bis(trifluoromethyl)phenyl]-2-{[4-(4-methylpiperazin-1-yl)phenyl]amino}-6H-pyrimido[5,4-c][2,1]benzothiazine-8-carboxylate 5,5-dioxide, 8-(1H-imidazol-1-yl)-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-6-propyl-8-(1H-pyrrol-1-yl)-6H-pyrimido[5,4-c][2,1]benzothiazin-2-amine 5,5-dioxide, N-[4-(4-methylpiperazin-1-yl)phenyl]-6-propyl-8-(1H-1,2,4-triazol-1-yl)-6H-pyrimido[5,4-c][2,1]benzothiazin-2-amine 5,5-dioxide, methyl 6-(2,6-dichlorobenzyl)-2-{[4-(4-methylpiperazin-1-yl)phenyl]amino}-6H-pyrimido[5,4-c][2,1]benzothiazine-8-carboxylate 5,5-dioxide, 9-bromo-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-9-phenyl-6-propyl-6H-pyrimido[5,4-c][2,1]benzothiazin-2-amine 5,5-dioxide, N-[4-(4-methylpiperazin-1-yl)phenyl]-6-propyl-9-(pyridin-3-yl)-6H-pyrimido[5,4-c][2,1]benzothiazin-2-amine 5,5-dioxide, N-[4-(4-methylpiperazin-1-yl)phenyl]-6-propyl-9-(pyridin-4-yl)-6H-pyrimido[5,4-c][2,1]benzothiazin-2-amine 5,5-dioxide, N-methyl-3-(2-{[4-(4-methylpiperazin-1-yl)phenyl]amino}-5,5-dioxido-6-propyl-6H-pyrimido[5,4-c][2,1]benzothiazin-9-yl)benzamide, 9-{2-[(dimethylamino)methyl]phenyl}-N-[4-(4-methylpiperazin-1-yl)phenyl]-6-propyl-6H-pyrimido[5,4-c][2,1]benzothiazin-2-amine 5,5-dioxide, N-[5-(4-methylpiperazin-1-yl)pyridin-2-yl]-6-(prop-2-en-1-yl)-6H-pyrido[2,3-c]pyrimido[4,5-e][1,2]thiazin-2-amine 5,5-dioxide, and N-[5-(piperazin-1-yl)pyridin-2-yl]-6-(prop-2-en-1-yl)-6H-pyrido[2,3-c]pyrimido[4,5-e][1,2]thiazin-2-amine 5,5-dioxide.

Embodiments of Formula (II)

In one embodiment, the present invention is directed, in part, to a class of compounds having a structure of formula (II),

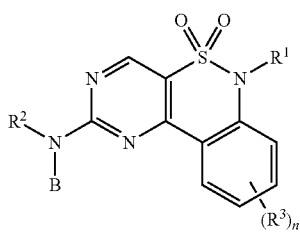

formula (II)

wherein $R^1$, $R^2$, $R^3$, B and n are as described in formula (I).

In one embodiment of formula (II), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, $-OR^a$, $-C(O)R^a$, $-C(O)OR^a$, $-OC(O)R^a$, $-NR^bR^c$, $-NR^bC(O)R^a$, $-NHC(O)NHR^b$, $-C(O)NR^bR^c$, $-NHSO_2R^a$, and $-SO_2NR^bNR^c$. In another embodiment of formula (II), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (II), $R^1$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2CH=CH_2$, $CH_2CH=CHCH_2$, or $-CH_2CH_2CH=CH_2$.

In one embodiment of formula (II), $R^1$ is aryl or aryl-$C_{1-6}$-alkyl, wherein the aryl, alone or as part of another moiety, is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, $-OR^d$, $-C(O)R^d$, $-C(O)OR^d$, $-OC(O)R^d$, $-SR^d$, $-S(O)R^d$, $-SO_2R^d$, $-NR^eR^f$, $-NHC(O)R^e$, $-NHC(O)NHR^e$, $-NHC(O)OR^e$, $-NHSO_2R^d$, $-C(O)NHR^e$, and $-SO_2NHNR^e$. In another embodiment, $R^1$ is phenyl or phenyl-$C_{1-6}$-alkyl, wherein the phenyl is optionally substituted with one, two or three $C_{1-6}$-alkyl, $C_{1-6}$-haloalkyl, or halogen.

In one embodiment of formula (II), $R^2$ is H.

In one embodiment of formula (II), n is 0.

In one embodiment of formula (II), $R^3$ is halo, $-OR^6$, $-C(O)OR^6$, $-C(O)NR^7R^8$, or $-NR^7R^8$ and n is 1. In another embodiment of formula (II), In another embodiment, $R^3$ is aryl or heteroaryl, wherein the aryl or heteroaryl is optionally substituted with one or more $R^9$, and $R^9$ is halo, $C_{1-6}$-alkyl, $C_{1-6}$-haloalkyl, $OR^m$, $C(O)R^m$, $C(O)NR''R^o$, $C(O)OR^m$, $NR''R^o$, or $NR''C(O)R^m$, and n is 1.

In one embodiment of formula (II), B is $C_{3-8}$ cyloalkyl, wherein the $C_{3-8}$ cyloalkyl is unsubstituted. In another embodiment of formula (II), B is $C_{3-8}$ cyloalkyl, wherein $C_{3-8}$ cyloalkyl is substituted with one, two, or three substituents selected from the group consisting of halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In another embodiment of formula (II), B is naphthyl, tetrahydronaphthyl, indenyl, or indanyl, wherein the naphthyl, tetrahydronaphthyl, indenyl, or indanyl is unsubstituted. In yet another embodiment of formula (II), B is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In one embodiment of formula (II), B is phenyl. In another embodiment of formula (II), B is phenyl, wherein the phenyl is unsubstituted. In another embodiment of formula (II), B is phenyl, wherein the phenyl is substituted with one, two, or three $R^4$, and $R^4$ is halo, $C_{1-6}$-alkyl, $C_{1-6}$ haloalkyl, $OR^g$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (II), $R^{10}$ is $C_{1-6}$-alkyl, $C_{1-6}$ haloalkyl, or $C(O)R^p$; $R^g$ is optionally substituted $C_{1-6}$ alkyl, $C_{1-6}$ haloalkyl, $C_{3-8}$ cycloalkyl; and RP is $C_{1-6}$ alkyl, $C_{1-6}$ haloalkyl, or $C_{3-8}$ cycloalkyl.

In one embodiment of formula (II), B is phenyl, wherein the phenyl is substituted with heterocycloalkyl and optionally one or two $R^4$, wherein $R^4$ is halo, $C_{1-6}$-alkyl, $C_{1-6}$ haloalkyl, or $OR^g$, wherein the heterocycloalkyl is optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (II), B is

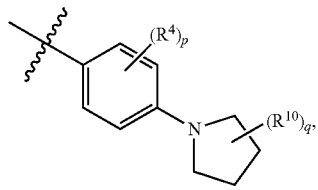

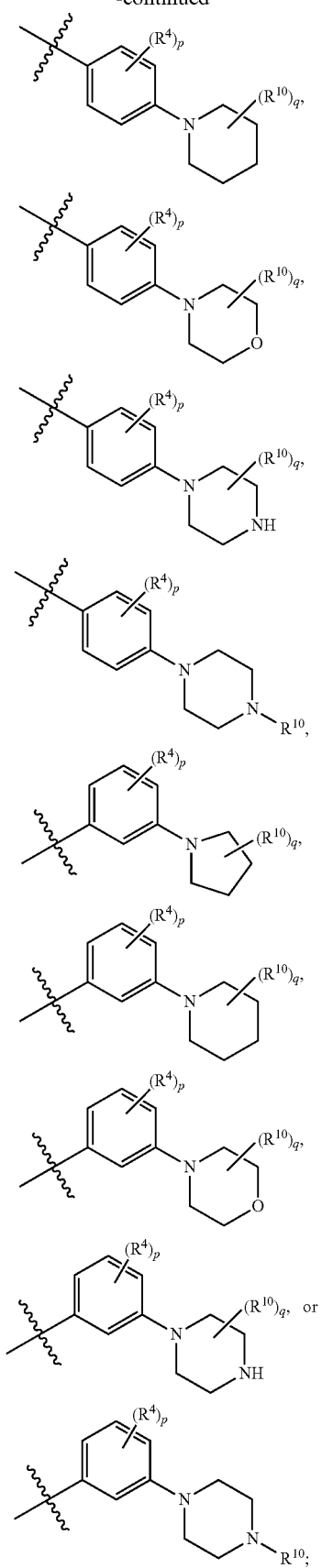

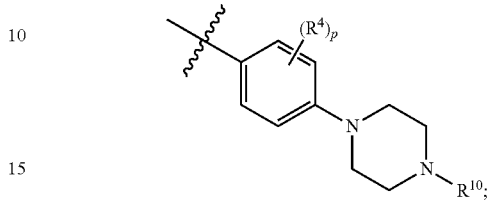

wherein $R^4$ is halo, $C_{1-6}$-alkyl, $C_{1-6}$ haloalkyl, or $OR^g$; p is 0 or 1; $R^{10}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and q is 0 or 1.

In one embodiment of formula (II), B is $R^4$ is halo, $C_{1-6}$-alkyl, $C_{1-6}$ haloalkyl, or $OR^g$; $R^{10}$ is $C_{1-6}$-alkyl and p is 0 or 1.

In one embodiment of formula (II), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (II), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (II), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (II), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (II), B is unsubstituted. In another embodiment of formula (II), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment of formula (II), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (II), B is unsubstituted. In another embodiment of formula (II), B is substituted with one, two, or three $R^5$, and $R^5$ is halo, $C_{1-6}$-alkyl, $C_{1-6}$-haloalkyl, $OR^j$, $C(O)R^j$, $C(O)OR^j$, $NR^kR^j$, or $S(O)_2R^j$.

In one embodiment, the present invention is directed, in part, to a class of compounds having a structure of formula (IIA), (IIB), (IIC), (IID), (IIE), (IIF), (IIG), or (IIH):

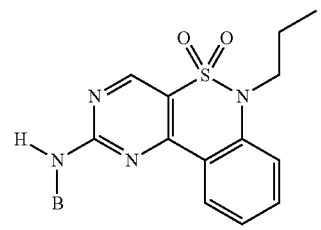

formula (IIA)

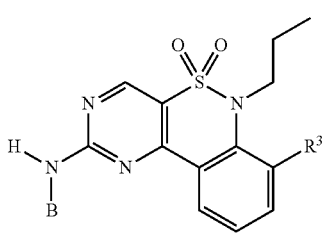

formula (IIB)

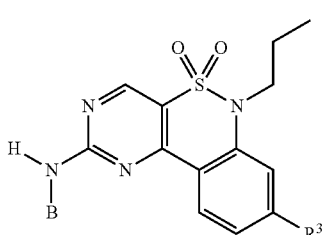

formula (IIC)

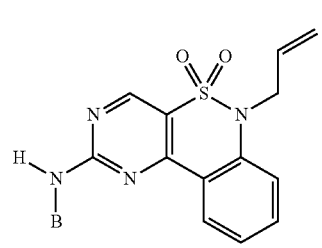

formula (IID)

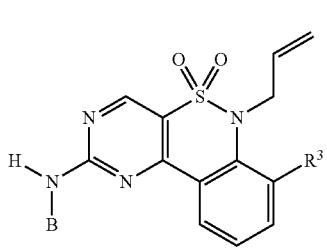

formula (IIE)

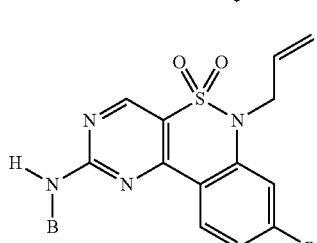

formula (IIF)

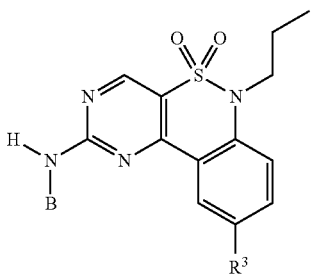

formula (IIG)

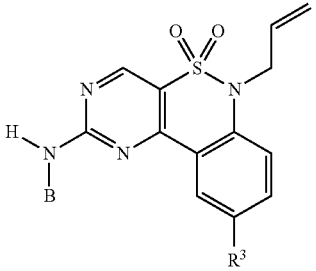

formula (IIH)

wherein $R^3$ and B are as described in formula (II).

Specific embodiments contemplated as part of the invention include, but are not limited to, compounds of formula (II), for example:

6-allyl-N-[4-(4-methylpiperazin-1-yl)phenyl]-6H-pyrimido[5,4-c][2,1]benzothiazin-2-amine 5,5-dioxide;

N-[4-(4-methylpiperazin-1-yl)phenyl]-6-[(1E)-prop-1-en-1-yl]-6H-pyrimido[5,4-c][2,1]benzothiazin-2-amine 5,5-dioxide;

6-allyl-N-{4-[2-(diethylamino)ethoxy]phenyl}-6H-pyrimido[5,4-c][2,1]benzothiazin-2-amine 5,5-dioxide;

6-allyl-N-cyclohexyl-6H-pyrimido[5,4-c][2,1]benzothiazin-2-amine 5,5-dioxide;

1-{6[(6-allyl-5,5-dioxido-6H-pyrimido[5,4-c][2,1]benzothiazin-2-yl)amino]-2,3-dihydro-1H-indol-1-yl}ethanone;

6-[(6-allyl-5,5-dioxido-6H-pyrimido[5,4-c][2,1]benzothiazin-2-yl)amino]-2H-1,4-benzoxazin-3(4H)-one;

6-allyl-N-(1-methyl-1,2,3,4-tetrahydroquinolin-7-yl)-6H-pyrimido[5,4-c][2,1]benzothiazin-2-amine 5,5-dioxide;

6-allyl-N-[4-(4-methylpiperidin-1-yl)phenyl]-6H-pyrimido[5,4-c][2,1]benzothiazin-2-amine 5,5-dioxide;

1-(4-{4-[(6-allyl-5,5-dioxido-6H-pyrimido[5,4-c][2,1]benzothiazin-2-yl)amino]phenyl}piperazin-1-yl)ethanone;

6-allyl-N-[4-(piperidin-1-yl)phenyl]-6H-pyrimido[5,4-c][2,1]benzothiazin-2-amine 5,5-dioxide;

6-allyl-N-[2-methoxy-4-(4-methylpiperazin-1-yl)phenyl]-6H-pyrimido[5,4-c][2,1]benzothiazin-2-amine 5,5-dioxide;

6-allyl-N-[4-(morpholin-4-yl)phenyl]-6H-pyrimido[5,4-c][2,1]benzothiazin-2-amine 5,5-dioxide;

6-allyl-N-[3-(4-methylpiperazin-1-yl)phenyl]-6H-pyrimido[5,4-c][2,1]benzothiazin-2-amine 5,5-dioxide;

6-allyl-N-[4-(1-methylpiperidin-4-yl)phenyl]-6H-pyrimido[5,4-c][2,1]benzothiazin-2-amine 5,5-dioxide;

6-allyl-N-(2,4,4-trimethyl-1,2,3,4-tetrahydroisoquinolin-7-yl)-6H-pyrimido[5,4-c][2,1]benzothiazin-2-amine 5,5-dioxide;

6-allyl-N-phenyl-6H-pyrimido[5,4-c][2,1]benzothiazin-2-amine 5,5-dioxide;

6-allyl-N-[4-(piperazin-1-yl)phenyl]-6H-pyrimido[5,4-c][2,1]benzothiazin-2-amine 5,5-dioxide;

6-allyl-N-(1,2,3,4-tetrahydroisoquinolin-7-yl)-6H-pyrimido[5,4-c][2,1]benzothiazin-2-amine 5,5-dioxide;

6-allyl-N-(pyridin-4-yl)-6H-pyrimido[5,4-c][2,1]benzothiazin-2-amine 5,5-dioxide;

6-allyl-N-(2'-methyl-2',3'-dihydro-1'H-spiro[cyclopropane-1,4'-isoquinolin]-7'-yl)-6H-pyrimido[5,4-c][2,1]benzothiazin-2-amine 5,5-dioxide;

6-allyl-N-(1,2,3,4-tetrahydroquinolin-7-yl)-6H-pyrimido[5,4-c][2,1]benzothiazin-2-amine 5,5-dioxide;

6-allyl-N-[3-fluoro-4-(piperazin-1-yl)phenyl]-6H-pyrimido[5,4-c][2,1]benzothiazin-2-amine 5,5-dioxide;

6-methyl-N-[4-(4-methylpiperazin-1-yl)phenyl]-6H-pyrimido[5,4-c][2,1]benzothiazin-2-amine 5,5-dioxide;

6-methyl-N-[4-(morpholin-4-yl)phenyl]-6H-pyrimido[5,4-c][2,1]benzothiazin-2-amine 5,5-dioxide;

6-methyl-N-[4-(pyrrolidin-1-ylmethyl)phenyl]-6H-pyrimido[5,4-c][2,1]benzothiazin-2-amine 5,5-dioxide;

6-allyl-2-{[4-(4-methylpiperazin-1-yl)phenyl]amino}-6H-pyrimido[5,4-c][2,1]benzothiazine-7-carboxylic acid 5,5-dioxide;

methyl 6-allyl-2-{[4-(4-methylpiperazin-1-yl)phenyl]amino}-6H-pyrimido[5,4-c][2,1]benzothiazine-7-carboxylate 5,5-dioxide;

6-allyl-N-methyl-2-{[4-(4-methylpiperazin-1-yl)phenyl]amino}-6H-pyrimido[5,4-c][2,1]benzothiazine-7-carboxamide 5,5-dioxide;

6-allyl-N-(2-hydroxyethyl)-2-{[4-(4-methylpiperazin-1-yl)phenyl]amino}-6H-pyrimido[5,4-c][2,1]benzothiazine-7-carboxamide 5,5-dioxide;

6-allyl-8-bromo-N-[4-(4-methylpiperazin-1-yl)phenyl]-6H-pyrimido[5,4-c][2,1]benzothiazin-2-amine 5,5-dioxide;

methyl 2-{[4-(4-methylpiperazin-1-yl)phenyl]amino}-6H-pyrimido[5,4-c][2,1]benzothiazine-8-carboxylate 5,5-dioxide;

8-bromo-N-[4-(4-methylpiperazin-1-yl)phenyl]-6-propyl-6H-pyrimido[5,4-c][2,1]benzothiazin-2-amine 5,5-dioxide;

N-[4-(4-methylpiperazin-1-yl)phenyl]-6-propyl-6H-pyrimido[5,4-c][2,1]benzothiazin-2-amine 5,5-dioxide;

N-[4-(4-methylpiperazin-1-yl)phenyl]-8-phenyl-6-propyl-6H-pyrimido[5,4-c][2,1]benzothiazin-2-amine 5,5-dioxide;

N-[4-(4-methylpiperazin-1-yl)phenyl]-6-propyl-8-(pyridin-3-yl)-6H-pyrimido[5,4-c][2,1]benzothiazin-2-amine 5,5-dioxide;

N-[4-(4-methylpiperazin-1-yl)phenyl]-6-propyl-8-(1H-pyrazol-4-yl)-6H-pyrimido[5,4-c][2,1]benzothiazin-2-amine 5,5-dioxide;

4-(2-{[4-(4-methylpiperazin-1-yl)phenyl]amino}-5,5-dioxido-6-propyl-6H-pyrimido[5,4-c][2,1]benzothiazin-8-yl)benzamide;

N-cyclopropyl-4-(2-{[4-(4-methylpiperazin-1-yl)phenyl]amino}-5,5-dioxido-6-propyl-6H-pyrimido[5,4-c][2,1]benzothiazin-8-yl)benzamide;

8-(2-aminopyrimidin-5-yl)-N-[4-(4-methylpiperazin-1-yl)phenyl]-6-propyl-6H-pyrimido[5,4-c][2,1]benzothiazin-2-amine 5,5-dioxide;

N-[4-(4-methylpiperazin-1-yl)phenyl]-6-propyl-8-(3-thienyl)-6H-pyrimido[5,4-c][2,1]benzothiazin-2-amine 5,5-dioxide;

4-(2-{[4-(4-methylpiperazin-1-yl)phenyl]amino}-5,5-dioxido-6-propyl-6H-pyrimido[5,4-c][2,1]benzothiazin-8-yl)phenol;

N-[4-(4-methylpiperazin-1-yl)phenyl]-6-propyl-8-(pyridin-4-yl)-6H-pyrimido[5,4-c][2,1]benzothiazin-2-amine 5,5-dioxide;

N-[4-(4-methylpiperazin-1-yl)phenyl]-6-propyl-8-(1H-pyrrolo[2,3-b]pyridin-3-yl)-6H-pyrimido[5,4-c][2,1]benzothiazin-2-amine 5,5-dioxide;

methyl 2-{[4-(4-methylpiperazin-1-yl)phenyl]amino}-6-propyl-6H-pyrimido[5,4-c][2,1]benzothiazine-8-carboxylate 5,5-dioxide;

2-{[4-(4-methylpiperazin-1-yl)phenyl]amino}-6-propyl-6H-pyrimido[5,4-c][2,1]benzothiazine-8-carboxamide 5,5-dioxide;

2-(2-{[4-(4-methylpiperazin-1-yl)phenyl]amino}-5,5-dioxido-6-propyl-6H-pyrimido[5,4-c][2,1]benzothiazin-8-yl)propan-2-ol;

N-cyclohexyl-2-{[4-(4-methylpiperazin-1-yl)phenyl]amino}-6-propyl-6H-pyrimido[5,4-c][2,1]benzothiazine-8-carboxamide 5,5-dioxide;

N-methyl-2-{[4-(4-methylpiperazin-1-yl)phenyl]amino}-6-propyl-6H-pyrimido[5,4-c][2,1]benzothiazine-8-carboxamide 5,5-dioxide;

N,N-dimethyl-2-{[4-(4-methylpiperazin-1-yl)phenyl]amino}-6-propyl-6H-pyrimido[5,4-c][2,1]benzothiazine-8-carboxamide 5,5-dioxide;

N-(2-hydroxyethyl)-2-{[4-(4-methylpiperazin-1-yl)phenyl]amino}-6-propyl-6H-pyrimido[5,4-c][2,1]benzothiazine-8-carboxamide 5,5-dioxide;

N-(2-methoxyethyl)-2-{[4-(4-methylpiperazin-1-yl)phenyl]amino}-6-propyl-6H-pyrimido[5,4-c][2,1]benzothiazine-8-carboxamide 5,5-dioxide;

N-(trans-4-aminocyclohexyl)-2-{[4-(4-methylpiperazin-1-yl)phenyl]amino}-6-propyl-6H-pyrimido[5,4-c][2,1]benzothiazine-8-carboxamide 5,5-dioxide;

2-{[4-(4-methylpiperazin-1-yl)phenyl]amino}-6-propyl-N-(pyridin-3-ylmethyl)-6H-pyrimido[5,4-c][2,1]benzothiazine-8-carboxamide 5,5-dioxide;

methyl 2-{[4-(4-methylpiperazin-1-yl)phenyl]amino}-6-phenyl-6H-pyrimido[5,4-c][2,1]benzothiazine-8-carboxylate 5,5-dioxide;

methyl 6-(3-methylphenyl)-2-{[4-(4-methylpiperazin-1-yl)phenyl]amino}-6H-pyrimido[5,4-c][2,1]benzothiazine-8-carboxylate 5,5-dioxide;

8-(1H-imidazol-1-yl)-N-[4-(4-methylpiperazin-1-yl)phenyl]-6-propyl-6H-pyrimido[5,4-c][2,1]benzothiazin-2-amine 5,5-dioxide;

N-[4-(4-methylpiperazin-1-yl)phenyl]-6-propyl-8-(1H-pyrrol-1-yl)-6H-pyrimido[5,4-c][2,1]benzothiazin-2-amine 5,5-dioxide; and N-[4-(4-methylpiperazin-1-yl)phenyl]-6-propyl-8-(1H-1,2,4-triazol-1-yl)-6H-pyrimido[5,4-c][2,1]benzothiazin-2-amine 5,5-dioxide.

Embodiments of Formula (III)

In one embodiment, the present invention is directed, in part, to a class of compounds having a structure of formula (III),

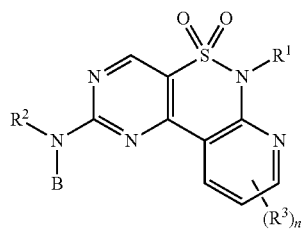

formula (III)

wherein $R^1$, $R^2$, $R^3$, B and n are as described in formula (I).

In one embodiment of formula (III), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In another embodiment of formula (III), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (III), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH=CH_2$, $CH_2CH=CHCH_2$, or —$CH_2CH_2CH=CH_2$.

In one embodiment of formula (III), $R^1$ is aryl or aryl-$C_{1-6}$-alkyl, wherein the aryl, alone or as part of another moiety, is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$. In another embodiment, $R^1$ is phenyl or phenyl-$C_{1-6}$-alkyl, wherein the phenyl is optionally substituted with one, two or three $C_{1-6}$-alkyl, $C_{1-6}$-haloalkyl, or halogen.

In one embodiment of formula (III), $R^2$ is H.

In one embodiment of formula (III), n is 0.

In one embodiment of formula (III), B is $C_{3-8}$ cyloalkyl, wherein the $C_{3-8}$ cyloalkyl is unsubstituted. In another embodiment of formula (III), B is $C_{3-8}$ cyloalkyl, wherein $C_{3-8}$ cyloalkyl is substituted with one, two, or three substituents selected from the group consisting of halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In another embodiment of formula (III), B is naphthyl, tetrahydronaphthyl, indenyl, or indanyl, wherein the naphthyl, tetrahydronaphthyl, indenyl, or indanyl is unsubstituted. In yet another embodiment of formula (III), B is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In one embodiment of formula (III), B is phenyl. In one embodiment of formula (III), B is phenyl, wherein the phenyl is unsubstituted. In another embodiment of formula (III), B is phenyl, wherein the phenyl is substituted with one, two, or three $R^4$, and $R^4$ is halo, $C_{1-6}$-alkyl, $C_{1-6}$ haloalkyl, $OR^g$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (III), $R^{10}$ is $C_{1-6}$-alkyl, $C_{1-6}$ haloalkyl, or $C(O)R^p$; $R^g$ is optionally substituted $C_{1-6}$ alkyl, $C_{1-6}$ haloalkyl, $C_{3-8}$ cycloalkyl; and $R^p$ is $C_{1-6}$ alkyl, $C_{1-6}$ haloalkyl, or $C_{3-8}$ cycloalkyl.

In one embodiment of formula (III), B is phenyl, wherein the phenyl is substituted with heterocycloalkyl and optionally one or two $R^4$, wherein $R^4$ is halo, $C_{1-6}$-alkyl, $C_{1-6}$ haloalkyl, or $OR^g$, wherein the heterocycloalkyl is optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (III), B is

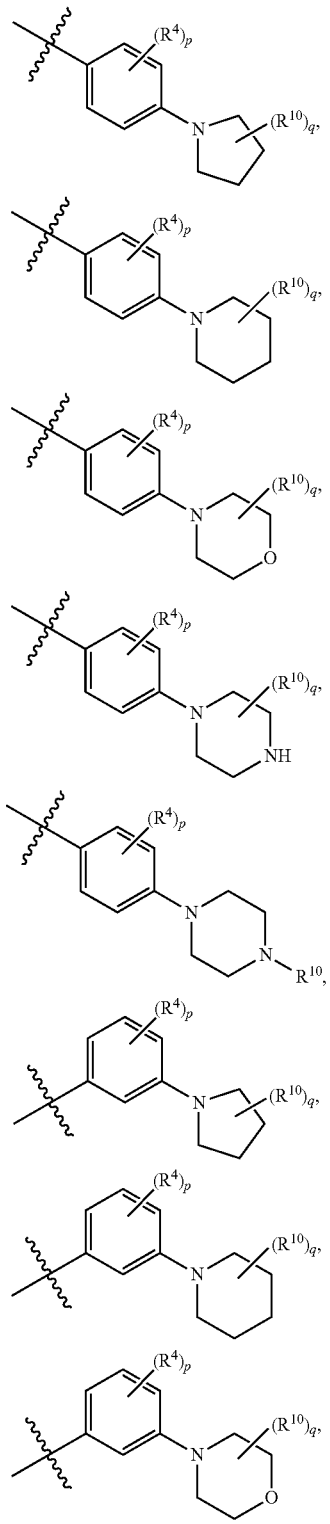

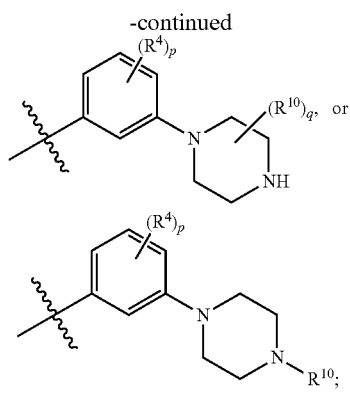

wherein $R^4$ is halo, $C_{1-6}$-alkyl, $C_{1-6}$ haloalkyl, or $OR^g$; p is 0 or 1; $R^{10}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and q is 0 or 1.

In one embodiment of formula (III), B is

R⁴ is halo, $C_{1-6}$-alkyl, $C_{1-6}$ haloalkyl, or $OR^g$; $R^{10}$ is $C_{1-6}$-alkyl and p is 0 or 1.

In one embodiment of formula (III), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (III), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (III), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (III), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (III), B is unsubstituted. In another embodiment of formula (II), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment of formula (III), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (III), B is unsubstituted. In another embodiment of formula (III), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment, the present invention is directed, in part, to a class of compounds having a structure of formula (IIIA) or (IIIB),

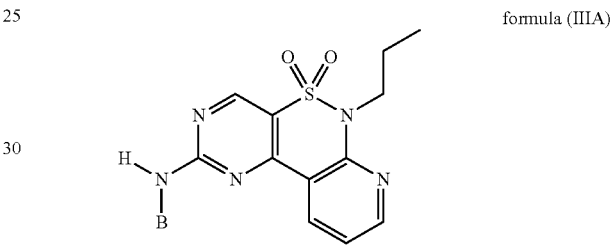

formula (IIIA)

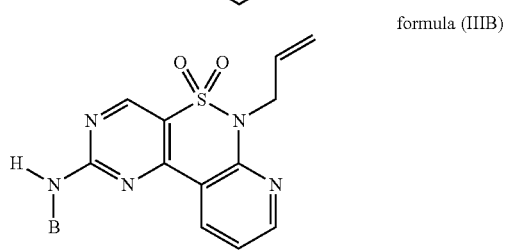

formula (IIIB)

wherein B are as described in formula (III).

Specific embodiments contemplated as part of the invention include, but are not limited to, compounds of formula (III), for example:

6-allyl-N-(1,2,3,4-tetrahydroisoquinolin-7-yl)-6H-pyrido[2,3-c]pyrimido[4,5-e][1,2]thiazin-2-amine 5,5-dioxide;

6-allyl-N-[4-(piperazin-1-yl)phenyl]-6H-pyrido[2,3-c]pyrimido[4,5-e][1,2]thiazin-2-amine 5,5-dioxide;

1-{6-[(6-allyl-5,5-dioxido-6H-pyrido[2,3-c]pyrimido[4,5-e][1,2]thiazin-2-yl)amino]-2,3-dihydro-1H-indol-1-yl}ethanone;

6-allyl-N-[3-fluoro-4-(piperazin-1-yl)phenyl]-6H-pyrido[2,3-c]pyrimido[4,5-e][1,2]thiazin-2-amine 5,5-dioxide;

6-allyl-N-[4-(piperidin-4-yl)phenyl]-6H-pyrido[2,3-c]pyrimido[4,5-e][1,2]thiazin-2-amine 5,5-dioxide;

6-allyl-N-(1,2,3,4-tetrahydroquinolin-7-yl)-6H-pyrido[2,3-c]pyrimido[4,5-e][1,2]thiazin-2-amine 5,5-dioxide;

6-allyl-N-{4-[2-(diethylamino)ethoxy]phenyl}-6H-pyrido[2,3-c]pyrimido[4,5-e][1,2]thiazin-2-amine 5,5-dioxide;

6-allyl-N-[4-(4-methylpiperazin-1-yl)phenyl]-6H-pyrido[2,3-c]pyrimido[4,5-e][1,2]thiazin-2-amine 5,5-dioxide;

6-allyl-N-[3-methyl-4-(piperazin-1-yl)phenyl]-6H-pyrido[2,3-c]pyrimido[4,5-e][1,2]thiazin-2-amine 5,5-dioxide;

{4-[(6-allyl-5,5-dioxido-6H-pyrido[2,3-c]pyrimido[4,5-e] [1,2]thiazin-2-yl)amino]phenyl}(4-methylpiperazin-1-yl) methanone;

6-allyl-N-[2-methyl-4-(4-methylpiperazin-1-yl)phenyl]-6H-pyrido[2,3-c]pyrimido[4,5-e][1,2]thiazin-2-amine 5,5-dioxide;

6-allyl-N-[4-(pyrrolidin-3-yl)phenyl]-6H-pyrido[2,3-c]pyrimido[4,5-e][1,2]thiazin-2-amine 5,5-dioxide;

6-allyl-N-(1,2,3,4-tetrahydroisoquinolin-6-yl)-6H-pyrido[2,3-c]pyrimido[4,5-e][1,2]thiazin-2-amine 5,5-dioxide;

6-allyl-N-(2'-methyl-2',3'-dihydro-1'H-spiro[cyclopropane-1,4'-isoquinolin]-7'-yl)-6H-pyrido[2,3-c]pyrimido[4,5-e] [1,2]thiazin-2-amine 5,5-dioxide;

6-allyl-N-[4-(hexahydropyrrolo[1,2-a]pyrazin-2(1H)-yl) phenyl]-6H-pyrido[2,3-c]pyrimido[4,5-e][1,2]thiazin-2-amine 5,5-dioxide;

6-allyl-N-(1-methyl-1,2,3,4-tetrahydroquinolin-7-yl)-6H-pyrido[2,3-c]pyrimido[4,5-e][1,2]thiazin-2-amine 5,5-dioxide;

6-allyl-N-[3-methyl-4-(4-methylpiperazin-1-yl)phenyl]-6H-pyrido[2,3-c]pyrimido[4,5-e][1,2]thiazin-2-amine 5,5-dioxide;

6-allyl-N-[4-(piperazin-1-yl)-3-(trifluoromethyl)phenyl]-6H-pyrido[2,3-c]pyrimido[4,5-e][1,2]thiazin-2-amine 5,5-dioxide;

6-allyl-N-[4-(morpholin-4-yl)phenyl]-6H-pyrido[2,3-c]pyrimido[4,5-e][1,2]thiazin-2-amine 5,5-dioxide;

6-allyl-N-[3-methyl-4-(4-methyl-1,4-diazepan-1-yl)phenyl]-6H-pyrido[2,3-c]pyrimido[4,5-e][1,2]thiazin-2-amine 5,5-dioxide; and 6-allyl-N-(2',3'-dihydro-1'H-spiro[cyclopropane-1,4'-isoquinolin]-7'-yl)-6H-pyrido[2,3-c]pyrimido[4,5-e][1,2]thiazin-2-amine 5,5-dioxide.

Embodiments of Formula (IV)

In one embodiment, the present invention is directed, in part, to a class of compounds having a structure of formula (IV),

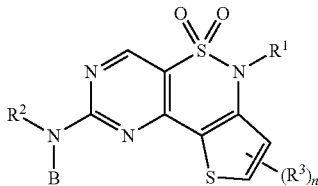

formula (IV)

wherein $R^1$, $R^2$, $R^3$, B and n are as described in formula (I).

In one embodiment of formula (IV), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —C(O) $R^a$, —C(O)$OR^a$, —OC(O)$R^a$, —$NR^bR^c$, —$NR^bC(O)R^a$, —NHC(O)$NHR^b$, —C(O)$NR^bR^c$, —$NHSO_2R^a$, and —$SO_2NR^bNR^c$. In another embodiment of formula (IV), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (IV), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH=CH_2$, $CH_2CH=CHCH_3$, or —$CH_2CH_2CH=CH_2$.

In one embodiment of formula (IV), $R^1$ is aryl or aryl-$C_{1-6}$-alkyl, wherein the aryl, alone or as part of another moiety, is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —C(O)$R^d$, —C(O)$OR^d$, —OC(O)$R^d$, —$SR^d$, —S(O)$R^d$, —$SO_2R^d$, —$NR^eR^f$, —NHC (O)$R^e$, —NHC(O)$NHR^e$, —NHC(O)$OR^e$, —$NHSO_2R^d$, —C(O)$NHR^e$, and —$SO_2NHNR^e$. In another embodiment, $R^1$ is phenyl or phenyl-$C_{1-6}$-alkyl, wherein the phenyl is optionally substituted with one, two or three $C_{1-6}$-alkyl, $C_{1-6}$-haloalkyl, or halogen.

In one embodiment of formula (IV), $R^2$ is H.

In one embodiment of formula (IV), n is 0.

In one embodiment of formula (IV), B is $C_{3-8}$ cyloalkyl, wherein the $C_{3-8}$ cyloalkyl is unsubstituted. In another embodiment of formula (IV), B is $C_{3-8}$ cyloalkyl, wherein $C_{3-8}$ cyloalkyl is substituted with one, two, or three substituents selected from the group consisting of halo, $C_{1-6}$-alkyl, $C_{1-6}$-haloalkyl, $OR^g$, $SR^g$, C(O)$R^g$, C(O)$NR^hR^i$, C(O)$OR^g$, $NR^hR^i$, $NR^hC(O)R^g$, $S(O)_2R^g$, $NR^hS(O)_2R^g$, and $S(O)_2NR^hR^i$.

In another embodiment of formula (IV), B is naphthyl, tetrahydronaphthyl, indenyl, or indanyl, wherein the naphthyl, tetrahydronaphthyl, indenyl, or indanyl is unsubstituted. In yet another embodiment of formula (IV), B is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, C(O)$R^g$, C(O)$NR^hR^i$, C(O)$OR^g$, $NR^hR^i$, $NR^hC(O)R^g$, $S(O)_2R^g$, $NR^hS(O)_2R^g$, and $S(O)_2NR^hR^i$.

In one embodiment of formula (IV), B is phenyl. In another embodiment of formula (IV), B is phenyl, wherein the phenyl is unsubstituted. In another embodiment of formula (IV), B is phenyl, wherein the phenyl is substituted with one, two, or three $R^4$, and $R^4$ is halo, $C_{1-6}$-alkyl, $C_{1-6}$ haloalkyl, $OR^g$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{10}$; wherein $R^{10}$ is halo, $C_{1-6}$-alkyl, $C_{1-6}$-haloalkyl, $OR^p$, C(O)$R^p$, C(O)$NR^qR^r$, C(O) $OR^p$, $NR^qR^r$, $NR^qC(O)R^p$, $S(O)_2R^p$, or $S(O)_2NR^qR^r$. In yet another embodiment of formula (IV), $R^{10}$ is $C_{1-6}$-alkyl, $C_{1-6}$ haloalkyl, or C(O)$R^p$; $R^g$ is optionally substituted $C_{1-6}$ alkyl, $C_{1-6}$ haloalkyl, $C_{3-8}$ cycloalkyl; and RP is $C_{1-6}$ alkyl, $C_{1-6}$ haloalkyl, or $C_{3-8}$ cycloalkyl.

In one embodiment of formula (IV), B is phenyl, wherein the phenyl is substituted with heterocycloalkyl and optionally one or two $R^4$, wherein $R^4$ is halo, $C_{1-6}$-alkyl, $C_{1-6}$ haloalkyl, or $OR^g$, wherein the heterocycloalkyl is optionally substituted with one, two, or three $R^{10}$; wherein $R^{10}$ is halo, $C_{1-6}$-alkyl, $C_{1-6}$-haloalkyl, $OR^p$, C(O)$R^p$, C(O)$NR^qR^r$, C(O)$OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo [1,2-a]pyrazin-2(1H)yl.

In another embodiment of formula (IV), B is

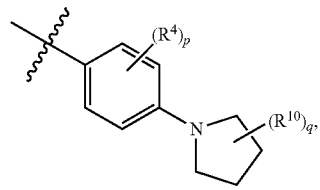

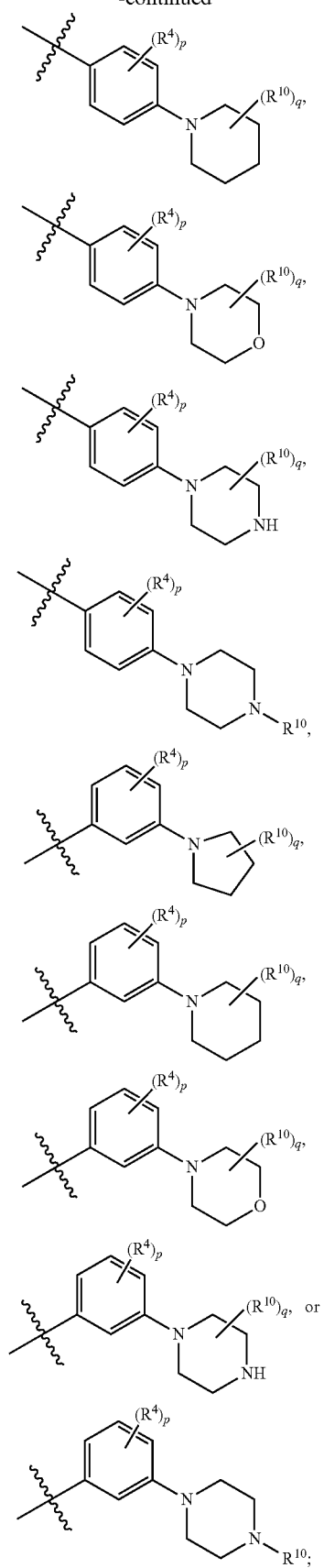

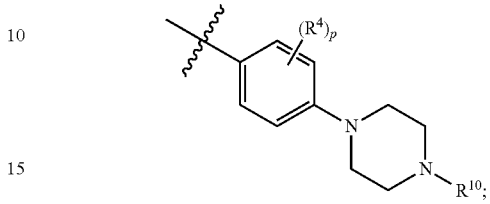

wherein $R^4$ is halo, $C_{1-6}$-alkyl, $C_{1-6}$ haloalkyl, or $OR^g$; p is 0 or 1; $R^{10}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and q is 0 or 1.

In one embodiment of formula (IV), B is $R^4$ is halo, $C_{1-6}$-alkyl, $C_{1-6}$ haloalkyl, or $OR^g$; $R^{10}$ is $C_{1-6}$-alkyl and p is 0 or 1.

In one embodiment of formula (IV), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (III), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (III), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (IV), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (IV), B is unsubstituted. In another embodiment of formula (II), B is substituted with one, two, or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

In one embodiment of formula (IV), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (IV), B is unsubstituted. In another embodiment of formula (IV), B is substituted with one, two, or three $R^5$, and $R^5$ is halo, $C_{1-6}$-alkyl, $C_{1-6}$-haloalkyl, $C(O)R^j$, $C(O)OR^j$, $NR^kR^l$, or $S(O)_2R^j$.

In one embodiment, the present invention is directed, in part, to a class of compounds having a structure of formula (IVA) or (IVB),

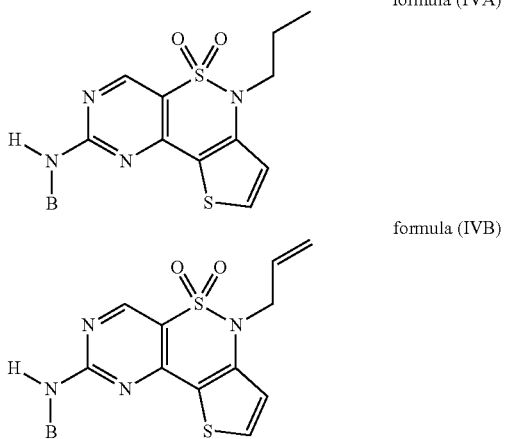

formula (IVA)

formula (IVB)

wherein B is as described in formula (IV).

Specific embodiments contemplated as part of the invention include, but are not limited to, compounds of formula (III), for example:

6-methyl-N-[4-(4-methylpiperazin-1-yl)phenyl]-6H-pyrimido[4,5-e]thieno[3,2-c][1,2]thiazin-2-amine 5,5-dioxide.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Schemes

Scheme 1

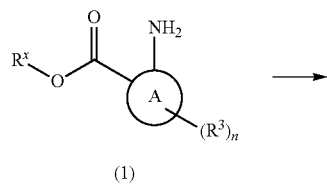

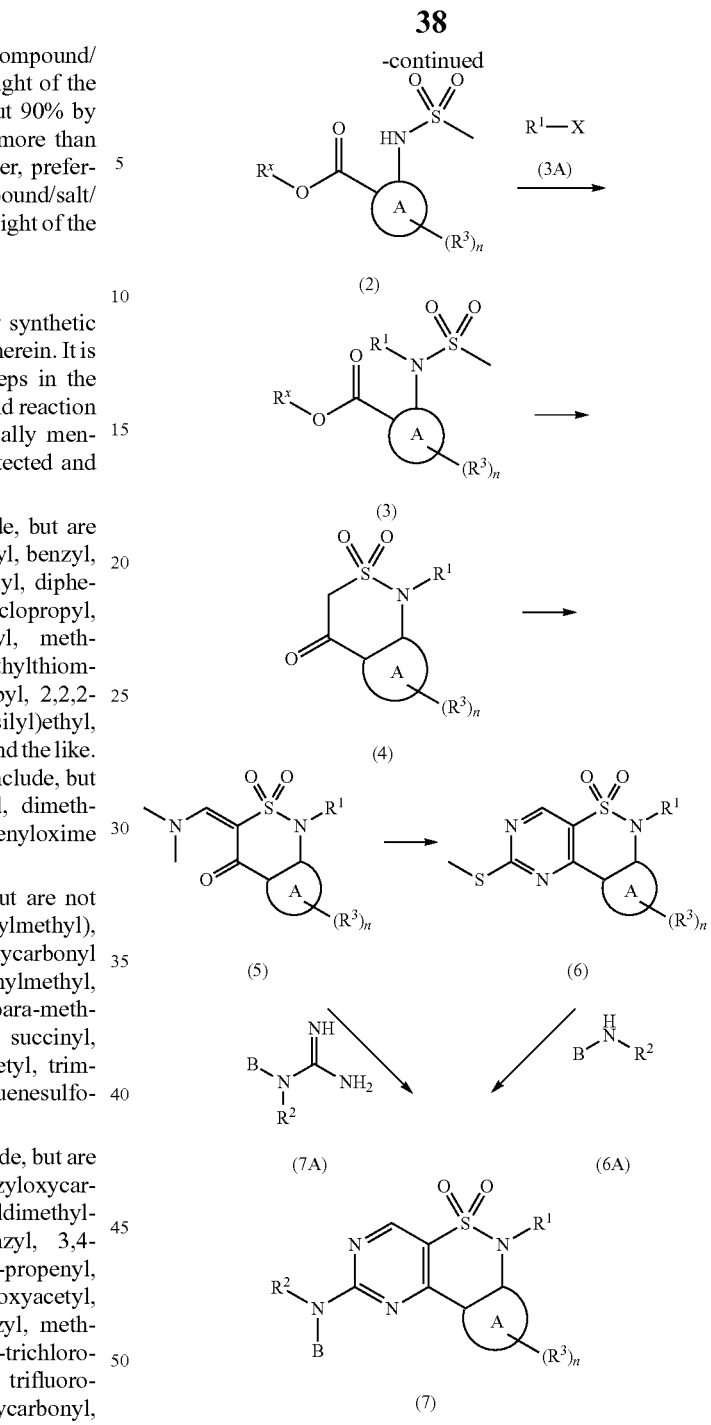

As shown in Scheme 1, compounds of formula (2), wherein A is phenyl, thiophenyl, or pyridyl, $R^x$ is alkyl, and $R^3$ and n are as described herein for Formula (I), can be prepared by reacting compounds of formula (I) with methanesulfonyl chloride in the presence of a base such as but not limited to triethylamine. The reaction is typically performed at reduced temperature in a solvent such as but not limited to dioxane. Alternatively, compounds of formula (1) can be reacted with methanesulfonic anhydride in the presence of a base such as but not limited to pyridine. The reaction is typically performed at elevated temperature in a solvent such as but not limited to 1,2-dichloroethane. Compounds of formula (2) can be reacted with compounds of formula (3A), wherein $R^1$ is as described herein and X is I, Br, or Cl, in the presence of a base such as but not limited to potassium carbonate, to provide compounds of formula (3). The base is typically added at reduced temperature in a solvent such as but not limited to N,N-dimethylformamide, and then the reaction is typically warmed to an elevated temperature. Compounds of formula (4) can be prepared by reacting compounds of formula (3) with a base such as but not limited to sodium hydride. The reaction is typically performed at ambient temperature in a solvent such as but not limited N,N-dimethylformamide. Compounds of formula (5) can be prepared by reacting compounds of formula (4) with N,N-dimethylformamide dimethyl acetal at an elevated temperature. Compounds of formula (5) can be reacted with S-methylthiourea in the presence of acetic acid to provide compounds of formula (6). The reaction is typically performed at an elevated temperature. Compounds of formula (6) can be reacted with 3-chloroperoxybenzoic acid in a solvent such as but not limited to toluene, followed by a base such as but not limited to diisopropylethylamine and compounds of formula (6A), wherein $R^2$ and B are as described herein, to provide compounds of formula (7) which are representative of compounds of formula (I). Alternatively, compounds of formula (5) can be reacted with compounds of formula (7A), wherein $R^2$ and B are as described herein, in a solvent such as but not limited to 2-methoxyethanol in the presence of a base such as but not limited to potassium carbonate, to provide compounds of formula (7) which are representative of compounds of formula (I).

Compounds of formula (8), wherein $R^1$ is alkenyl and $R^2$ and B are as described herein, and which can be prepared as described in Scheme 1, can be added to a mixture of a palladium catalyst such as but not limited to [1,1'-bis(diphenylphosphino)ferrocene]dichloropalladium(II) and a base such as but not limited to triethylamine in methanol followed by the addition of carbon monoxide (60 psi) to provide compounds of formula (9). The reaction is typically performed at elevated temperature. Compounds of formula (10), wherein $R^{1A}$ is aryl or heteroaryl, and which are representative of compounds of formula (I), can be prepared by reacting compounds of formula (9) with compounds of formula (10A) in the presence copper(II) acetate and a base such as but not limited to triethylamine. The reaction is typically performed at an elevated temperature, in a solvent such as but not limited to dichloromethane.

Scheme 3

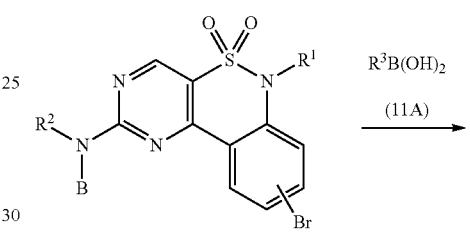

Scheme 2

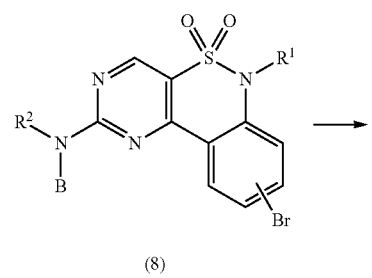

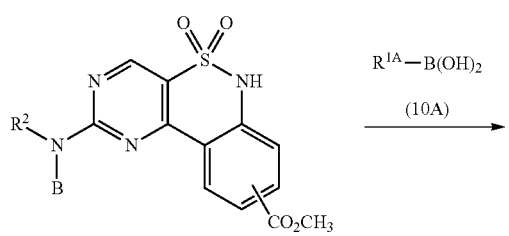

As shown in Scheme 3, compounds of formula (8), which can be prepared as described in Scheme 1, can be reacted with compounds of formula (11A), wherein $R^3$ is aryl or heteroaryl, under Suzuki coupling conditions known to those skilled in the art and readily available in the literature, to provide compounds of formula (11), which are representative of compounds of formula (I).

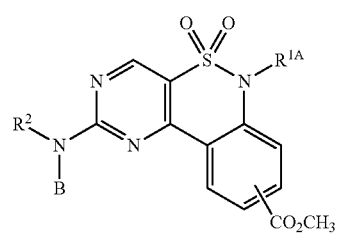

Scheme 4

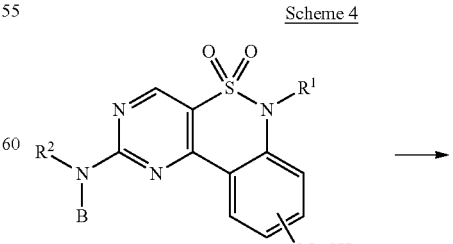

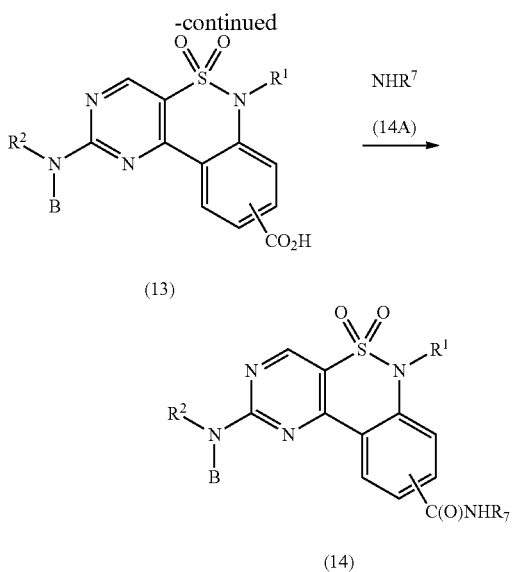

As shown in Scheme 4, hydrolysis of compounds of formula (12), wherein $R^1$, $R^2$, and B are as described herein, with a base such as but not limited to sodium hydroxide, lithium hydroxide, or potassium hydroxide will provide compounds of formula (13). Compounds of formula (13) can be reacted with amines of formula (14A) under coupling conditions known to those skilled in the art and readily available in the literature, to provide compounds of formula (14), which are representative of compounds of formula (I).

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all wee-1 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

In one group of embodiments, diseases and conditions of humans or other animals that can be treated with inhibitors of kinases, include, but are not limited to, tumors that are deficient in the p53 protein. The p53 protein is a tumor suppressor protein that is encoded in humans by the TP53 gene. The p53 protein regulates the cell cycle and therefore functions as a tumor suppressor that is involved in preventing cancer Inhibition of Wee1 kinases sensitizes tumor cells to DNA damage and/or cell cycle perturbation, especially tumors that have lost their $G_1$-phase checkpoint due to a deficiency in the p53 protein.

A discussion of the loss of expression of Wee1 and how it relates to deficiency in the p53 protein can be found in *Annual Review of Biochemistry*, 2004, 73:39-85.

Involvement of mutations in the p53 gene and human tumor types can be found in *Nature*, 1989, 342:705-708.

A discussion of Wee1 kinase and p53 deficient tumor cells can be found in *Molecular Cancer Therapy,* 2009, 8:11.

A discussion of p53 and Wee1 kinases and anti-cancer therapies can be found in *BMC Cancer* 2006, 6:292.

A discussion of Wee1 kinase and p53 deficient tumor cells can be found in *Current Clinical Pharmacology,* 2010, 5:186-191.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORE- TAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TRE-ANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806

(mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10XANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR®(gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXPERIMENTAL

Example 1

6-allyl-N-[4-(4-methylpiperazin-1-yl)phenyl]-6H-pyrimido[5,4-c][2,1]benzothiazin-2-amine 5,5-dioxide Example 1A ethyl 2-(methylsulfonamido)benzoate Methanesulfonyl chloride (2.80 mL, 36.0 mmol) was added slowly to a solution of ethyl 2-aminobenzoate (4.43 mL, 30 mmol) and triethylamine (12.54 ml, 90 mmol) in 100 mL dioxane at 0° C. The solution was allowed to warm to room temperature. The reaction was poured into saturated NaHCO$_3$ and extracted into CH$_2$Cl$_2$. The combined extracts were washed with 1M HCl (aqueous), and the organic layer was concentrated to afford the title compound which was used in the step without further purification.

Example 1B ethyl 2-(N-allylmethylsulfonamido)benzoate

A mixture of Example 1A (1.898 g, 7.8 mmol) and K$_2$CO$_3$ (2.211 g, 16 mmol) in 8.5 mL N,N-dimethylformamide was stirred at 0° C. for 15 minutes. Allyl bromide (0.846 ml, 10 mmol) was added dropwise. The mixture was slowly heated to 65° C. and stirred overnight. The reaction mixture was diluted with water and extracted with CHCl$_3$ (three times). The combined extracts were dried over Na$_2$SO$_4$, filtered, and concentrated. The crude product was isolated by flash chromatography (3-40% ethyl acetate/hexane) to afford the title compound.

Example 1C 1-allyl-1H-2,1-benzothiazin-4(3H)-one 2,2-dioxide

Example 1B (0.949 g, 3.35 mmol) in 5 mL N,N-dimethylformamide was added dropwise to a stirred suspension of 60% sodium hydride (0.268 g, 6.70 mmol) in 5 mL N,N-dimethylformamide at room temperature. The mixture was stirred at room temperature for 1 hour then acidified with 1N HCl (aq) and extracted into ethyl acetate. The combined extracts were washed with H$_2$O (four times), dried over Na$_2$SO$_4$, filtered, and concentrated. The isomers were separated by flash chromatography (5-50% ethyl acetate/hexane) to afford Example 1C and Example 1D.

Example 1D

1-[(1E)-prop-1-en-1-yl]-1H-2,1-benzothiazin-4(3H)-one 2,2-dioxide

Example 1B (0.949 g, 3.35 mmol) in 5 mL N,N-dimethylformamide was added dropwise to a stirred suspension of 60% sodium hydride (0.268 g, 6.70 mmol) in 5 mL N,N-dimethylformamide at room temperature. The mixture was stirred at room temperature for 1 hour then acidified with 1N HCl (aq) and extracted into ethyl acetate. The combined extracts were washed with H$_2$O (four times), dried over Na$_2$SO$_4$, filtered, and concentrated. The isomers were separated by flash chromatography (5-50% ethyl acetate/hexane) to afford Example 1C and Example 1D.

Example 1E 6-allyl-2-(methylthio)-6H-pyrimido[5,4-c][2,1]benzothiazine 5,5-dioxide A mixture of Example 1C (204 mg, 0.860 mmol) in N,N-dimethylformamide dimethyl acetal (574 μL, 4.30 mmol) was stirred at 65° C. for 2 hours, and concentrated. The residue was added to 4 mL acetic acid, treated with S-methylthiourea (85 mg, 0.946 mmol) and stirred overnight at 100° C. The reaction mixture was concentrated and the residue was purified by flash chromatography (5-70% ethyl acetate/hexane) to afford the title compound.

Example 1F 6-allyl-N-[4-(4-methylpiperazin-1-yl)phenyl]-6H-pyrimido[5,4-c][2,1]benzothiazin-2-amine 5,5-dioxide 3-Chloroperoxybenzoic acid (42.5 mg, 0.172 mmol) was added to a solution of Example 1E (50 mg, 0.157 mmol) in 1.5 mL toluene and the mixture was stirred at room temperature for 2 hours. Hunig's Base (0.074 mL, 0.423 mmol) and 4-(4-methylpiperazin-1-yl)aniline (29.9 mg, 0.157 mmol) were added and the reaction was stirred overnight at room temperature. The reaction mixture was concentrated. The residue was suspended in ethyl acetate, the solids were removed, and the filtrate was purified by reverse-phase HPLC on a Phenomenex Luna C8 AXIA column (30×75 mm, 100 Å) using a gradient of 10% to 95% acetonitrile: 10 mM ammonium acetate in water to afford the title compound. MS (ESI) m/e 463 (M+H)⁺. ¹H NMR (400 MHz, DMSO-d₆) δ ppm 2.23 (s, 3 H) 2.43-2.48 (m, 4 H) 3.07-3.17 (m, 4 H) 4.58 (d, J=5.19 Hz, 2 H) 5.13-5.31 (m, 2 H) 5.76-5.93 (m, 1 H) 6.98 (d, J=8.24 Hz, 2 H) 7.41-7.54 (m, 2 H) 7.54-7.78 (m, 3 H) 8.42 (d, J=7.63 Hz, 1 H) 8.91 (s, 1 H) 10.25 (s, 1 H).

Example 2

N-[4-(4-methylpiperazin-1-yl)phenyl]-6-[(1E)-prop-1-en-1-yl]-6H-pyrimido[5,4-c][2,1]benzothiazin-2-amine 5,5-dioxide

Example 2A

The title compound was prepared as described in Example 1E, substituting Example 1C with Example 1D.

Example 2B

N-[4-(4-methylpiperazin-1-yl)phenyl]-6-[(1E)-prop-1-en-1-yl]-6H-pyrimido[5,4-c][2,1]benzothiazin-2-amine 5,5-dioxide The title compound was prepared as described in Example 1F, substituting Example 1E with Example 2A. MS (ESI) m/e 463 (M+H)⁺. ¹H NMR (400 MHz, DMSO-d₆) δ ppm 1.64 (dd, J=6.87, 1.68 Hz, 3 H) 2.23 (s, 3 H) 2.40-2.48 (m, 4 H) 3.08-3.18 (m, 4 H) 6.01-6.11 (m, 1 H) 6.17 (dd, J=7.48, 1.68 Hz, 1 H) 6.98 (d, J=8.24 Hz, 2 H) 7.30 (d, J=8.24 Hz, 1H) 7.42-7.51 (m, 1 H) 7.55-7.80 (m, 3 H) 8.37-8.54 (m, 1 H) 8.91 (s, 1 H) 10.28 (s, 1 H).

Example 3

6-allyl-N-{4-[2-(diethylamino)ethoxy]phenyl}-6H-pyrimido[5,4-c][2,1]benzothiazin-2-amine 5,5-dioxide

Example 3A 6-allyl-2-(methylsulfinyl)-6H-pyrimido[5,4-c][2,1]benzothiazine 5,5-dioxide To a solution of Example 1E (1.15 g, 3.6 mmol) in 15 mL dichloromethane was added m-chloroperoxybenzoic acid (1 g, 4.5 mmol). After stirring for 1.5 hours at room temperature, the solution was washed with 1M sodium thiosulfate followed by saturated sodium bicarbonate. The organic phase was dried over magnesium sulfate, filtered, and concentrated to afford the title compound which was used in the next step without any further purification.

Example 3B 6-allyl-N-{4-[2-(diethylamino)ethoxy]phenyl}-6H-pyrimido[5,4-c][2,1]benzothiazin-2-amine 5,5-dioxide A solution of Example 3A (79.5 mg, 0.24 mmol), 4-[2-(diethylamino)ethoxy]aniline (60 mg, 0.29 mmol) and trifluoroacetic acid (1 μL) was stirred in 2 mL acetonitrile at 70° C. for 24 hours. The reaction mixture was cooled to room temperature and concentrated. The crude product was purified by RP-HPLC on a Phenomenex Luna C8(2) 5 um 100 Å AXIA column (30 mm×75 mm) using a gradient of 10% acetonitrile to 95%:0.1% TFA in water to afford the title compound. MS (ESI) m/e 480 (M+H)⁺. ¹H NMR (400 MHz, DMSO-d₆) δ ppm 10.39 (s, 1H), 9.57 (br s, 1H), 8.95 (s, 1H), 8.43 (d, 1H), 7.75 (m, 2H), 7.52 (d, 1H), 7.46 (t, 1H), 7.06 (d, 2H), 5.85 (m, 1H), 5.23 (m, 2H), 4.59 (d, 2H), 4.33 (t, 2H), 3.54 (d, 2H), 3.25 (m, 4H), 1.25 (m, 6H).

Example 4

6-allyl-N-cyclohexyl-6H-pyrimido[5,4-c][2,1]benzothiazin-2-amine 5,5-dioxide

The title compound was prepared as described in Example 3B, substituting cyclohexylamine for 4-[2-(diethylamino)ethoxy]aniline. MS (ESI) m/e 371 (M+H)⁺. ¹H NMR (500 MHz, DMSO-d₆, 90° C.) δ ppm 8.71 (s, 1H), 8.40 (d, 1H), 7.76 (d, 1H), 7.57 (m, 1H), 7.42 (m, 2H), 5.83 (m, 1H), 5.21 (m, 2H), 4.51 (m, 2H), 3.84 (m, 1H), 1.88 (m, 2H), 1.74 (m, 2H), 1.61 (m, 1H), 1.35 (m, 4H), 1.18 (m, 1H).

Example 5

1-{6-[(6-allyl-5,5-dioxido-6H-pyrimido[5,4-c][2,1]benzothiazin-2-yl)amino]-2,3-dihydro-1H-indol-1-yl}ethanone The title compound was prepared as described in Example 3B, substituting 1-acetyl-6-aminoindoline for 4-[2-(diethylamino)ethoxy]aniline. The title compound was recrystallized from DMSO:methanol. MS (ESI) m/e 448 (M+H)⁺. ¹H NMR (400 MHz, DMSO-d₆, 90° C.) δ ppm 10.08 (s, 1H), 8.86 (s, 1H), 8.69 (d, 2H), 7.70 (t, 1H), 7.44 (m, 2H), 7.32 (m, 1H), 7.18 (d, 1H), 5.85 (m, 1H), 5.18 (m, 2H), 4.55 (m, 2H), 4.12 (t, 2H), 3.11 (t, 2H), 2.21 (s, 3H).

Example 6

6-[(6-allyl-5,5-dioxido-6H-pyrimido[5,4-c][2,1]benzothiazin-2-yl)amino]-2H-1,4-benzoxazin-3(4H)-one The title compound was prepared as described in Example 3B, substituting 6-amino-2H-1,4-benzoxazin-3(4H)-one for 4-[2-(diethylamino)ethoxy]aniline. The title compound was recrystallized from DMSO:methanol. MS (ESI) m/e 436 (M+H)⁺. ¹H NMR (400 MHz, DMSO-d₆) δ ppm 10.95 (br s, 1H), 10.42 (s, 1H), 8.95 (s, 1H), 8.51 (d, 1H), 7.76 (m, 1H), 7.50 (m, 3H), 7.25 (d, 1H), 6.98 (d, 1H), 5.85 (m, 1H), 5.20 (m, 2H), 4.59 (d, 2H), 4.57 (s, 2H).

Example 7

6-allyl-N-[4-(pyridin-4-yl)phenyl]-6H-pyrimido[5,4-c][2,1]benzothiazin-2-amine 5,5-dioxide The title compound was prepared as described in Example 3B, substituting 4-(pyridine-4-yl)aniline for 4-[2-(diethylamino)ethoxy]aniline. MS (ESI) m/e 442 (M+H)⁺. ¹H NMR (400 MHz, DMSO-d₆) δ ppm 9.74 (m, 3H), 8.95 (d, 1H), 8.35 (d, 2H), 8.12 (d, 2H), 7.92 (t, 1H), 7.70 (d, 1H), 7.62 (t, 2H), 6.80 (d, 2H), 5.90 (m, 1H), 5.25 (m, 2H), 4.71 (d, 1H).

Example 8

6-allyl-N-(1-methyl-1,2,3,4-tetrahydroquinolin-7-yl)-6H-pyrimido[5,4-c][2,1]benzothiazin-2-amine 5,5-dioxide The title compound was prepared as described in Example 3B, substituting 7-amino-1-methyl-1,2,3,4-tetrahydroquinoline for 4-[2-(diethylamino)ethoxy]aniline. MS (ESI) m/e 434 (M+H)⁺. ¹H NMR (400 MHz, DMSO-d₆) δ ppm 10.21 (s, 1H), 8.94 (s, 1H), 8.46 (d, 1H), 7.74 (t, 1H), 7.50 (d, 1H), 7.45 (t, 1H), 7.22 (br s, 1H), 6.97 (d, 1H), 6.89 (d, 1H), 5.87 (m, 1H), 5.21 (m, 2H), 4.58 (d, 2H), 3.22 (t, 2H), 2.90 (s, 3H), 2.68 (t, 2H), 1.90 (m, 2H).

Example 9

6-allyl-N-[4-(4-methylpiperidin-1-yl)phenyl]-6H-pyrimido[5,4-c][2,1]benzothiazin-2-amine 5,5-dioxide The title compound was prepared as described in Example 3B, substituting 4-(4-methylpiperidin-1-yl)aniline for 4-[2-(diethylamino)ethoxy]aniline. MS (ESI) m/e 462 (M+H)⁺. ¹H NMR (400 MHz, DMSO-d₆) δ ppm 10.55 (br s, 1H), 9.00 (s, 1H), 8.46 (d, 1H), 7.85 (br d, 2H), 7.76 (m, 1H), 7.49 (m, 4H), 5.87 (m, 1H), 5.22 (m, 2H), 4.60 (d, 2H), 3.62 (d, 4H), 1.85 (d, 2H), 1.69 (m, 1H), 1.47 (m, 2H), 1.00 (d, 3H).

Example 10

1-(4-{4-[(6-allyl-5,5-dioxido-6H-pyrimido[5,4-c][2,1]benzothiazin-2-yl)amino]phenyl}piperazin-1-yl)ethanone The title compound was prepared as described in Example 3B, substituting 1-[4-(4-amino-phenyl-piperazin-1-yl]-ethanone for 4-[2-(diethylamino)ethoxy]aniline. MS (ESI) m/e 491 (M+H)⁺. ¹H NMR (400 MHz, DMSO-d₆) δ ppm 10.31 (s, 1H), 8.93 (s, 1H), 8.43 (d, 1H), 7.72 (m, 3H), 7.49 (m, 2H), 7.05 (d, 2H), 5.86 (m, 1H), 5.23 (m, 2H), 4.58 (d, 2H), 3.61 (m, 4H), 3.17 (t, 2H), 3.10 (t, 2H), 2.05 (s, 3H).

Example 11

6-allyl-N-[4-(piperidin-1-yl)phenyl]-6H-pyrimido[5,4-c][2,1]benzothiazin-2-amine 5,5-dioxide The title compound was prepared as described in Example 3B substituting 4-piperidinoaniline for 4-[2-(diethylamino)ethoxy]aniline. MS (ESI) m/e 448 (M+H)⁺. ¹H NMR (400 MHz, DMSO-d₆) δ ppm 10.60 (br s, 1H), 9.01 (s, 1H), 8.46 (d, 1H), 7.87 (m, 2H), 7.76 (m, 1H), 7.50 (m, 4H), 5.87 (m, 1H), 5.23 (m, 2H), 4.60 (d, 2H), 3.43 (m, 4H), 1.83 (m, 4H), 1.63 (m, 2H).

Example 12

6-allyl-N-[2-(4-methylpiperazin-1-yl)phenyl]-6H-pyrimido[5,4-c][2,1]benzothiazin-2-amine 5,5-dioxide The title compound was prepared as described in Example 3B, substituting 2-(4-methylpiperazin-1-yl)aniline for 4-[2-(diethylamino)ethoxy]aniline. MS (ESI) m/e 463 (M+H)⁺. ¹H NMR (400 MHz, DMSO-d₆) δ ppm 9.84 (br s, 1H), 9.01 (s, 1H), 8.43 (d, 1H), 8.16 (d, 1H), 7.76 (t, 1H), 7.49 (m, 2H), 7.23 (m, 3H), 5.88 (m, 1H), 5.24 (m, 2H), 4.60 (d, 2H), 3.45 (m, 4H), 3.22 (m, 4H), 2.87 (s, 3H).

Example 13

6-allyl-N-(4-cyclohexylphenyl)-6H-pyrimido[5,4-c][2,1]benzothiazin-2-amine 5,5-dioxide The title compound was prepared as described in Example 3B, substituting 4-cyclohexylaniline for 4-[2-(diethylamino)ethoxy]aniline. MS (ESI) m/e 447 (M+H)⁺. ¹H NMR (400 MHz, DMSO-d₆) δ ppm 10.40 (s, 1H), 8.96 (s, 1H), 8.45 (d, 1H), 7.74 (m, 3H), 7.50 (m, 2H), 7.24 (d, 2H), 5.86 (m, 1H), 5.22 (m, 2H), 4.58 (d, 2H), 2.49 (m, 1H), 1.75 (m, 5H), 1.36 (m, 5H).

Example 14

6-allyl-N-[4-(1H-imidazo[4,5-c]pyridin-2-yl)phenyl]-6H-pyrimido[5,4-c][2,1]benzothiazin-2-amine 5,5-dioxide The title compound was prepared as described in Example 3B, substituting 4-(3H-imidazo[4,5-c]pyridine-2-yl)aniline for 4-[2-(diethylamino)ethoxy]aniline. MS (ESI) m/e 482 (M+H)⁺. ¹H NMR (400 MHz, DMSO-d₆) δ ppm 10.30 (br s, 1H), 9.78 (m, 2H), 9.02 (br d, 1H), 8.18 (d, 1H), 8.07 (d, 2H), 7.93 (t, 1H), 7.70 (d, 1H), 7.61 (t, 1H), 6.77 (d, 2H), 6.35 (br s, 1H), 5.92 (m, 1H), 5.27 (m, 2H), 4.73 (d, 2H).

Example 15

6-allyl-N-[2-methoxy-4-(4-methylpiperazin-1-yl)phenyl]-6H-pyrimido[5,4-c][2,1]benzothiazin-2-amine 5,5-dioxide The title compound was prepared as described in Example 3B, substituting 2-methoxy-4-(4-methylpiperazin-1-yl)aniline for 4-[2-(diethylamino)ethoxy]aniline. MS (ESI) m/e 493 (M+H)⁺. ¹H NMR (500 MHz, DMSO-d₆) δ ppm 9.89 (br s, 1H), 9.29 (s, 1H), 8.64 (br s, 1H), 7.71 (t, 1H), 7.50 (d, 2H), 7.41 (m, 1H), 6.75 (br s, 1H), 6.63 (br d, 1H), 5.58 (m, 1H), 5.20 (m, 2H), 4.57 (d, 2H), 3.90 (m, 2H), 3.81 (s, 3H), 3.55 (m, 2H), 3.18 (m, 2H), 3.01 (m, 2H), 2.89 (s, 3H).

Example 16

6-allyl-N-[4-(morpholin-4-yl)phenyl]-6H-pyrimido[5,4-c][2,1]benzothiazin-2-amine 5,5-dioxide The title compound was prepared as described in Example 3B, substituting 4-morpholinoaniline for 4-[2-(diethylamino)ethoxy]aniline. MS (ESI) m/e 450 (M+H)⁺. ¹H NMR (400 MHz, DMSO-d₆) δ ppm 10.28 (br s, 1H), 8.92 (s, 1H), 8.41 (br d, 1H), 7.71 (m, 3H), 7.48 (m, 2H), 7.01 (br d, 2H), 5.85 (m, 1H), 5.22 (m, 2H), 4.58 (d, 2H), 3.75 (m, 4H), 3.11 (m, 4H).

Example 17

6-allyl-N-(5,6,7,8-tetrahydronaphthalen-2-yl)-6H-pyrimido[5,4-c][2,1]benzothiazin-2-amine 5,5-dioxide The title compound was prepared as described in Example 3B, substituting 6-amino-1,2,3-tetrahydronaphthalene for 4-[2-(diethylamino)ethoxy]aniline. MS (ESI) m/e 419 (M+H)⁺. ¹H NMR (500 MHz, DMSO-d₆) δ ppm 10.31 (s, 1H), 8.95 (s, 1H), 8.41 (d, 1H), 7.73 (t, 1H), 7.51 (m, 4H), 7.07 (d, 1H), 5.86 (m, 1H), 5.22 (m, 2H), 4.58 (d, 2H), 2.72 (m, 4H), 1.75 (m, 4H).

Example 18

6-allyl-N-[3-(4-methylpiperazin-1-yl)phenyl]-6H-pyrimido[5,4-c][2,1]benzothiazin-2-amine 5,5-dioxide The title compound was prepared as described in Example 3B, substituting 3-(4-methylpiperazin-1-yl)aniline for 4-[2-

(diethylamino)ethoxy]aniline. MS (ESI) m/e 463 (M+H)+. $^1$H NMR (400 MHz, DMSO-d$_6$) δ ppm 10.41 (s, 1H), 9.00 (s, 1H), 8.46 (d, 1H), 7.76 (t, 1H), 7.51 (m, 3H), 7.29 (m, 2H), 6.80 (m, 1H), 5.87 (m, 1H), 5.23 (m, 2H), 4.61 (br d, 2H), 3.85 (br d, 2H), 3.52 (m, 2H), 3.21 (m, 2H), 3.05 (m, 2H), 2.90 (s, 3H).

Example 19

6-allyl-N-[4-(1-methylpiperidin-4-yl)phenyl]-6H-pyrimido[5,4-c][2,1]benzothiazin-2-amine 5,5-dioxide The title compound was prepared as described in Example 3B, substituting 4-(1-methylpiperadin-4-yl)aniline for 4-[2-(diethylamino)ethoxy]aniline. MS (ESI) m/e 462 (M+H)+. $^1$H NMR (400 MHz, DMSO-d$_6$) δ ppm 10.47 (br s, 1H), 8.98 (s, 1H), 8.46 (d, 1H), 7.76 (m, 3H), 7.50 (m, 2H), 7.27 (d, 2H), 5.86 (m, 1H), 5.22 (m, 2H), 4.59 (br d, 2H), 3.53 (m, 2H), 3.08 (m, 2H), 2.80 (m, 4H), 2.04 (m, 2H), 1.85 (m, 2H).

Example 20

6-allyl-N-[4-(1H-benzimidazol-2-yl)phenyl]-6H-pyrimido[5,4-c][2,1]benzothiazin-2-amine 5,5-dioxide The title compound was prepared as described in Example 3B, substituting 4-(1H-benzo[d]imidazol-2-yl)aniline for 4-[2-(diethylamino)ethoxy]aniline. MS (ESI) m/e 481 (M+H)+. $^1$H NMR (500 MHz, DMSO-d$_6$) δ ppm 10.28 (br s, 1H), 9.09 (s, 1H), 8.53 (d, 1H), 8.23 (d, 2H), 8.10 (d, 2H), 7.79 (t, 1H), 7.69 (m, 2H), 7.58 (m, 2H), 7.53 (m, 2H), 5.86 (m, 1H), 5.21 (m, 2H), 4.60 (d, 2H).

Example 21

6-allyl-N-[4-(1-methyl-1H-benzimidazol-2-yl)phenyl]-6H-pyrimido[5,4-c][2,1]benzothiazin-2-amine 5,5-dioxide The title compound was prepared as described in Example 3B, substituting 4-1-methyl-1H-benzo[d]imidazol-2-yl)aniline for 4-[2-(diethylamino)ethoxy]aniline. MS (ESI) m/e 495 (M+H)+. $^1$H NMR (400 MHz, DMSO-d$_6$) δ ppm 10.95 (s, 1H), 9.12 (s, 1H), 8.56 (d, 1H), 8.18 (d, 2H), 8.00 (d, 2H), 7.93 (d, 1H), 7.81 (m, 2H), 7.54 (m, 4H), 5.88 (m, 1H), 5.24 (m, 2H), 4.62 (d, 2H), 4.05 (s, 3H).

Example 22

6-allyl-N-(2,4,4-trimethyl-1,2,3,4-tetrahydroisoquinolin-7-yl)-6H-pyrimido[5,4-c][2,1]benzothiazin-2-amine 5,5-dioxide The title compound was prepared as described in Example 3B, substituting 2,4,4-trimethyl-1,2,3,4-tetrahydroisoquinolin-7-amine (prepared as described in WO2005/023807) for 4-[2-(diethylamino)ethoxy]aniline. MS (ESI) m/e 462 (M+H)+. $^1$H NMR (400 MHz, DMSO-d$_6$) δ 10.56 (s, 1H), 9.00 (s, 1H), 8.45 (d, 1H), 7.77 (m, 2H), 7.54 (m, 4H), 5.85 (m, 1H), 5.23 (m, 2H), 4.60 (d, 2H), 4.45 (m, 2H), 3.27 (m, 2H), 3.01 (s, 3H), 1.41 (s, 3H), 1.36 (s, 3H).

Example 23

6-allyl-N-[4-(pyrimidin-2-yl)phenyl]-6H-pyrimido[5,4-c][2,1]benzothiazin-2-amine 5,5-dioxide The title compound was prepared as described in Example 3B, substituting 4-pyrimidin-2-ylaniline for 4-[2-(diethylamino)ethoxy]aniline. MS (ESI) m/e 443 (M+H)+. $^1$H NMR (400 MHz, DMSO-d$_6$) δ 10.78 (s, 1H), 9.07 (s, 1H), 8.88 (d, 2H), 8.54 (d, 1H), 8.45 (d, 2H), 8.03 (d, 2H), 7.77 (m, 1H), 7.55 (m, 2H), 7.40 (t, 1H), 5.88 (m, 1H), 5.23 (m, 2H), 4.61 (d, 2H).

Example 24

6-allyl-N-phenyl-6H-pyrimido[5,4-c][2,1]benzothiazin-2-amine 5,5-dioxide

The title compound was prepared as described in Example 3B, substituting aniline for 4-[2-(diethylamino)ethoxy]aniline. MS (ESI) m/e 365 (M+H)+. $^1$H NMR (400 MHz, DMSO-d$_6$) δ ppm 10.48 (s, 1H), 8.99 (s, 1H), 8.46 (d, 1H), 7.83 (d, 2H), 7.75 (m, 1H), 7.51 (m, 2H), 7.41 (t, 2H), 7.11 (t, 1H), 5.85 (m, 1H), 5.23 (m, 2H), 4.60 (d, 2H).

Example 25

6-allyl-N-[4-(piperazin-1-yl)phenyl]-6H-pyrimido[5,4-c][2,1]benzothiazin-2-amine 5,5-dioxide A solution of Example 3A (64.8 mg, 0.19 mmol) and 4-(4-aminophenyl)piperazine-1-carboxylic acid tert-butyl ester (67 mg, 0.24 mmol) was stirred in 2 mL acetonitrile for 24 hours. The reaction mixture was concentrated and dissolved in 2 mL 1:1 dichloromethane:trifluoroacetic acid. After 4 hours, the solution was concentrated and the crude reaction mixture was purified as described in Example 3B to afford the title compound. MS (ESI) m/e 449 (M+H)+. $^1$H NMR (500 MHz, DMSO-d$_6$) δ ppm 10.33 (br s, 1H), 8.93 (s, 1H), 8.43 (d, 1H), 7.73 (m, 3H), 7.53 (d, 1H), 7.46 (t, 1H), 7.05 (br d, 2H), 5.86 (m, 1H), 5.23 (m, 2H), 4.58 (d, 2H), 3.30 (m, 8H).

Example 26

6-allyl-N-(1,2,3,4-tetrahydroisoquinolin-7-yl)-6H-pyrimdio[5,4-c][2,1]benzothiazin-2-amine 5,5-dioxide The title compound was prepared as described in Example 25 substituting tert-butyl 7-amino-3,4-dihydroisoquinoline-2(1H)carboxylate for 4-(4-aminophenyl)piperazine-1-carboxylic acid tert-butyl ester. MS (ESI) m/e 420 (M+H)+. $^1$H NMR (500 MHz, DMSO-d$_6$) δ ppm 10.53 (s, 1H), 8.99 (s, 1H), 8.44 (d, 1H), 7.76 (m, 1H), 7.68 (br s, 2H), 7.55 (d, 1H), 7.47 (t, 1H), 7.26 (d, 1H), 5.86 (m, 1H), 5.23 (m, 2H), 4.59 (d, 2H), 4.34 (br s, 2H), 3.43 (m, 2H), 2.99 (t, 2H).

Example 27

6-allyl-N-(pyridin-4-yl)-6H-pyrimido[5,4-c][2,1]benzothiazin-2-amine 5,5-dioxide The title compound was prepared as described in Example 3B, substituting pyridine-4-amine for 4-[2-(diethylamino)ethoxy]aniline. MS (ESI) m/e 366 (M+H)+. $^1$H NMR (500 MHz, DMSO-d$_6$) δ ppm 11.85 (s, 1H), 9.30 (s, 1H), 8.72 (d, 2H), 8.59 (d, 1H), 8.30 (d, 2H), 7.83 (t, 1H), 7.61 (d, 1H), 7.54 (t, 1H), 5.89 (m, 1H), 5.24 (m 2H), 4.64 (d, 2H).

Example 28

6-allyl-N-(2'-methyl-2',3'-dihydro-1'H-spiro[cyclopropane-1,4'-isoquinolin]-7'-yl)-6H-pyrimido[5,4-c][2,1]benzothiazin-2-amine 5,5-dioxide The title compound was prepared as described in Example 3B substituting 2'-methyl-2',3'-dihydro-1'H-spiro[cyclopropane-1,4'-isoquinolin]-6'-amine (prepared as described in WO2009/151997) for 4-[2-(diethylamino)ethoxy]aniline. MS (ESI) m/e 460 (M+H)$^+$. $^1$H NMR (400 MHz, DMSO-d$_6$, 90° C.) δ ppm 10.20 (br s, 1H), 8.91 (s, 1H), 8.44 (d, 1H), 7.72 (m, 3H), 7.46 (m, 2H), 6.90 (d, 1H), 5.85 (m, 1H), 5.20 (m, 2H), 4.56 (m, 4H), 3.69 (m, 2H), 2.97 (s, 3H), 1.14 (m, 4H).

Example 29

6-allyl-6H-pyrimido[5,4-c][2,1]benzothiazin-2-amine 5,5-dioxide

The title compound was prepared as described in Example 3B, substituting 2M ammonia in dioxane for 4-[2-(diethylamino)ethoxy]aniline. MS (ESI) m/e 289 (M+H)$^+$. $^1$H NMR (400 MHz, DMSO-d$_6$) δ ppm 8.76 (s, 1H), 8.38 (d, 1H), 7.74 (br s, 2H), 7.70 (m, 1H), 7.43 (m, 2H), 5.84 (m, 1H), 5.20 (m, 2H), 4.55 (d, 2H).

Example 30

6-allyl-N-(1,2,3,4-tetrahydroquinolin-7-yl)-6H-pyrimido[5,4-c][2,1]benzothiazin-2-amine 5,5-dioxide The title compound was prepared as described in Example 25, substituting tert-butyl-7-amino-3,4-dihydroquinoline-1(2H)-carboxylate for 4-(4-aminophenyl)piperazine-1-carboxylic acid tert-butyl ester. MS (ESI) m/e 420 (M+H)$^+$. $^1$H NMR (500 MHz, DMSO-d$_6$) δ ppm 10.39 (s, 1H), 8.96 (s, 1H), 8.50 (d, 1H), 7.76 (t, 1H), 7.50 (m, 3H), 7.20 (m, 1H), 7.04 (d, 1H), 5.84 (m, 1H), 5.23 (m, 2H), 4.59 (d, 2H), 3.30 (m, 2H), 2.72 (m, 2H), 1.89 (m, 2H).

Example 31

6-allyl-N-[3-fluoro-4-(piperazin-1-yl)phenyl]-6H-pyrimido[5,4-c][2,1]benzothiazin-2-amine 5,5-dioxide The title compound was prepared as described in Example 25, substituting tert-butyl 4-(4-amino-2-fluorophenyl)tetrahydro-1(2H)-pyrazinecarboxylate for 4-(4-aminophenyl)piperazine-1-carboxylic acid tert-butyl ester. MS (ESI) m/e 467 (M+H)$^+$. $^1$H NMR (400 MHz, DMSO-d$_6$) δ ppm 10.55 (s, 1H), 9.01 (s, 1H), 8.43 (d, 1H), 7.76 (m, 2H), 7.52 (m, 3H), 7.17 (br t, 1H), 5.87 (m, 1H), 5.22 (m, 2H), 4.59 (d, 2H), 3.29 (m, 4H), 3.21 (m, 4H).

Example 32

6-allyl-N-phenyl-6H-pyrido[2,3-c]pyrimido[4,5-e][1,2]thiazin-2-amine 5,5-dioxide Example 32A methyl 2-[(methylsulfonyl)amino]nicotinate Methyl 2-aminonicotinate (2.05 g, 13.5 mmol), methanesulfonic anhydride (7 g, 40 mmol), and pyridine (4.5 mL, 56 mmol) were stirred in 20 mL 1,2-dichloroethane at 70° C. for 24 hours. The reaction mixture was concentrated and purified on silica gel (1:1 ethyl acetate:hexanes) to afford the title compound. MS (ESI) m/e 231 (M+H)$^+$. $^1$H NMR (400 MHz, DMSO-d$_6$) δ ppm 10.20 (br s, 1H), 8.57 (m, 1H), 8.33 (m, 1H), 7.24 (q, 1H), 3.91 (s, 3H), 3.48 (s, 3H).

Example 32B methyl 2-[allyl(methylsulfonyl)amino]nicotinate

The title compound was prepared as described in Example 1B, substituting Example 32A for Example 1A. MS (ESI) m/e 270 (M+H)$^+$. $^1$H NMR (400 MHz, DMSO-d$_6$) δ ppm 8.68 (m, 1H), 8.19 (dd, 1H), 7.52 (m, 1H), 5.86 (m, 1H), 5.22 (m, 1H), 5.03 (m, 1H), 4.42 (d, 2H), 3.82 (s, 3H), 3.06 (s, 3H).

Example 32C 1-allyl-1H-pyrido[2,3-c][1,2]thiazin-4(3H)-one 2,2-dioxide

The title compound was prepared as described in Example 1C, substituting Example 32B for Example 1B. MS (ESI) m/e 239 (M+H)$^+$. $^1$H NMR (400 MHz, DMSO-d$_6$) δ ppm 8.69 (m, 1H), 8.36 (dd, 1H), 7.34 (m, 1H), 6.01 (m, 1H), 5.33 (m, 1H), 5.18 (m, 1H), 5.10 (s, 2H), 4.72 (m, 2H).

Example 32D 6-allyl-2-(methylthio)-6H-pyrido[2,3-c]pyrimido[4,5-e][1,2]thiazine 5,5-dioxide The title compound was prepared as described in Example 1E, substituting Example 32C for Example 1C. MS (ESI) m/e 321 (M+H)$^+$. $^1$H NMR (500 MHz, DMSO-d$_6$) δ ppm 9.26 (s, 1H), 8.96 (dd, 1H), 8.78 (m, 1H), 7.54 (m, 1H), 5.03 (m, 1H), 5.20 (m, 2H), 4.81 (d, 2H), 2.71 (s, 3H).

Example 32E 6-allyl-2-(methylsulfonyl)-6H-pyrido[2,3-c]pyrimido[4,5-e][1,2]thiazine 5,5-dioxide To a solution of Example 32D in 200 mL methanol was added potassium peroxysulfate in 200 mL of water. After stirring at room temperature for 24 hours, the reaction was concentrated and partitioned between ethyl acetate/water. The layers were separated, and the organic phase was dried over magnesium sulfate, filtered and concentrated to afford the title compound. $^1$H NMR (400 MHz, DMSO-d$_6$) δ ppm 9.77 (s, 1H), 9.08 (dd, 1H), 8.87 (m, 1H), 7.63 (m, 1H), 6.06 (m, 1H), 5.23 (m, 2H), 4.86 (d, 2H), 3.59 (s, 3H).

Example 32F 6-allyl-N-phenyl-6H-pyrido[2,3-c]pyrimido[4,5-e][1,2]thiazin-2-amine 5,5-dioxide The title compound was prepared as described in Example 3B, substituting Example 32E for Example 3A, and substituting aniline for 4-[2-(diethylamino)ethoxy]aniline. MS (ESI) m/e 366 (M+H)$^+$. $^1$H NMR (500 MHz, DMSO-d$_6$) δ ppm 10.59 (s, 1H), 9.10 (s, 1H), 8.82 (dd, 1H), 8.74 (m, 1H), 7.82 (br d, 2H), 7.53 (m, 1H), 7.41 (t, 2H), 7.12 (t, 1H), 6.03 (m, 1H), 5.18 (m, 2H), 4.80 (d, 2H).

Example 33

6-allyl-N-(1,2,3,4-tetrahydroisoquinolin-7-yl)-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl-7-amino-3,4-dihydroisoquinoline-2(1H)-carboxylate for 4-(4-aminophenyl)piperazine-1-carboxylic acid tert-butyl ester. MS (ESI) m/e 421 (M+H)$^+$. $^1$H NMR (500 MHz, DMSO-d$_6$) δ ppm 10.63 (s, 1H), 9.09 (s, 1H), 8.80 (dd, 1H), 8.75 (m, 1H), 7.86 (br s, 2H), 7.51 (m, 1H), 7.26 (d, 1H), 6.03 (m, 1H), 5.18 (m, 2H), 4.81 (d, 2H), 4.35 (br s, 2H), 3.43 (m, 2H), 3.00 (t, 2H).

Example 34

6-allyl-N-[4-(piperazin-1-yl)phenyl]-6H-pyrido[2,3-c]pyrimido[4,5-e][1,2]thiazin-2-amine 5,5-dioxide The title compound was prepared as described in Example 25, substituting Example 32E for Example 3A. MS (ESI) m/e 450 (M+H)$^+$. $^1$H NMR (500 MHz, DMSO-d$_6$) δ ppm 10.44 (br s, 1H), 9.03 (s, 1H), 8.74 (m, 2H), 7.51 (m, 3H), 7.06 (br d, 2H), 6.02 (m, 1H), 5.18 (m, 2H), 4.79 (d, 2H), 3.25 (m, 8H).

Example 35

1-{6-[(6-allyl-5,5-dioxido-6H-pyrido[2,3-c]pyrimido[4,5-e][1,2]thiazin-2-yl)amino]-2,3-dihydro-1H-indol-1-yl}ethanone The title compound was prepared as described in Example 3B, substituting Example 32E for Example 3A, and substituting 1-acetyl-6-aminoindole for 4-[2-(diethylamino)ethoxy]aniline. MS (ESI) m/e 449 (M+H)$^+$. $^1$H NMR (400 MHz, DMSO-d$_6$, 90° C.) δ ppm 10.22 (s, 1H), 9.11 (br d, 1H), 8.97 (s, 1H), 8.82 (br s, 1H), 8.68 (m, 1H), 7.43 (m, 1H), 7.28 (m, 1H), 7.19 (d, 1H), 6.01 (m, 1H), 5.20 (m, 2H), 4.81 (m, 2H), 4.13 (t, 2H), 3.12 (t, 2H), 2.21 (s, 3H).

Example 36

6-allyl-N-[3-fluoro-4-(piperazin-1-yl)phenyl]-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl-4-(4-amino-fluorophenyl)tetrahydro-1(2H)-pyrazine carboxylate for 4-(4-aminophenyl)piperazine-1-carboxylic acid tert-butyl ester. MS (ESI) m/e 468 (M+H)$^+$. $^1$H NMR (400 MHz, DMSO-d$_6$) δ ppm 10.66 (br s, 1H), 9.11 (s, 1H), 8.78 (m, 2H), 7.60 (m, 3H), 7.17 (br t, 1H), 6.03 (m, 1H), 5.20 (m, 2H), 4.80 (d, 2H), 3.43 (m, 4H), 3.25 (m, 4H).

Example 37

6-allyl-N-[4-(piperidin-4-yl)phenyl]-6H-pyrido[2,3-c]pyrimido[4,5-e][1,2]thiazin-2-amine 5,5-dioxide The title compound was prepared as described in Example 25, substituting Example 32E for Example 3A, and substituting 4-(4-amino-phenyl)-piperidine-1-carboxylic acid tert-butyl ester for 4-(4-aminophenyl)piperazine-1-carboxylic acid tert-butyl ester. MS (ESI) m/e 449 (M+H)$^+$. $^1$H NMR (400 MHz, DMSO-d$_6$) δ ppm 10.58 (br s, 1H), 9.08 (s, 1H), 8.82 (m, 1H), 8.74 (m, 1H), 8.46 (m, 1H), 7.78 (m, 2H), 7.52 (m, 1H), 7.27 (d, 2H), 6.03 (m, 1H), 5.20 (m, 2H), 4.80 (d, 2H), 3.39 (m, 2H), 3.03 (m, 2H), 2.68 (m, 1H), 1.97 (m, 2H), 1.81 (m, 2H).

Example 38

6-allyl-N-(1,2,3,4-tetrahydroquinolin-7-yl)-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl-7-amino-3,4-dihydroquinoline-1(2H)-carboxylate for 4-(4-aminophenyl)piperazine-1-carboxylic acid tert-butyl ester. MS (ESI) m/e 421 (M+H)$^+$. $^1$H NMR (400 MHz, DMSO-d$_6$) δ 10.41 (s, 1H), 9.05 (s, 1H), 8.85 (d, 1H), 8.75 (m, 1H), 7.52 (m, 1H), 7.50 (m, 1H), 7.05 (m, 1H), 6.97 (m, 1H), 6.03 (m, 1H), 5.17 (m, 2H), 4.91 (d, 2H), 3.26 (m, 2H), 2.70 (t, 2H), 1.86 (t, 2H).

Example 39

6-allyl-N-{4-[2-(diethylamino)ethoxy]phenyl}-6H-pyrido[2,3-c]pyrimido[4,5-e][1,2]thiazin-2-amine 5,5-dioxide The title compound was prepared as described in Example 3B substituting Example 32E for Example 3A. MS (ESI) m/e 481(M+H)$^+$. $^1$H NMR (400 MHz, DMSO-d$_6$) δ ppm 10.14 (s, 1H), 8.97 (s, 1H), 8.76 (m, 1H), 8.70 (m, 1H), 7.71 (d, 2H), 7.45 (m, 1H), 7.04 (d, 2H), 6.00 (m, 1H), 5.20 (m, 2H), 4.80 (m, 2H), 4.33 (t, 2H), 3.49 (m, 2H), 3.24 (m, 4H), 1.26 (t, 6H).

Example 40

6-allyl-N-[4-(4-methylpiperazin-1-yl)phenyl]-6H-pyrido[2,3-c]pyrimido[4,5-e][1,2]thiazin-2-amine 5,5-dioxide The title compound was prepared as described in Example 3B, substituting Example 32E for Example 3A, and substituting 4-(4-methylpiperzino)aniline for 4-[2-(diethylamino)ethoxy]aniline. MS (ESI) m/e 464 (M+H)$^+$. $^1$H NMR (400 MHz, DMSO-d$_6$) δ ppm 10.44 (br s, 1H), 9.04 (s, 1H), 8.75 (m, 2H), 7.70 (m, 2H), 7.50 (m, 1H), 7.06 (br d, 2H), 6.02 (m, 1H), 5.19 (m, 2H), 4.79 (d, 2H), 3.35 (m, 4H), 2.85 (s, 3H), 2.52 (m, 4H).

Example 41

6-allyl-N-[3-chloro-4-(4-methylpiperazin-1-yl)phenyl]-6H-pyrido[2,3-c]pyrimido[4,5-e][1,2]thiazin-2-amine 5,5-dioxide The title compound was prepared as described in Example 3B, substituting Example 32E for Example 3A, and substituting 3-chloro-4-(4-methylpiperazin-yl)aniline for 4-[2-(diethylamino)ethoxy]aniline. $^1$H NMR (400 MHz, DMSO-d$_6$) δ ppm 9.70 (br s, 1H), 9.17 (s, 1H), 8.77 (d, 2H), 7.83 (m, 1H), 7.60 (dd, 1H), 7.50 (m, 1H), 7.39 (d, 1H), 6.04 (m, 1H), 5.23 (m, 2H), 4.76 (d, 2H), 3.54 (m, 4H), 3.26 (m, 2H), 3.10 (m, 2H), 2.90 (s, 3H).

Example 42

6-allyl-N-[3-methyl-4-(piperazin-1-yl)phenyl]-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl 4-(4-amino-2-methylphenyl)piperazine-1-carboxylate for 4-(4-aminophenyl)piperazine-1-carboxylic acid tert-butyl ester. MS (ESI) m/e 464 (M+H)$^+$. $^1$H NMR (400 MHz, DMSO-d$_6$, 90° C.) δ ppm 10.29 (s, 1H), 9.15 (s, 1H), 8.94 (dd, 1H), 8.88 (m, 1H), 7.80 (m, 2H), 7.65 (m, 1H), 7.27 (d, 1H), 6.19 (m, 1H), 5.35 (m, 2H), 4.98 (d, 2H), 3.44 (m, 4H), 3.25 (m, 4H), 2.49 (s, 3H).

Example 43

{4-[(6-allyl-5,5-dioxido-6H-pyrido[2,3-c]pyrimido[4,5-e][1,2]thiazin-2-yl)amino]phenyl}(4-methylpiperazin-1-yl)methanone The title compound was prepared as described in Example 3B, substituting Example 32E for Example 3A, and substituting (4-aminophenyl)(4-methylpiperazin-1-yl)methanone for 4-[2-(diethylamino)ethoxy]aniline. MS (ESI) m/e 492 (M+H)$^+$. $^1$H NMR (400 MHz, DMSO-d$_6$) δ ppm 10.85 (s, 1H), 9.16 (s, 1H), 8.86 (dd, 1H), 8.76 (dd, 1H), 7.95 (d, 2H), 7.53 (m, 3H), 6.05 (m, 1H), 5.21 (m, 2H), 4.81 (d, 2H), 3.36 (m, 4H), 3.20 (m, 4H), 2.83 (s, 3H).

Example 44

6-allyl-N-[2-methyl-4-(4-methylpiperazin-1-yl)phenyl]-6H-pyrido[2,3-c]pyrimido[4,5-e][1,2]thiazin-2-amine 5,5-dioxide The title compound was prepared as described in Example 3B, substituting Example 32E for Example 3A, and substituting 2-methyl-4-(4-methylpiperazin-1-yl)aniline for 4-[2-(diethylamino)ethoxy]aniline. MS (ESI) m/e 478 (M+H)$^+$. $^1$H NMR (400 MHz, DMSO-d$_6$, 90° C.) δ ppm 9.51 (s, 1H), 8.87 (s, 1H), 8.65 (dd, 1H), 8.59 (br d, 1H), 7.39 (m, 1H), 7.29 (d, 1H), 6.88 (m, 2H), 5.99 (m, 1H), 5.20 (m, 2H), 7.48 (d, 2H), 3.43 (m, 4H), 3.30 (m, 4H), 2.84 (s, 3H), 2.21 (s, 3H).

Example 45

6-allyl-N-[4-(pyrrolidin-3-yl)phenyl]-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl 3-(4-aminophenyl)pyrrolidine-1-carboxylate for 4-(4-aminophenyl)piperazine-1-carboxylic acid tert-butyl ester. MS (ESI) m/e 435 (M+H)$^+$. $^1$H NMR (400 MHz, DMSO-d$_6$) δ ppm 10.61 (s, 1H), 9.10 (s, 1H), 8.81 (dd, 1H), 8.75 (dd, 1H), 7.80 (br d, 2H), 7.52 (m, 1H), 7.38 (d, 2H), 6.03 (m, 1H), 5.20 (m, 2H), 4.60 (d, 2H), 3.64 (m, 1H), 3.44 (m, 1H), 3.25 (m, 1H), 3.09 (t, 2H), 2.38 (m, 1H), 1.97 (m, 1H).

Example 46

6-allyl-N-(1,2,3,4-tetrahydroisoquinolin-6-yl)-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl 6-amino-3,4-dihydroisoquinoline-2(1H)-carboxylate for 4-(4-aminophenyl)piperazine-1-carboxylic acid tert-butyl ester. MS (ESI) m/e 421 (M+H)$^+$. $^1$H NMR (500 MHz, DMSO-d$_6$) δ ppm 10.63 (s, 1H), 9.11 (s, 1H), 8.78 (m, 2H), 7.68 (br s, 2H), 7.53 (m, 1H), 7.26 (d, 1H), 6.03 (m, 1H), 5.20 (m, 2H), 4.80 (d, 2H), 4.27 (s, 2H), 3.42 (t, 2H), 3.05 (br t, 2H).

Example 47

6-allyl-N-(2'-methyl-2',3'-dihydro-1'H-spiro[cyclopropane-1,4'-isoquinolin]-7'-yl)-6H-pyrido[2,3-c]pyrimido[4,5-e][1,2]thiazin-2-amine 5,5-dioxide The title compound was prepared as described in Example 3B, substituting Example 32E for Example 3A, and substituting 2'-methyl-2',3'-dihydro-1'H-spiro[cyclopropane-1,4'-isoquinolin]-7'-amine (prepared as described in WO2009/151997) for 4-[2-(diethylamino)ethoxy]aniline. MS (ESI) m/e 461 (M+H)$^+$. $^1$H NMR (400 MHz, DMSO-d$_6$, 90° C.) δ ppm 10.30 (s, 1H), 9.00 (s, 1H), 8.77 (dd, 1H), 8.71 (m, 1H), 7.70 dd, 1H), 7.60 (br d, 1H), 7.48 (m, 1H), 6.81 (d, 1H), 6.00 (m, 1H), 5.20 (m, 2H), 4.80 (d, 2H), 4.52 (br s, 2H), 3.37 (br s, 2H), 2.95 (s, 3H), 1.14 (m, 4H).

Example 48

6-allyl-N-[4-(hexahydropyrrolo[1,2-a]pyrazin-2(1H)-yl)phenyl]-6H-pyrido[2,3-c]pyrimido[4,5-e][1,2]thiazin-2-amine 5,5-dioxide

Example 48A 2-(4-nitrophenyl)octahydropyrrolo[1,2-a]pyrazine

Octahydropyrrolo[1,2-A]pyrazine (497 mg, 4 mmol), 4-fluoronitrobenzene (561 mg, 4 mmol) and potassium carbonate (1.14 g, 8.2 mmol) were stirred in 5 mL N,N-dimethylformamide for 24 hours. The reaction mixture was partitioned between ethyl acetate and water. The organic phase was dried over magnesium sulfate, filtered and concentrated to afford the title compound which was used in the next step without further purification. MS (ESI) m/e 248 (M+H)$^+$. $^1$H NMR (300 MHz, DMSO-d$_6$) δ 8.04 (d, 2H), 7.05 (d, 2H), 4.14 (m, 1H), 3.98 (m, 1H), 3.04 (m, 3H), 2.66 (m, 1H), 1.95 (m, 6H), 1.36 (m, 1H).

Example 48B 4-(hexahydropyrrolo[1,2-a]pyrazin-2(1H)-yl)aniline

Example 48A (960 mg, 3.9 mmol) and 10% palladium on carbon (96 mg) in 40 mL absolute ethanol were stirred vigorously under a H$_2$ balloon for 4 hours. The reaction was filtered through diatomaceous earth and the filtrate was concentrated to afford the title compound. MS (ESI) m/e 218 (M+H)$^+$. $^1$H NMR (300 MHz, DMSO-d$_6$) δ ppm 6.68 (d, 2H), 6.45 (d, 2H), 4.52 (br s, 2H), 3.42 (m, 1H), 3.27 (m, 1H), 2.99 (m, 2H), 2.59 (m, 1H), 2.25 (m, 2H), 2.04 (m, 2H), 1.72 (m, 3H), 1.35 (m, 1H).

Example 48C 6-allyl-N-[4-(hexahydropyrrolo[1,2-a]pyrazin-2(1H)-yl)phenyl]-6H-pyrido[2,3-c]pyrimido[4,5-e][1,2]thiazin-2-amine 5,5-dioxide The title compound was prepared as described in Example 3B, substituting Example 32E for Example 3A, and substituting Example 48B for 4-[2-(diethylamino)ethoxy]aniline. MS (ESI) m/e 490 (M+H)+. $^1$H NMR (400 MHz, DMSO-d$_6$, 90° C.) δ ppm 10.08 (s, 1H), 8.94 (s, 1H), 8.76 (dd, 1H), 8.69 (dd, 1H), 7.66 d, 2H), 7.45 (m, 1H), 7.03 (d, 2H), 6.01 (m, 1H), 5.20 (m, 2H), 4.81 (d, 2H), 3.30 (m, 8H), 2.10 (m, 4H), 1.82 (m, 1H).

Example 49

6-allyl-N-(1-methyl-1,2,3,4-tetrahydroquinolin-7-yl)-6H-pyrido[2,3-c]pyrimido[4,5-e][1,2]thiazin-2-amine 5,5-dioxide The title compound was prepared as described in Example 3B, substituting Example 32E for Example 3A, and substituting 7-amino-1-methyl-1,2,3,4-tetrahydroquinoline for 4-[2-(diethylamino)ethoxy]aniline. MS (ESI) m/e 435 (M+H)+. $^1$H NMR (400 MHz, DMSO-d$_6$) δ ppm 10.30 (br s, 1H), 9.04 (s, 1H), 8.79 (m, 1H), 8.72 (m, 1H), 7.51 (m, 1H), 7.18 (m, 1H), 6.99 (dd, 1H), 6.89 (d, 1H), 6.01 (m, 1H), 5.18 (m, 2H), 4.79 (d, 2H), 3.21 (t, 2H), 2.88 (s, 3H), 2.68 (t, 2H), 1.90 (t, 2H).

Example 50

6-allyl-N-[3-methyl-4-(4-methylpiperazin-1-yl)phenyl]-6H-pyrido[2,3-c]pyrimido[4,5-e][1,2]thiazin-2-amine 5,5-dioxide The title compound was prepared as described in Example 3B, substituting Example 32E for Example 3A, and substituting 3-methyl-4-(4-methylpiperazin-1-yl)aniline for 4-[2-(diethylamino)ethoxy]aniline. MS (ESI) m/e 478.2 (M+H)+. $^1$H NMR (400 MHz, DMSO-d$_6$) δ ppm 10.48 (br s, 1H), 9.06 (s, 1H), 8.78 (m, 2H), 7.54 (m, 3H), 7.13 (br s, 1H), 6.03 (m, 1H), 5.20 (m, 2H), 4.80 (d, 2H), 3.52 (m, 2H), 3.22 (m, 4H), 2.96 (m, 2H), 2.90 (s, 3H), 2.31 (s, 3H).

Example 51

6-allyl-N-[4-(piperazin-1-yl)-3-(trifluoromethyl) phenyl]-6H-pyrido[2,3-c]pyrimido[4,5-e][1,2]thiazin-2-amine 5,5-dioxide The title compound was prepared as described in Example 25, substituting Example 32E for Example 3A, and substituting tert-butyl 4-(4-amino-2-(trifluoromethyl)phenyl)piperazine-1-carboxylate for 4-(4-aminophenyl)piperazine-1-carboxylic acid tert-butyl ester. MS (ESI) m/e 518 (M+H)+. $^1$H NMR (400 MHz, DMSO-d$_6$) δ ppm 10.86 (s, 1H), 9.16 (s, 1H), 8.79 (m, 2H), 8.31 (m, 1H), 8.12 (br d, 1H), 7.62 (d, 1H), 7.53 (m, 1H), 6.04 (m, 1H), 5.21 (m, 2H), 4.81 (d, 2H), 3.23 (m, 4H), 3.06 (m, 4H).

Example 52

6-allyl-N-[4-(morpholin-4-yl)phenyl]-6H-pyrido[2,3-c]pyrimido[4,5-e][1,2]thiazin-2-amine 5,5-dioxide The title compound was prepared as described in Example 25, substituting Example 32E for Example 3A, and substituting 4-morpholinoaniline for 4-(4-aminophenyl)piperazine-1-carboxylic acid tert-butyl ester. MS (ESI) m/e 451 (M+H)+. $^1$H NMR (500 MHz, DMSO-d$_6$) δ ppm 10.39 (br s, 1H), 9.02 (s, 1H), 8.78 (br d, 1H), 8.73 (m, 1H), 7.52 (m, 3H), 6.99 (m, 2H), 6.02 (m, 1H), 5.20 (m, 2H), 4.79 (d, 2H), 3.75 (m, 4H), 3.10 (4H).

Example 53

6-allyl-N-[3-methyl-4-(4-methyl-1,4-diazepan-1-yl) phenyl]-6H-pyrido[2,3-c]pyrimido[4,5-e][1,2]thiazin-2-amine 5,5-dioxide The title compound was prepared as described in Example 25, substituting Example 32E for Example 3A, and substituting 3-methyl-4-(4-methyl-1,4-diazepan-1-yl)aniline for 4-(4-aminophenyl)piperazine-1-carboxylic acid tert-butyl ester. MS (ESI) m/e 492 (M+H)+. $^1$H NMR (400 MHz, DMSO-d$_6$, 90° C.) δ ppm 10.10 (s, 1H), 8.97 (s, 1H), 8.76 (dd, 1H), 8.69 (dd, 1H), 7.59 (m, 2H), 7.47 (dd, 1H), 7.15 (d, 1H), 6.02 (m, 1H), 5.18 (m, 2H), 4.80 (d, 2H), 3.43 (m, 6H), 3.15 (m, 2H), 2.91 (s, 3H), 2.33 (s, 3H), 2.13 (m, 2H).

Example 54

6-allyl-N-(2',3'-dihydro-1'H-spiro[cyclopropane-1,4'-isoquinolin]-7'-yl)-6H-pyrido[2,3-c]pyrimido[4,5-e] [1,2]thiazin-2-amine 5,5-dioxide The title compound was prepared as described in Example 25, substituting Example 32E for Example 3A, and substituting tert-butyl 7'-amino-1'H-spiro[cyclopropane-1,4'-isoquinoline]-2'(3'H)-carboxylate for 4-(4-aminophenyl)piperazine-1-carboxylic acid ten-butyl ester. MS (ESI) m/e 447 (M+H)+. $^1$H NMR (400 MHz, DMSO-d$_6$, 90° C.) δ ppm 10.28 (s, 1H), 9.00 (s, 1H), 8.78 (dd, 1H), 8.70 (dd, 1H), 7.66 (m, 2H), 7.47 (m, 1H), 6.90 (d, 1H), 6.01 (m, 1H), 5.18 (m, 2H), 4.81 (d, 2H), 4.43 (s, 2H), 3.27 (s, 2H), 1.12 (m, 4H).

Example 55

6-methyl-N-[4-(4-methylpiperazin-1-yl)phenyl]-6H-pyrimido[4,5-e]thieno[3,2-c][1,2]thiazin-2-amine 5,5-dioxide 3-Chloroperoxybenzoic acid (59.3 mg, 0.240 mmol) was added to a solution of 6-methyl-2(methylthio)thieno[2',3':5,6]pyrido[4,3-d]pyrimidin-5(6H)-one (Maybridge Chemical) (60 mg, 0.200 mmol) in 5 mL toluene at 0° C. and the reaction mixture was stirred at room temperature for 40 minutes. Hunig's Base (0.095 mL, 0.541 mmol) and 4-(4-methylpiperazin-1-yl)aniline (46.0 mg, 0.240 mmol) were added to the reaction mixture and the mixture was stirred at room temperature for 3 days. The reaction mixture was concentrated and the residue was suspended in dimethylsulfoxide and methanol. The solids were collected to afford the title compound. MS (ESI) m/e 443 (M+H)+. $^1$H NMR (400 MHz, DMSO-d$_6$) δ ppm 2.25 (s, 3 H) 2.46-2.53 (m, 4 H) 3.08-3.17 (m, 4 H) 3.44 (s, 3 H) 6.84-6.95 (m, 2 H) 7.28 (d, J=5.49 Hz, 1 H) 7.58 (d, J=9.16 Hz, 2 H) 8.05 (d, J=5.49 Hz, 1H) 8.75 (s, 1 H) 9.84 (s, 1 H).

Example 56

6-methyl-N-[4-(4-methylpiperazin-1-yl)phenyl]-6H-pyrimido[5,4-c][2,1]benzothiazin-2-amine 5,5-dioxide Example 56A ethyl 2-(N-methylmethylsulfonamido)benzoate The title compound was prepared as described in Example 1B, substituting allyl bromide with iodomethane.

Example 56B 1-methyl-1H-2,1-benzothiazin-4(3H)-one 2,2-dioxide

Example 56B was prepared as described in Example 1C, substituting Example 1B with. Example 56A.

Example 56C 6-methyl-2-(methylthio)-6H-pyrimido[5,4-c][2,1]benzothiazine 5,5-dioxide The title compound was prepared as described in Example 1E, substituting Example 1C with Example 56B.

Example 56D 6-methyl-N-[4-(4-methylpiperazin-1-yl)phenyl]-6H-pyrimido[5,4-c][2,1]benzothiazin-2-amine 5,5-dioxide 3-Chloroperoxybenzoic acid (92 mg, 0.375 mmol) was added to a solution of Example 56C (100 mg, 0.341 mmol) in 3 mL toluene and the mixture was stirred at room temperature for 40 minutes. Hunig's Base (0.161 mL, 0.920 mmol) and 4-(4-methylpiperazin-1-yl)aniline (65.2 mg, 0.341 mmol) were added to the reaction mixture and the mixture was stirred overnight at room temperature. The reaction mixture was concentrated and the residue was suspended in ethyl acetate. The solids were collected to afford the title compound. MS (ESI) m/e 437 (M+H)$^+$. $^1$H NMR (400 MHz, DMSO-$d_6$) δ ppm 2.23 (s, 3 H) 2.43-2.49 (m, 4 H) 3.05-3.17 (m, 4 H) 3.40 (s, 3 H) 6.98 (d, J=8.24 Hz, 2H) 7.41-7.55 (m, 2 H) 7.56-7.71 (m, J=6.71 Hz, 2 H) 7.70-7.83 (m, 1 H) 8.43 (d, J=7.32 Hz, 1 H) 8.93 (s, 1 H) 10.27 (s, 1 H).

Example 57

6-methyl-N-[4-(morpholin-4-yl)phenyl]-6H-pyrimido[5,4-c][2,1]benzothiazin-2-amine 5,5-dioxide 3-Chloroperoxybenzoic acid (55.5 mg, 0.225 mmol) was added to a solution of Example 56C (60 mg, 0.205 mmol) in 3 mL toluene and the mixture was stirred at room temperature for 4 hours. Hunig's Base (0.096 mL, 0.552 mmol) and 4-morpholinoaniline (36.5 mg, 0.205 mmol) were added and the mixture was stirred at room temperature for 2 days. The reaction mixture was concentrated and the residue was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 424 (M+H)$^+$. $^1$H NMR (400 MHz, DMSO-$d_6$) δ ppm 3.03-3.16 (m, 4 H) 3.40 (s, 3 H) 3.70-3.82 (m, 4 H) 6.99 (d, J=7.93 Hz, 2 H) 7.41-7.54 (m, 2 H) 7.59-7.71 (m, 2 H) 7.72-7.83 (m, 1 H) 8.43 (d, J=7.63 Hz, 1 H) 8.94 (s, 1 H) 10.28 (s, 1 H).

Example 58

6-methyl-N-[4-(pyrrolidin-1-ylmethyl)phenyl]-6H-pyrimido[5,4-c][2,1]benzothiazin-2-amine 5,5-dioxide The title compound was prepared as described in Example 57, substituting 4-morpholinoaniline with 4-(pyrrolidin-1-ylmethyl)aniline. MS (ESI) m/e 422. (M+H)$^+$. $^1$H NMR (400 MHz, DMSO-$d_6$) δ ppm 1.83-2.11 (m, 4 H) 3.41 (s, 3 H) 4.33 (s, 2 H) 7.42-7.48 (m, 1 H) 7.50-7.55 (m, 3 H) 7.74-7.79 (m, 1 H) 7.88-7.93 (m, 2 H) 8.47 (dd, J=7.93, 1.53 Hz, 1 H) 8.97 (s, 1 H) 10.32 (s, 1 H).

Example 59

6-allyl-2-{[4-(4-methylpiperazin-1-yl)phenyl]amino}-6H-pyrimido[5,4-c][2,1]benzothiazine-7-carboxylic acid 5,5-dioxide

Example 59A dimethyl 2-aminoisophthalate

Trimethylsilyldiazaomethane (9.12 mL, 18.24 mmol) (2M in diethyl ether) was added slowly to a solution of 2-amino-3-(methoxycarbonyl)benzoic acid (2.0 g, 10.25 mmol) in anhydrous 9 mL tetrahydrofuran and 6 mL methanol then the mixture was stirred overnight at room temperature. The reaction mixture was concentrated and purified by flash chromatography (1-6% methanol/$CH_2Cl_2$) to afford the title compound.

Example 59B dimethyl 2-(methylsulfonamido)isophthalate

A mixture of Example 59A (1.50 g, 7.17 mmol), pyridine (1.74 mL, 21.51 mmol) and methanesulfonic anhydride (2.50 g, 14.34 mmol) in 60 mL 1,2-dichloroethane was stirred overnight at 80° C. The reaction mixture was concentrated and the residue was purified by flash chromatography (0-7% methanol/$CH_2Cl_2$) to afford the title compound.

Example 59C dimethyl 2-[allyl(methylsulfonyl)amino]isophthalate

A mixture of Example 59B (980 mg, 3.41 mmol) and $K_2CO_3$ (967 mg, 7.00 mmol) in 4 mL N,N-dimethylformamide at 0° C. was stirred at 0° C. for 15 minutes. Allyl bromide (0.370 ml, 4.37 mmol) was added dropwise, and the mixture was heated at 45° C. for 2 days. The reaction mixture was diluted with $CH_2Cl_2$ and washed with $H_2O$ (twice), dried over $Na_2SO_4$, filtered, and concentrated. The residue was purified by flash chromatography (0-8% methanol/$CH_2Cl_2$) to afford the title compound.

Example 59D methyl 1-allyl-4-oxo-3,4-dihydro-1H-2,1-benzothiazine-8-carboxylate 2,2-dioxide Example 59C (830 mg, 2.54 mmol) in 4 mL N,N-dimethylformamide was added dropwise to a suspension of 60% sodium hydride (101 mg, 2.54 mmol) in 3 mL N,N-dimethylformamide at 0° C. then stirred at room temperature for 1 hour. The reaction was diluted with $CH_2Cl_2$, then acidified with 1N HCl(aq). The layers were separated and the organics were rinsed with $H_2O$ (three times). The solvent was evapo-

Example 59E 6-allyl-2-{[4-(4-methylpiperazin-1-yl)phenyl]amino}-6H-pyrimido[5,4-c][2,1]benzothiazine-7-carboxylic acid 5,5-dioxide Example 59D (0.501 g, 1.712 mmol) in N,N-dimethylformamide dimethyl acetal (1.14 mL, 8.56 mmol) was stirred at 55° C. overnight. The reaction mixture was concentrated and the residue was taken up in 10 mL 2-methoxyethanol. The mixture was treated with 1-(4-(4-methylpiperazin-1-yl)phenyl)guanidine (0.439 g, 1.884 mmol) and $K_2CO_3$ (1.420 g, 10.27 mmol) and stirred at 100° C. for 3 hours. The reaction mixture was concentrated and the residue was purified by reverse-phase HPLC performed on a Phenomenex Luna C8 AXIA column (30×75 mm, 100 Å) using a gradient of 10% to 95% acetonitrile:10 mM ammonium acetate in water to afford the title compound. MS (ESI) m/e 507 (M+H)$^+$. $^1$H NMR (400 MHz, DMSO-d$_6$) δ ppm 2.88 (s, 3 H) 2.89-3.05 (m, 2 H) 3.08-3.30 (m, 2 H) 3.34-3.97 (m, 3 H) 4.28 (d, J=7.02 Hz, 2 H) 4.78-4.94 (m, 2 H) 5.26-5.46 (m, 1 H) 7.00-7.12 (m, 2 H) 7.59-7.75 (m, 3 H) 8.13 (dd, J=7.63, 1.53 Hz, 1 H) 8.52 (d, J=7.63 Hz, 1 H) 8.88 (s, 1 H) 9.83 (s, 1 H) 10.37 (s, 1 H) 13.57 (s, 1 H).

Example 60 methyl 6-allyl-2-{[4-(4-methylpiperazin-1-yl)phenyl]amino}-6H-pyrimido[5,4-c][2,1]benzothiazine-7-carboxylate 5,5-dioxide Trimethylsilyldiazaomethane (105 μL, 0.211 mmol) (2M in diethyl ether) was added slowly to a solution of Example 59E (60 mg, 0.118 mmol) in 0.6 mL tetrahydrofuran and 0.6 mL methanol, and the mixture was stirred at room temperature for 2 hours. The reaction mixture was concentrated and the residue was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 521 (M+H)$^+$. $^1$H NMR (400 MHz, DMSO-d$_6$) δ ppm 2.88 (s, 3 H) 2.90-3.01 (m, 2 H) 3.12-3.26 (m, 2 H) 3.48-3.63 (m, 1 H) 3.80 (s, 2 H) 3.93 (s, 3 H) 4.22 (d, J=7.02 Hz, 2 H) 4.83-4.95 (m, 2 H) 5.29-5.45 (m, 1 H) 7.06 (d, J=8.24 Hz, 2 H) 7.61-7.78 (m, 3 H) 8.14 (dd, J=7.63, 1.53 Hz, 1 H) 8.54 (d, J=7.32 Hz, 1 H) 8.89 (s, 1 H) 9.71 (s, 1 H) 10.38 (s, 1 H).

Example 61

6-allyl-N-methyl-2-{[4-(4-methylpiperazin-1-yl)phenyl]amino}-6H-pyrimido[5,4-c][2,1]benzothiazine-7-carboxamide 5,5-dioxide A mixture of Example 59E (20 mg, 0.039 mmol), O-(7-azabenzotriazol-1-yl)-N,N,N',N'-tetramethyluronium hexafluorophosphate (40 mg, 0.105 mmol) and Hunig's Base (0.014 mL, 0.079 mmol) in 2 mL N,N-dimethylformamide was stirred at room temperature for 20 minutes. Methylamine (2M in tetrahydrofuran) (0.059 mL, 0.118 mmol) was added and the mixture was stirred at room temperature for 1 hour. The reaction mixture was concentrated and the residue was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 520 (M+H)$^+$. $^1$H NMR (500 MHz, DMSO-d$_6$) δ ppm 2.23 (s, 3 H) 2.42-2.49 (m, 4 H) 2.82 (d, J=4.58 Hz, 3 H) 3.07-3.15 (m, 4 H) 4.27 (d, J=7.02 Hz, 2 H) 4.84-4.97 (m, 2 H) 5.32-5.44 (m, 1 H) 6.92-7.04 (m, 2 H) 7.59-7.69 (m, 3 H) 7.73 (dd, J=7.63, 1.53 Hz, 1 H) 8.34-8.45 (m, 2 H) 8.83 (s, 1 H).

Example 62

6-allyl-N-(2-hydroxyethyl)-2-{[4-(4-methylpiperazin-1-yl)phenyl]amino}-6H-pyrimido[5,4-c][2,1]benzothiazine-7-carboxamide 5,5-dioxide The title compound was prepared as described in Example 61 substituting methylamine with 2-aminoethanol. MS (ESI) m/e 550 (M+H)$^+$. $^1$H NMR (500 MHz, DMSO-d$_6$) δ ppm 2.23 (s, 3 H) 2.41-2.48 (m, 4 H) 3.05-3.15 (m, 4 H) 3.52-3.60 (m, 3 H) 4.27 (d, J=6.71 Hz, 2 H) 4.71-4.83 (m, 1 H) 4.85-4.99 (m, 2 H) 5.29-5.43 (m, 1 H) 6.91-7.03 (m, 2 H) 7.55-7.72 (m, 3 H) 7.78 (dd, J=7.63, 1.53 Hz, 1 H) 8.33-8.46 (m, 2 H) 8.83 (s, 1 H) 10.29 (s, 1 H).

Example 63

6-allyl-8-bromo-N-phenyl-6H-pyrimido[5,4-c][2,1]benzothiazin-2-amine 5,5-dioxide

Example 63A methyl 4-bromo-2-(methylsulfonamido)benzoate

Methanesulfonyl chloride (29.6 mL, 380 mmol) was added slowly to a solution of methyl 2-amino-4-bromobenzoate (17.5 g, 76 mmol) and pyridine (30.8 mL, 380 mmol) in 200 mL $CH_2Cl_2$ at 0° C. The solution was stirred at room temperature for 2 days. The reaction was acidified with 1M HCl (aq) and extracted into $CH_2Cl_2$. The combined extracts were washed with brine, dried over $Na_2SO_4$, filtered, and concentrated. The residue was purified by flash chromatography (2-40% ethyl acetate/hexane) to afford the title compound.

Example 63B methyl 2-[allyl(methylsulfonyl)amino]-4-bromobenzoate

A mixture of Example 63A (10.46 g, 33.9 mmol) and $K_2CO_3$ (9.62 g, 69.6 mmol) in 40 mL N,N-dimethylformamide was stirred at 0° C. for 15 minutes. Allyl bromide (3.68 mL, 43.5 mmol) was added dropwise. The mixture was heated at 55° C. overnight. The reaction mixture was diluted with $CHCl_3$ and washed with $H_2O$ (three times). The organic layer was dried over $Na_2SO_4$, filtered, concentrated, and purified by flash chromatography (0-7% methanol/$CH_2Cl_2$) to afford the title compound.

Example 63C 1-allyl-7-bromo-1H-2,1-benzothiazin-4(3H)-one 2,2-dioxide

Example 63B (6.95 g, 19.96 mmol) in 16 mL N,N-dimethylformamide was added dropwise to a stirred suspension of 60% sodium hydride (0.798 g, 19.96 mmol) in 16 mL N,N-dimethylformamide at 0° C. then stirred at room temperature for 3 hours. The reaction mixture was neutralized with aqueous HCl (1M) and the resulting solid was collected to afford the title compound.

Example 63D (3Z)-1-allyl-7-bromo-3-[(dimethylamino)methylene]-1H-2,1-benzothiazin-4(3H)-one 2,2-dioxide Example 63C (7 g, 22.14 mmol) in N,N-dimethylformamide dimethyl acetal (14.79 mL, 111 mmol) was stirred at 60° C. overnight and concentrated. The crude title compound was used in the next step without further purification.

Example 63E 6-allyl-8-bromo-N-phenyl-6H-pyrimido[5,4-c][2,1]benzothiazin-2-amine 5,5-dioxide Example 63D (50 mg, ~0.135 mmol) was combined with 1-phenylguanidine (20.02 mg, 0.148 mmol), $K_2CO_3$ (55.8 mg, 0.404 mmol) and 2-methoxyethanol (1 mL). The reaction mixture was stirred at 100° C. for 2 hours, and concentrated. The crude material was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 443 (M+H)$^+$. $^1$H NMR (400 MHz, DMSO-$d_6$) δ ppm 4.65 (d, J=4.88 Hz, 2 H) 5.16-5.31 (m, 2 H) 5.79-5.91 (m, 1 H) 7.11 (t, J=7.48 Hz, 1H) 7.40 (t, J=7.93 Hz, 2 H) 7.67-7.72 (m, 1 H) 7.75 (d, J=1.83 Hz, 1 H) 7.80 (d, J=7.93 Hz, 2H) 8.36 (d, J=8.54 Hz, 1 H) 9.01 (s, 1 H) 10.53 (s, 1 H).

Example 64

6-allyl-8-bromo-N-[4-(4-methylpiperazin-1-yl)phenyl]-6H-pyrimido[5,4-c][2,1]benzothiazin-2-amine 5,5-dioxide

Example 64A 6-allyl-8-bromo-2-(methylthio)-6H-pyrimido[5,4-c][2,1]benzothiazine 5,5-dioxide Example 63D (1.17 g, ~3.16 mmol) and S-methylthiourea (0.313 g, 3.48 mmol) in 14 mL acetic acid was stirred at 105° C. overnight. The reaction mixture was concentrated and the residue was purified by flash chromatography (0-8% methanol/$CH_2Cl_2$) to afford the title compound.

Example 64B 6-allyl-8-bromo-N-[4-(4-methylpiperazin-1-yl)phenyl]-6H-pyrimido[5,4-c][2,1]benzothiazin-2-amine 5,5-dioxide 3-Chloroperoxybenzoic acid (61.3 mg, 0.249 mmol) was added to Example 64A (90 mg, 0.226 mmol) in $CH_2Cl_2$ (4 ml) and the mixture was stirred at room temperature for 30 minutes. Hunig's Base (0.107 mL, 0.610 mmol) and 4-(4-methylpiperazin-1-yl)aniline (43.2 mg, 0.226 mmol) were added and the mixture was stirred overnight at room temperature. The reaction mixture was concentrated. The residue was suspended in ethyl acetate and the solids were collected to afford the title compound. MS (ESI) m/e 541 (M+H)$^+$. $^1$H NMR (500 MHz, DMSO-$d_6$) δ ppm 2.23 (s, 3 H) 2.43-2.48 (m, 4 H) 3.06-3.15 (m, 4H) 4.64 (d, J=4.88 Hz, 2 H) 5.14-5.31 (m, 2 H) 5.78-5.90 (m, 1 H) 6.97 (d, J=7.32 Hz, 2 H) 7.52-7.71 (m, 3 H) 7.73 (d, J=1.83 Hz, 1 H) 8.32 (s, 1 H) 8.93 (s, 1 H) 10.31 (s, 1 H).

Example 65 methyl 2-{[4-(4-methylpiperazin-1-yl)phenyl]amino}-6H-pyrimido[5,4-c][2,1]benzothiazine-8-carboxylate 5,5-dioxide Example 64B (695 mg, 1.284 mmol) was combined with [1,1'-bis(diphenylphosphino)ferrocene]dichloropalladium (II) (47.0 mg, 0.064 mmol) and triethylamine (0.358 mL, 2.567 mmol) in 50 mL methanol in a 250 mL stainless steel pressure bottle. The mixture was pressurized with carbon monoxide (60 psi), and stirred at 100° C. for 16 hours. The reaction mixture was concentrated. The residue was suspended in $CH_2Cl_2$ and the solids were collected to afford the title compound. The filtrate was purified by flash chromatography (8-15% methanol/$CH_2Cl_2$) to afford additional the title compound. MS (ESI) m/e 481 (M+H)$^+$. $^1$H NMR (300 MHz, DMSO-$d_6$) δ ppm 2.72 (s, 3 H) 3.08-3.21 (m, 4H) 3.86 (s, 3 H) 5.74 (d, 1 H) 7.02 (d, J=9.16 Hz, 2 H) 7.30 (d, J=8.14 Hz, 1 H) 7.41 (s, 1H) 7.73 (d, J=8.82 Hz, 2 H) 8.31 (d, J=8.14 Hz, 1 H) 8.71 (s, 1 H) 9.77 (s, 1 H).

Example 66

8-bromo-N-[4-(4-methylpiperazin-1-yl)phenyl]-6-propyl-6H-pyrimido[5,4-c][2,1]benzothiazin-2-amine 5,5-dioxide

Example 66A methyl 4-bromo-2-[(methylsulfonyl)(propyl)amino]benzoate

The title compound was prepared as described in Example 63B, substituting allyl bromide with 1-iodopropane.

Example 66B 7-bromo-1-propyl-1H-2,1-benzothiazin-4(3H)-one 2,2-dioxide

The title compound was prepared as described in Example 63C, substituting Example 63B with Example 66A.

Example 66C (3Z)-7-bromo-3-[(dimethylamino)methylene]-1-propyl-1H-2,1-benzothiazin-4(3H)-one 2,2-dioxide The title compound was prepared as described in Example 63D, substituting Example 63C with Example 66B.

Example 66D 8-bromo-N-[4-(4-methylpiperazin-1-yl)phenyl]-6-propyl-6H-pyrimido[5,4-c][2,1]benzothiazin-2-amine 5,5-dioxide A mixture of Example 66C (7.0 g, 18.75 mmol), 1-(4-(4-methylpiperazin-1-yl)phenyl)guanidine (4.81 g, 20.63 mmol), and $K_2CO_3$ (7.78 g, 56.3 mmol) in 120 mL 2-methoxyethanol was heated at 100° C. for 1 hour. The reaction mixture was concentrated and the product was purified by flash chromatography (2-15% methanol/$CH_2Cl_2$) to afford the title compound. MS (ESI) m/e 543 (M+H)+. $^1$H NMR (300 MHz, DMSO-$d_6$) δ ppm 0.75 (t, J=7.46 Hz, 3 H) 1.38-1.65 (m, 2 H) 2.24 (s, 3 H) 2.42-2.56 (m, 4 H) 3.06-3.19 (m, 4 H) 3.98 (t, J=7.29 Hz, 2 H) 6.97 (d, J=8.82 Hz, 2 H) 7.51-7.75 (m, 3 H) 7.87 (d, J=1.70 Hz, 1H) 8.32 (d, J=8.48 Hz, 1 H) 8.91 (s, 1 H) 10.27 (s, 1 H).

Example 67

N-[4-(4-methylpiperazin-1-yl)phenyl]-6-propyl-6H-pyrimido[5,4-c][2,1]benzothiazin-2-amine 5,5-dioxide Example 66D (60 mg, 0.110 mmol), furan-2-ylboronic acid (12.35 mg, 0.110 mmol), tetrakis(triphenylphosphine) palladium(0) (8.93 mg, 7.73 μmol), 2M $K_2CO_3$ (aq) (0.166 mL, 0.331 mmol), N,N-dimethylformamide (1 mL) and 2-propanol (0.8 mL) were placed in a microwave tube, flushed with $N_2$ and heated in a Biotage microwave reactor at 150° C. for 25 minutes. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 465 (M+H)+. $^1$H NMR (300 MHz, DMSO-$d_6$) δ ppm 0.76 (t, 3H) 1.46-1.60 (m, 2H) 2.22 (s, 3H) 2.40-2.49 (m, 4H) 3.06-3.17 (m, 4H) 3.91 (d, 2H) 6.97 (d, J=9.16 Hz, 2H) 7.47 (t, J=7.63 Hz, 1H) 7.56-7.68 (m, 3H) 7.70-7.80 (m, 1H) 8.42 (d, J=7.12 Hz, 1H) 8.89 (s, 1H) 10.22 (s, 1H).

Example 68

N-[4-(4-methylpiperazin-1-yl)phenyl]-8-phenyl-6-propyl-6H-pyrimido[5,4-c][2,1]benzothiazin-2-amine 5,5-dioxide Example 66D (60 mg, 0.110 mmol), phenylboronic acid (20.2 mg, 0.166 mmol), tetrakis(triphenylphosphine)palladium(0) (8.9 mg, 7.73 μmol), 2M $K_2CO_3$ (aq) (0.166 mL, 0.331 mmol), N,N-dimethylformamide (1 mL) and 2-propanol (0.8 ml) were placed in a microwave tube, flushed with $N_2$, and heated in a Biotage microwave reactor at 150° C. for 20 minutes. The resulting precipitate was filtered and washed with methanol to afford the title compound. MS (ESI) m/e 541 (M+H)+. $^1$H NMR (300 MHz, DMSO-$d_6$) δ ppm 0.76 (t, J=7.34 Hz, 3 H) 1.47-1.61 (m, 2 H) 2.23 (s, 3 H) 2.35-2.49 (m, 4 H) 3.03-3.16 (m, 4 H) 4.05 (t, J=7.14 Hz, 2 H) 6.98 (d, J=8.72 Hz, 2 H) 7.42-7.71 (m, 5 H) 7.75-7.90 (m, 4 H) 8.49 (d, J=8.33 Hz, 1 H) 8.90 (s, 1 H) 10.25 (s, 1 H).

Example 69

N-[4-(4-methylpiperazin-1-yl)phenyl]-6-propyl-8-(pyridin-3-yl)-6H-pyrimido[5,4-c][2,1]benzothiazin-2-amine 5,5-dioxide The title compound was prepared as described in Example 68 substituting phenylboronic acid with pyridin-3-ylboronic acid. MS (ESI) m/e 542 (M+H)+. $^1$H NMR (500 MHz, DMSO-$d_6$) δ ppm 0.76 (t, J=7.32 Hz, 3 H) 1.48-1.60 (m, 2 H) 2.23 (s, 3 H) 2.43-2.49 (m, 4 H) 3.09-3.16 (m, 4 H) 4.08 (t, J=7.02 Hz, 2 H) 6.98 (d, 2 H) 7.55-7.72 (m, 3 H) 7.85 (d, J=8.24 Hz, 1 H) 7.92 (d, J=1.53 Hz, 1 H) 8.25-8.30 (m, 1H) 8.51 (s, 1 H) 8.67 (dd, J=4.88, 1.53 Hz, 1 H) 8.91 (s, 1 H) 9.08 (d, J=2.14 Hz, 1 H) 10.28 (s, 1 H).

Example 70

N-[4-(4-methylpiperazin-1-yl)phenyl]-6-propyl-8-(1H-pyrazol-4-yl)-6H-pyrimido[5,4-c][2,1]benzothiazin-2-amine 5,5-dioxide The title compound was prepared as described in Example 68 substituting phenylboronic acid with 4-(4,4,5,5-tetramethyl-1,3,2-dioxaborolan-2-yl)-1H-pyrazole. MS (ESI) m/e 531 (M+H)+. $^1$H NMR (300 MHz, DMSO-$d_6$) δ ppm 0.74 (t, J=7.34 Hz, 3 H) 1.38-1.59 (m, 2 H) 2.23 (s, 3 H) 2.37-2.49 (m, 4 H) 3.05-3.17 (m, 4 H) 4.01 (t, J=7.14 Hz, 2 H) 6.97 (d, J=9.12 Hz, 2 H) 7.53-7.80 (m, 4 H) 8.19-8.43 (m, 3 H) 8.85 (s, 1 H) 10.19 (s, 1 H).

Example 71

4-(2-{[4-(4-methylpiperazin-1-yl)phenyl]amino}-5,5-dioxido-6-propyl-6H-pyrimido[5,4-c][2,1]benzothiazin-8-yl)benzamide The title compound was prepared as described in Example 68, substituting phenylboronic acid with 4-carbamoylphenylboronic acid. MS (ESI) m/e 584 (M+H)+. $^1$H NMR (300 MHz, DMSO-$d_6$) δ ppm 0.76 (t, J=7.34 Hz, 3 H) 1.44-1.63 (m, 2 H) 2.23 (s, 3 H) 2.42-2.53 (m, 4 H) 3.08-3.18 (m, 4 H) 4.07 (t, J=7.14 Hz, 2 H) 6.98 (d, J=8.73 Hz, 2 H) 7.46 (s, 1 H) 7.56-7.71 (m, 2 H) 7.81-7.91 (m, 2 H) 7.92-7.99 (m, 2 H) 8.00-8.06 (m, 2 H) 8.09 (s, 1 H) 8.50 (d, J=8.33 Hz, 1 H) 8.91 (s, 1 H) 10.26 (s, 1 H).

Example 72

N-cyclopropyl-4-(2-{[4-(4-methylpiperazin-1-yl)phenyl]amino}-5,5-dioxido-6-propyl-6H-pyrimido[5,4-c][2,1]benzothiazin-8-yl)benzamide The title compound was prepared as described in Example 68, substituting phenylboronic acid with N-cyclopropyl-4-(4,4,5,5-tetramethyl-1,3,2-dioxaborolan-2-yl)benzamide. MS (ESI) m/e 624 (M+H)+. $^1$H NMR (300 MHz, DMSO-$d_6$) δ ppm 0.55-0.64 (m, 2 H) 0.67-0.81 (m, 5 H) 1.43-1.62 (m, 2 H) 2.23 (s, 3 H) 2.39-2.53 (m, 4 H) 2.82-2.95 (m, 1 H) 3.05-3.17 (m, 4 H) 4.07 (t, J=7.14 Hz, 2 H) 6.98 (d, J=8.73 Hz, 2 H) 7.65 (s, 2H) 7.80-7.89 (m, 2 H) 7.91-8.02 (m, 4 H) 8.44-8.57 (m, 2 H) 8.91 (s, 1 H) 10.26 (s, 1H).

Example 73

8-(2-aminopyrimidin-5-yl)-N-[4-(4-methylpiperazin-1-yl)phenyl]-6-propyl-6H-pyrimido[5,4-c][2,1]benzothiazin-2-amine 5,5-dioxide The title compound was prepared as described in Example 68, substituting phenylboronic acid with 5-(4,4,5,5-tetramethyl-1,3,2-dioxaborolan-2-yl)pyrimidin-2-amine. MS (ESI) m/e 558 (M+H)+. $^1$H NMR (300 MHz, DMSO-$d_6$) δ ppm 0.74 (t, J=7.34 Hz, 3 H) 1.42-1.62 (m, 2 H) 2.23 (s, 3 H) 2.40-2.54 (m, 4 H) 3.06-3.17 (m, 4 H) 4.05 (t, J=7.34 Hz, 2H) 6.91-7.05 (m, 4 H) 7.63 (s, 2 H) 7.72-7.85 (m, 2 H) 8.43 (d, J=8.33 Hz, 1 H) 8.79 (s, 2H) 8.88 (s, 1 H) 10.22 (s, 1 H).

Example 74

N-[4-(4-methylpiperazin-1-yl)phenyl]-6-propyl-8-(3-thienyl)-6H-pyrimido[5,4-c][2,1]benzothiazin-2-amine 5,5-dioxide Example 66D (60 mg, 0.110 mmol), thiophen-3-ylboronic acid (21.2 mg, 0.166 mmol), tetrakis(triphenylphosphine)

palladium(0) (8.9 mg, 7.73 μmol), 2M K₂CO₃ (aq) (0.166 mL, 0.331 mmol), N,N-dimethylformamide (1 mL) and 2-propanol (0.8 mL) were placed in a microwave tube, flushed with N₂, and heated in a Biotage microwave reactor at 150° C. for 25 minutes. The reaction mixture was filtered and the filtrate was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 547 (M+H)⁺. ¹H NMR (400 MHz, DMSO-d₆) δ ppm 0.75 (t, J=7.32 Hz, 3 H) 1.38-1.60 (m, 2 H) 2.23 (s, 3 H) 2.41-2.52 (m, 4 H) 3.06-3.19 (m, 4 H) 4.05 (t, J=7.02 Hz, 2 H) 6.98 (d, J=8.24 Hz, 2 H) 7.56-7.70 (m, 2H) 7.71-7.81 (m, 2 H) 7.82-7.92 (m, 2H) 8.24 (dd, J=2.90, 1.37 Hz, 1 H) 8.43 (d, J=7.63 Hz, 1 H) 8.89 (s, 1 H) 10.23 (s, 1 H).

Example 75

4-(2-{[4-(4-methylpiperazin-1-yl)phenyl]amino}-5,5-dioxido-6-propyl-6H-pyrimido[5,4-c][2,1]benzothiazin-8-yl)phenol The title compound was prepared as described in Example 74, substituting thiophen-3-ylboronic acid with 4-hydroxyphenylboronic acid. MS (ESI) m/e 557 (M+H)⁺. ¹H NMR (400 MHz, DMSO-d₆) δ ppm 0.76 (t, J=7.32 Hz, 3 H) 1.45-1.63 (m, 2 H) 2.23 (s, 3 H) 2.41-2.52 (m, 4 H) 2.99-3.21 (m, 4 H) 4.03 (t, J=7.17 Hz, 2 H) 6.84-7.07 (m, 4 H) 7.52-7.82 (m, 6 H) 8.43 (d, J=7.93 Hz, 1 H) 8.88 (s, 1 H) 9.81 (s, 1 H) 10.22 (s, 1 H).

Example 76

N-[4-(4-methylpiperazin-1-yl)phenyl]-6-propyl-8-(pyridin-4-yl)-6H-pyrimido[5,4-c][2,1]benzothiazin-2-amine 5,5-dioxide The title compound was prepared as described in Example 74, substituting thiophen-3-ylboronic acid with pyridin-4-ylboronic acid. MS (ESI) m/e 542 (M+H)⁺. ¹H NMR (400 MHz, DMSO-d₆) δ ppm 0.76 (t, J=7.32 Hz, 3 H) 1.49-1.59 (m, 2 H) 2.23 (s, 3 H) 2.43-2.53 (m, 4 H) 3.10-3.16 (m, 4 H) 4.08 (t, J=6.87 Hz, 2 H) 6.94-7.01 (m, 2 H) 7.65 (s, 2 H) 7.87-7.99 (m, 4 H) 8.52 (s, 1 H) 8.72-8.75 (m, 2 H) 8.93 (s, 1 H) 10.28 (s, 1 H).

Example 77

N-[4-(4-methylpiperazin-1-yl)phenyl]-6-propyl-8-(1H-pyrrolo[2,3-b]pyridin-3-yl)-6H-pyrimido[5,4-c][2,1]benzothiazin-2-amine 5,5-dioxide The title compound was prepared as described in Example 74, substituting thiophen-3-ylboronic acid with 3-(4,4,5,5-tetramethyl-1,3,2-dioxaborolan-2-yl)-1H-pyrrolo[2,3-b]pyridine. MS (ESI) m/e 581 (M+H)⁺. ¹H NMR (400 MHz, DMSO-d₆) δ ppm 0.78 (t, J=7.48 Hz, 3 H) 1.50-1.64 (m, 2 H) 2.23 (s, 3 H) 2.41-2.54 (m, 4 H) 3.06-3.18 (m, 4 H) 4.05 (t, J=7.17 Hz, 2 H) 6.93-7.04 (m, 2 H) 7.24 (dd, J=8.09, 4.73 Hz, 1 H) 7.67 (s, 2 H) 7.83 (d, J=1.53 Hz, 1 H) 7.89 (dd, J=8.24, 1.53 Hz, 1 H) 8.26 (s, 1 H) 8.33 (dd, J=4.73, 1.37 Hz, 1 H) 8.40-8.51 (m, 2 H) 8.88 (s, 1 H) 10.21 (s, 1 H) 12.27 (s, 1 H).

Example 78 methyl 2-{[4-(4-methylpiperazin-1-yl)phenyl]amino}-6-propyl-6H-pyrimido[5,4-c][2,1]benzothiazine-8-carboxylate 5,5-dioxide Example 66D (1.55 g, 2.85 mmol), [1,1'-bis(diphenylphosphino)ferrocene]dichloropalladium(II) (0.083 g, 0.114 mmol), and triethylamine (0.795 mL, 5.70 mmol) in 100 mL methanol in a 50 ml pressure bottle was pressurized with carbon monoxide (60 psi), and stirred at 100° C. for 22 hours. The reaction mixture was filtered and washed with methanol to collect the title compound. MS (ESI) m/e 523 (M+H)⁺. ¹H NMR (400 MHz, DMSO-d₆) δ ppm 0.77 (t, J=7.32 Hz, 3 H) 1.50-1.58 (m, 2H) 2.24 (s, 3 H) 2.45-2.51 (m, 4 H) 3.09-3.16 (m, 4 H) 3.93 (s, 3 H) 3.98 (t, J=7.48 Hz, 2H) 6.92-7.04 (m, 2 H) 7.62 (s, 2 H) 7.97-8.05 (m, 2 H) 8.56 (s, 1 H) 8.95 (s, 1 H) 10.34 (s, 1H).

Example 79

2-{[4-(4-methylpiperazin-1-yl)phenyl]amino}-6-propyl-6H-pyrimido[5,4-c][2,1]benzothiazine-8-carboxamide 5,5-dioxide A mixture of Example 78 (50 mg, 0.096 mmol) and ammonia (7M in methanol) (1.5 mL, 10.50 mmol) was stirred at 60° C. for 2 days. The reaction mixture was filtered and washed with methanol to collect the solids as the title compound. MS (ESI) m/e 508 (M+H)⁺. ¹H NMR (500 MHz, DMSO-d₆) δ ppm 0.77 (t, J=7.48 Hz 3 H) 1.50-1.61 (m, 2 H) 2.23 (s, 3 H) 2.42-2.50 (m, 4 H) 3.06-3.16 (m, 4 H) 3.98 (t, J=7.17 Hz, 2 H) 6.98 (s, 2 H) 7.51-7.75 (m, 3 H) 7.91 (d, J=8.24 Hz, 1 H) 7.96 (s, 1 H) 8.28 (s, 1 H) 8.48 (s, 1 H) 8.93 (s, 1H) 10.30 (s, 1 H).

Example 80

2-(2-{[4-(4-methylpiperazin-1-yl)phenyl]amino}-5,5-dioxido-6-propyl-6H-pyrimido[5,4-c][2,1]benzothiazin-8-yl)propan-2-ol To Example 78 (47 mg, 0.090 mmol) in 0.5 mL tetrahydrofuran at 0° C., methylmagnesium bromide (3M in diethyl ether) (90 μL, 0.270 mmol) was added and the mixture was stirred at 0° C. for 20 minutes. The reaction mixture was added dropwise to methanol and concentrated. The residue was purified by flash chromatography (2-15% methanol/CH₂Cl₂) to afford the title compound. MS (ESI) m/e 523 (M+H)⁺. ¹H NMR (400 MHz, DMSO-d₆) δ ppm 0.76 (t, J=7.32 Hz, 3 H) 1.50 (s, 6 H) 1.51-1.59 (m, 2 H) 2.30 (s, 3 H) 2.48-2.65 (m, 4 H) 3.07-3.21 (m, 4 H) 3.92 (t, J=7.02 Hz, 2 H) 5.34 (s, 1 H) 6.94-7.03 (m, 2 H) 7.51-7.76 (m, 4 H) 8.31-8.39 (m, 1 H) 8.87 (s, 1 H) 10.22 (s, 1 H).

Example 81

N-cyclohexyl-2-{[4-(4-methylpiperazin-1-yl)phenyl]amino}-6-propyl-6H-pyrimido[5,4-c][2,1]benzothiazine-8-carboxamide 5,5-dioxide Example 81A 2-{[4-(4-methylpiperazin-1-yl)phenyl]amino}-6-propyl-6H-pyrimido[5,4-c][2,1]benzothiazine-8-carboxylic acid 5,5-dioxide 1M Lithium hydroxide (7.65 mL, 7.65 mmol) was added dropwise to a mixture of Example 78 (1.0 g, 1.9 mmol) in 24 mL 1:1 tetrahydrofuran:methanol and the mixture stirred at room temperature for 2 hours. The reaction mixture was acidified with 10% HCl(aq) and the precipitate was collected to afford the title compound.

Example 81B

N-cyclohexyl-2-{[4-(4-methylpiperazin-1-yl)phenyl]amino}-6-propyl-6H-pyrimido[5,4-c][2,1]benzothiazine-8-carboxamide 5,5-dioxide A mixture of Example 81A (60 mg, 0.118 mmol), O-(7-azabenzotriazol-1-yl)-N,N,N',N'-tetramethyluronium hexafluorophosphate (90 mg, 0.236 mmol) and Hunig's Base (41.2 μL, 0.236 mmol) in 0.5 mL N,N-dimethylformamide was stirred at room temperature for 20 minutes. Cyclohexylamine (17.55 mg, 0.177 mmol) was added and the reaction was stirred at 60° C. for 2 hours. The reaction mixture was purified by reverse-phase HPLC performed on a Phenomenex Luna C8 AXIA column (30×75 mm, 100 Å) using a gradient of 10% to 95% acetonitrile:10 mM ammonium acetate in water to afford the title compound. MS (ESI) m/e 590 (M+H)$^+$. $^1$H NMR (500 MHz, DMSO-d$_6$) δ ppm 0.76 (t, J=7.32 Hz, 3 H) 1.10-1.22 (m, 1 H) 1.26-1.41 (m, 4 H) 1.47-1.58 (m, 2 H) 1.63 (d, J=12.51 Hz, 1 H) 1.71-1.80 (m, 2 H) 1.81-1.91 (m, 2 H) 2.44 (s, 3 H) 2.67-2.85 (m, 4 H) 3.14-3.27 (m, 4 H) 3.80 (dd, J=7.32, 3.66 Hz, 1 H) 3.98 (t, J=7.17 Hz, 2 H) 7.00 (d, J=7.02 Hz, 2 H) 7.67 (s, 2H) 7.83-7.96 (m, 2 H) 8.39-8.55 (m, 2 H) 8.94 (s, 1 H) 10.33 (s, 1 H).

Example 82

N-methyl-2-{[4-(4-methylpiperazin-1-yl)phenyl]amino}-6-propyl-6H-pyrimido[5,4-c][2,1]benzothiazine-8-carboxamide 5,5-dioxide The title compound was prepared as described in Example 81B, substituting cyclohexylamine with methylamine MS (ESI) m/e 522 (M+H)$^+$. $^1$H NMR (500 MHz, DMSO-d$_6$) δ ppm 0.77 (t, J=7.32 Hz, 3 H) 1.49-1.61 (m, 2 H) 2.23 (s, 3 H) 2.43-2.49 (m, 4 H) 2.85 (d, J=4.58 Hz, 3 H) 3.07-3.19 (m, 4 H) 3.98 (t, J=7.32 Hz, 2 H) 6.97 (s, 2 H) 7.64 (s, 2 H) 7.87 (d, J=8.24 Hz, 1 H) 7.92 (d, J=1.53 Hz, 1 H) 8.47 (s, 1 H) 8.74 (q, J=4.27 Hz, 1H) 8.93 (s, 1 H) 10.30 (s, 1 H).

Example 83

N,N-dimethyl-2-{[4-(4-methylpiperazin-1-yl)phenyl]amino}-6-propyl-6H-pyrimido[5,4-c][2,1]benzothiazine-8-carboxamide 5,5-dioxide The title compound was prepared as described in Example 81B, substituting cyclohexylamine with dimethylamine MS (ESI) m/e 536 (M+H)$^+$. $^1$H NMR (500 MHz, DMSO-d$_6$) δ ppm 0.75 (t, J=7.48 Hz, 3 H) 1.48-1.59 (m, 2 H) 2.25 (s, 3 H) 2.43-2.53 (m, 4H) 2.93 (s, 3 H) 3.04 (s, 3 H) 3.08-3.17 (m, 4 H) 3.98 (t, J=7.17 Hz, 2 H) 6.98 (d, J=7.63 Hz, 2 H) 7.45 (d, J=7.93 Hz, 2 H) 7.52-7.72 (m, 2 H) 8.45 (s, 1 H) 8.93 (s, 1 H) 10.29 (s, 1H).

Example 84

N-(2-hydroxyethyl)-2-{[4-(4-methylpiperazin-1-yl)phenyl]amino}-6-propyl-6H-pyrimido[5,4-c][2,1]benzothiazine-8-carboxamide 5,5-dioxide The title compound was prepared as described in Example 81B, substituting cyclohexylamine with 2-aminoethanol. MS (ESI) m/e 552 (M+H)$^+$. $^1$H NMR (500 MHz, DMSO-d$_6$) δ ppm 0.76 (t, J=7.32 Hz, 3 H) 1.49-1.59 (m, 2 H) 2.23 (s, 3 H) 2.44-2.49 (m, 4 H) 3.08-3.15 (m, 4 H) 3.35-3.44 (m, 2 H) 3.56 (t, J=6.10 Hz, 2 H) 3.99 (t, J=7.17 Hz, 2 H) 6.98 (d, J=6.10 Hz, 2 H) 7.57-7.71 (m, 2 H) 7.90 (d, J=8.24 Hz, 1 H) 7.96 (s, 1 H) 8.46 (s, 1 H) 8.78 (t, J=5.49 Hz, 1 H) 8.93 (s, 1 H) 10.30 (s, 1 H).

Example 85

N-(2-methoxyethyl)-2-{[4-(4-methylpiperazin-1-yl)phenyl]amino}-6-propyl-6H-pyrimido[5,4-c][2,1]benzothiazine-8-carboxamide 5,5-dioxide The title compound was prepared as described in Example 81B, substituting cyclohexylamine with 2-methoxyethylamine MS (ESI) m/e 566 (M+H)$^+$. $^1$H NMR (500 MHz, DMSO-d$_6$) δ ppm 0.77 (t, J=7.32 Hz, 3 H) 1.49-1.59 (m, 2 H) 2.26 (s, 3 H) 2.48-2.56 (m, 4 H) 3.14 (s, 4 H) 3.29 (s, 3 H) 3.46-3.51 (m, 3 H) 3.99 (t, J=7.17 Hz, 2 H) 6.98 (d, J=6.41 Hz, 2 H) 7.56-7.71 (m, 2 H) 7.90 (d, J=8.24 Hz, 1 H) 7.95 (d, J=1.53 Hz, 1 H) 8.47 (s, 1 H) 8.83-8.89 (m, 1 H) 8.93 (s, 1 H) 10.31 (s, 1 H).

Example 86

N-(trans-4-aminocyclohexyl)-2-{[4-(4-methylpiperazin-1-yl)phenyl]amino}-6-propyl-6H-pyrimido[5,4-c][2,1]benzothiazine-8-carboxamide 5,5-dioxide The title compound was prepared as described in Example 81B, substituting cyclohexylamine with trans-1,4-diaminocyclohexane. MS (ESI) m/e 605 (M+H)$^+$. $^1$H NMR (400 MHz, DMSO-d$_6$) δ ppm 0.75 (t, J=7.32 Hz, 3 H) 1.26 (s, 2 H) 1.31-1.47 (m, 2 H) 1.46-1.60 (m, 2 H) 1.80-1.94 (m, 4 H) 2.23 (s, 3 H) 2.42-2.49 (m, 4 H) 2.63-2.78 (m, 1 H) 3.06-3.16 (m, 4 H) 3.68-3.82 (m, 1 H) 3.97 (t, J=7.17 Hz, 2 H) 6.97 (d, J=8.54 Hz, 2 H) 7.64 (s, 2 H) 7.81-7.95 (m, 2 H) 8.40-8.56 (m, 2 H) 8.92 (s, 1 H) 10.29 (s, 1 H).

Example 87

2-{[4-(4-methylpiperazin-1-yl)phenyl]amino}-6-propyl-N-(pyridin-3-ylmethyl)-6H-pyrimido[5,4-c][2,1]benzothiazine-8-carboxamide 5,5-dioxide The title compound was prepared as described in Example 81B, substituting cyclohexylamine with pyridin-3-ylmethanamine MS (ESI) m/e 599 (M+H)$^+$. $^1$H NMR (500 MHz, DMSO-d$_6$) δ ppm 0.76 (t, J=7.32 Hz, 3 H) 1.48-1.61 (m, 2 H) 2.23 (s, 3 H) 2.41-2.49 (m, 4 H) 3.06-3.15 (m, 4 H) 3.99 (t, J=7.17 Hz, 2 H) 4.57 (d, J=5.80 Hz, 2 H) 6.98 (d, J=5.80 Hz, 2 H) 7.38 (dd, J=7.93, 4.88 Hz, 1 H) 7.53-7.72 (m, 2 H) 7.75-7.80 (m, 1 H) 7.94 (d, J=8.24 Hz, 1 H) 7.99 (d, J=1.22 Hz, 1 H) 8.44-8.53 (m, 2 H) 8.60 (d, J=1.53 Hz, 1H) 8.89-8.98 (m, 1 H) 9.40 (t, J=5.80 Hz, 1 H) 10.31 (s, 1 H).

Example 88 methyl 2-{[4-(4-methylpiperazin-1-yl)phenyl]amino}-6-phenyl-6H-pyrimido[5,4-c][2,1]benzothiazine-8-carboxylate 5,5-dioxide A mixture of Example 65 (83 mg, 0.173 mmol), phenylboronic acid (63.2 mg, 0.518 mmol), copper(II) acetate (62.7 mg, 0.345 mmol) and triethylamine (0.072 mL, 0.518 mmol) in 2 mL CH$_2$Cl$_2$ was stirred overnight at 40° C. The reaction mixture was concentrated and the residue was purified by reverse-phase HPLC performed on a Phenomenex Luna C8 AXIA column (30×75 mm, 100 Å) using a gradient of 10% to 95% acetonitrile:10 mM ammonium acetate in water to afford the title compound. MS (ESI) m/e 557 (M+H)+. $^1$H NMR (400 MHz, DMSO-d$_6$) δ ppm 2.27 (s, 3 H) 2.48-2.52 (m, 4 H) 3.09-3.20 (m, 4 H) 3.81 (s, 3 H) 7.00 (s, 2 H) 7.30-7.42 (m, 3 H) 7.47-7.60 (m, 4 H) 7.69 (s, 1 H) 8.01 (d, J=7.32 Hz, 1 H) 8.60 (s, 1 H) 8.95 (s, 1 H) 10.45 (s, 1 H).

Example 89 methyl 6-(3-methylphenyl)-2-{[4-(4-methylpiperazin-1-yl)phenyl]amino}-6H-pyrimido[5,4-c][2,1]benzothiazine-8-carboxylate 5,5-dioxide The title compound was prepared as described in Example 88, substituting phenylboronic acid with 3-tolylboronic acid. MS (ESI) m/e 571 (M+H)+. $^1$H NMR (500 MHz, DMSO-d$_6$) δ ppm 2.25 (s, 3 H) 2.35 (s, 3 H) 2.43-2.57 (m, 4 H) 3.08-3.20 (m, 4 H) 3.82 (s, 3 H) 6.93-7.06 (m, 2 H) 7.11-7.20 (m, 2 H) 7.30-7.41 (m, 2 H) 7.44 (t, J=7.78 Hz, 1H) 7.70 (s, 2 H) 8.01 (d, J=7.63 Hz, 1 H) 8.61 (s, 1 H) 8.94 (s, 1 H) 10.43 (s, 1 H).

Example 90 methyl 6-(3,5-dichlorophenyl)-2-{[4-(4-methylpiperazin-1-yl)phenyl]amino}-6H-pyrimido[5,4-c][2,1]benzothiazine-8-carboxylate 5,5-dioxide The title compound was prepared as described in Example 88, substituting phenylboronic acid with 3,5-dichlorophenylboronic acid. MS (ESI) m/e 625 (M+H)+. $^1$H NMR (500 MHz, DMSO-d$_6$) δ ppm 2.44-2.56 (m, 4 H) 2.70 (s, 3 H) 2.95-3.15 (m, 4 H) 3.84 (s, 3 H) 7.05 (d, J=8.85 Hz, 3 H) 7.27 (d, J=8.54 Hz, 2 H) 7.41-7.46 (m, 4 H) 8.01 (s, 1 H) 8.68 (s, 1 H).

Example 91 methyl 6-[3,5-bis(trifluoromethyl)phenyl]-2-{[4-(4-methylpiperazin-1-yl)phenyl]amino}-6H-pyrimido[5,4-c][2,1]benzothiazine-8-carboxylate 5,5-dioxide The title compound was prepared as described in Example 88, substituting phenylboronic acid with 3,5-bis(trifluoromethyl)phenylboronic acid. MS (ESI) m/e 693 (M+H)+. $^1$H NMR (500 MHz, DMSO-d$_6$) δ ppm 2.47-2.59 (m, 4 H) 2.72 (s, 3 H) 3.06-3.21 (m, 4 H) 3.85 (s, 3 H) 7.00 (d, 1 H) 7.09 (d, J=8.85 Hz, 2 H) 7.34 (d, J=8.54 Hz, 2 H) 7.89 (s, 1 H) 8.00-8.15 (m, 4 H) 8.71 (s, 1 H).

Example 92

8-(1H-imidazol-1-yl)-N-[4-(4-methylpiperazin-1-yl)phenyl]-6-propyl-6H-pyrimido[5,4-c][2,1]benzothiazin-2-amine 5,5-dioxide A mixture of Example 66D (50 mg, 0.092 mmol), imidazole (12.5 mg, 0.184 mmol), 1,10-phenanthroline (8.3 mg, 0.046 mmol), copper(I) iodide (1.7 mg, 9.2 µmol) and K$_2$CO$_3$ (25.4 mg, 0.184 mmol) in 1-methyl-2-pyrrolidinone (0.7 mL) was heated in a Biotage microwave reactor at 200° C. for 30 minutes. The reaction mixture was filtered and the filtrate was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 531 (M+H)+. $^1$H NMR (500 MHz, DMSO-d$_6$) δ ppm 0.76 (t, J=7.32 Hz, 3 H) 1.46-1.63 (m, 2 H) 2.88 (s, 3 H) 2.90-3.88 (m, 8 H) 4.08 (t, J=7.17 Hz, 2 H) 7.06 (d, J=7.93 Hz, 2 H) 7.60-7.75 (m, 2 H) 7.79-7.88 (m, 1 H) 7.96 (d, J=1.83 Hz, 1 H) 8.25 (s, 1 H) 8.50-8.60 (m, 1 H) 8.97 (s, 1 H) 9.24 (s, 1H) 9.82 (s, 1 H) 10.38 (s, 1 H).

Example 93

N-[4-(4-methylpiperazin-1-yl)phenyl]-6-propyl-8-(1H-pyrrol-1-yl)-6H-pyrimido[5,4-c][2,1]benzothiazin-2-amine 5,5-dioxide The title compound was prepared as described in Example 92, substituting imidazole with pyrrole. MS (ESI) m/e 530 (M+H)+. $^1$H NMR (500 MHz, DMSO-d$_6$) δ ppm 0.74 (t, J=7.32 Hz, 3 H) 1.46-1.57 (m, 2 H) 2.87-2.89 (d, J=2.44 Hz, 3 H) 2.92-3.95 (m, 8 H) 4.08 (t, J=7.17 Hz, 2 H) 6.34-6.42 (m, 2 H) 7.06 (d, J=8.24 Hz, 2 H) 7.57-7.80 (m, 5 H) 8.45 (d, J=7.93 Hz, 1 H) 8.91 (s, 1 H) 9.74 (s, 1 H) 10.30 (s, 1 H).

Example 94

N-[4-(4-methylpiperazin-1-yl)phenyl]-6-propyl-8-(1H-1,2,4-triazol-1-yl)-6H-pyrimido[5,4-c][2,1]benzothiazin-2-amine 5,5-dioxide The title compound was prepared as described in Example 92, substituting imidazole with 1,2,4-triazole. MS (ESI) m/e 532 (M+H)+. $^1$H NMR (500 MHz, DMSO-d$_6$) δ ppm 0.78 (t, J=7.32 Hz, 3 H) 1.53-1.64 (m, 2 H) 2.23 (s, 3 H) 2.43-2.48 (m, 4 H) 3.08-3.16 (m, 4 H) 4.05 (t, J=7.17 Hz, 2 H) 6.98 (d, J=2.14 Hz, 2 H) 7.53-7.72 (m, 2 H) 7.99 (dd, J=8.70, 1.68 Hz, 1 H) 8.04 (d, J=2.14 Hz, 1 H) 8.27-8.40 (m, 1 H) 8.57 (d, J=6.41 Hz, 1 H) 8.94 (s, 1 H) 9.54 (s, 1 H) 10.30 (s, 1 H).

Example 95 methyl 6-(2,6-dichlorobenzyl)-2-{[4-(4-methylpiperazin-1-yl)phenyl]amino}-6H-pyrimido[5,4-c][2,1]benzothiazine-8-carboxylate 5,5-dioxide A mixture of Example 65 (30 mg, 0.062 mmol), 2-(bromomethyl)-1,3-dichlorobenzene (22.5 mg, 0.094 mmol), and Cs$_2$CO$_3$ (30.5 mg, 0.094 mmol) in 0.8 mL N,N-dimethylformamide was stirred at room temperature for 1 hour. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 639 (M+H)+. $^1$H NMR (400 MHz, DMSO-d$_6$) δ ppm 2.28 (s, 3 H) 2.50-2.62 (m, 4 H) 3.08-3.21 (m, 4 H) 3.82 (s, 3 H) 4.99 (s, 2H) 6.95-7.04 (m, 2 H) 7.22-7.32 (m, 1 H) 7.34-7.48 (m, 3 H) 7.54-7.73 (m, 2 H) 8.02 (d, 1 H) 8.45 (d, J=8.24 Hz, 1 H) 8.97 (s, 1 H) 10.42 (s, 1 H).

Example 96

9-bromo-N-[4-(4-methylpiperazin-1-yl)phenyl]-6-propyl-6H-pyrimido[5,4-c][2,1]benzothiazin-2-amine 5,5-dioxide Example 96A methyl 5-bromo-2-(methylsulfonamido)benzoate Methanesulfonyl chloride (5.40 mL, 69.5 mmol) was added slowly to a solution of methyl 2-amino-5-bromobenzoate (8.0 g, 34.8 mmol) and pyridine (8.44 mL, 104 mmol) in 50 mL $CH_2Cl_2$ at 0° C. The solution was stirred at room temperature for 18 hours. The reaction mixture was acidified with 1M HCl (aq) and extracted into $CH_2Cl_2$. The combined extracts were washed with brine, dried over $Na_2SO_4$, filtered, and concentrated. The residue was purified by flash chromatography (2-40% ethyl acetate/hexane) to afford the title compound.

Example 96B methyl 5-bromo-2-(N-propylmethylsulfonamido)benzoate

A mixture of Example 96A (5.0 g, 16.23 mmol) and $K_2CO_3$ (4.49 g, 32.5 mmol) in 20 mL N,N-dimethylformamide was stirred at 0° C. for 15 minutes and 1-iodopropane (1.98 ml, 20.28 mmol) was added dropwise. The mixture was heated at 55° C. overnight. The reaction mixture was diluted with $CHCl_3$ and washed with $H_2O$ (three times). The organic layer was dried over $Na_2SO_4$, filtered, concentrated, and purified by flash chromatography (0-7% methanol/$CH_2Cl_2$) to afford the title compound.

Example 96C 6-bromo-1-propyl-1H-2,1-benzothiazin-4(3H)-one 2,2-dioxide

Example 96B (3.62 g, 10.34 mmol) in 8 mL N,N-dimethylformamide was added dropwise to a stirred suspension of 60% sodium hydride (0.620 g, 15.50 mmol) in 8 mL N,N-dimethylformamide at 0° C. and the mixture was stirred at room temperature for 3 hours. The reaction mixture was neutralized with aqueous HCl (1M) and the resulting solid was collected to afford the title compound.

Example 96D (3Z)-6-bromo-3-[(dimethylamino)methylene]-1-propyl-1H-2,1-benzothiazin-4(3H)-one 2,2-dioxide Example 96C (2.5 g, 7.86 mmol) in N,N-dimethylformamide dimethyl acetal (5.24 mL, 39.3 mmol) was stirred at 65° C. for 1 hour and concentrated. The crude title compound was used in the next step without further purification.

Example 96D 9-bromo-N-[4-(4-methylpiperazin-1-yl)phenyl]-6-propyl-6H-pyrimido[5,4-c][2,1]benzothiazin-2-amine 5,5-dioxide The title compound was prepared as described in Example 66D substituting Example 66C with Example 96C. MS (ESI) m/e 543 (M+H)$^+$. $^1$H NMR (300 MHz, DMSO-d$_6$) δ ppm 0.76 (t, J=7.34 Hz, 3 H) 1.46-1.61 (m, 2 H) 2.22 (s, 3 H) 2.40-2.52 (m, 4 H) 3.07-3.16 (m, 4H) 3.92 (t, J=7.14 Hz, 2 H) 6.96 (d, J=9.12 Hz, 2 H) 7.49-7.64 (m, 3 H) 7.91 (dd, J=8.73, 2.38 Hz, 1 H) 8.48 (s, 1 H) 8.93 (s, 1 H) 10.30 (s, 1 H).

Example 97

N-[4-(4-methylpiperazin-1-yl)phenyl]-9-phenyl-6-propyl-6H-pyrimido[5,4-c][2,1]benzothiazin-2-amine 5,5-dioxide Example 96D (60 mg, 0.110 mmol), phenylboronic acid (20.2 mg, 0.166 mmol), tetrakis(triphenylphosphine)palladium(0) (8.9 mg, 7.73 μmol), 2M $K_2CO_3$ (aq) (0.166 mL, 0.331 mmol), N,N-dimethylformamide (1 mL) and 2-propanol (0.8 ml) were placed in a microwave tube, flushed with $N_2$, and heated in a Biotage microwave reactor at 150° C. for 20 minutes. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water to afford the title compound. MS (ESI) m/e 541 (M+H)$^+$. $^1$H NMR (300 MHz, DMSO-d$_6$) δ ppm 0.79 (t, J=7.34 Hz, 3 H) 1.51-1.64 (m, 2H) 2.23 (s, 3 H) 2.42-2.54 (m, 4 H) 3.07-3.15 (m, 4 H) 3.98 (t, J=7.34 Hz, 2 H) 6.96 (d, J=8.73 Hz, 2 H) 7.40-7.49 (m, 1 H) 7.50-7.72 (m, 5 H) 7.77 (d, J=7.14 Hz, 2 H) 8.06 (dd, J=8.53, 2.18 Hz, 1 H) 8.71 (s, 1 H) 8.93 (s, 1 H) 10.26 (s, 1 H).

Example 98

N-[4-(4-methylpiperazin-1-yl)phenyl]-6-propyl-9-(pyridin-3-yl)-6H-pyrimido[5,4-c][2,1]benzothiazin-2-amine 5,5-dioxide The title compound was prepared as described in Example 97 substituting phenylboronic acid with pyridin-3-ylboronic acid. MS (ESI) m/e 542 (M+H)$^+$. $^1$H NMR (300 MHz, DMSO-d$_6$) δ ppm 0.80 (t, J=7.29 Hz, 3 H) 1.52-1.68 (m, 2 H) 2.79-2.92 (m, 3H) 2.90-3.01 (m, 2 H) 3.09-3.30 (m, 2 H) 3.47-3.64 (m, 2 H) 3.71-3.87 (m, 2 H) 4.01 (t, J=7.29 Hz, 2 H) 7.03 (d, J=8.82 Hz, 2 H) 7.59-7.83 (m, 3 H) 8.14 (dd, J=8.48, 2.37 Hz, 1 H) 8.27 (dd, J=6.10, 2.03 Hz, 1 H) 8.68 (dd, J=4.75, 1.36 Hz, 1 H) 8.74 (s, 1 H) 8.97 (s, 1 H) 9.04 (d, J=2.03 Hz, 1 H) 9.62 (s, 1 H) 10.34 (s, 1 H).

Example 99

N-[4-(4-methylpiperazin-1-yl)phenyl]-6-propyl-9-(pyridin-4-yl)-6H-pyrimido[5,4-c][2,1]benzothiazin-2-amine 5,5-dioxide The title compound was prepared as described in Example 97 substituting phenylboronic acid with pyridin-4-ylboronic acid. MS (ESI) m/e 542 (M+H)$^+$. $^1$H NMR (400 MHz, DMSO-d$_6$) δ ppm 0.80 (t, J=7.32 Hz, 3 H) 1.56-1.66 (m, 2 H) 2.88 (s, 3 H) 2.90-3.00 (m, 2 H) 3.12-3.26 (m, 2 H) 3.54 (s, 2 H) 3.79-3.87 (m, 2 H) 4.05 (t, J=7.20 Hz, 2 H) 7.00-7.12 (m, 2 H) 7.64-7.74 (m, 1 H) 7.79 (d, J=8.85 Hz, 1 H) 7.99 (s, 2 H) 8.25 (dd, J=8.70, 2.29 Hz, 1 H) 8.74-8.93 (m, 3 H) 8.99 (s, 1 H) 9.69 (s, 1 H) 10.39 (s, 1 H).

Example 100

N-methyl-3-(2-{[4-(4-methylpiperazin-1-yl)phenyl]amino}-5,5-dioxido-6-propyl-6H-pyrimido[5,4-c][2,1]benzothiazin-9-yl)benzamide The title compound was prepared as described in Example 97 substituting phenylboronic acid with 3-(methylcarbamoyl)phenylboronic acid. MS (ESI) m/e 598 (M+H)$^+$. $^1$H NMR (400 MHz, DMSO-d$_6$) δ ppm 0.83 (t, J=7.30 Hz, 3 H) 1.55-1.69 (m, 2H) 2.83-2.91 (m, 7 H) 3.27-3.43 (m, 7 H) 3.92-4.00 (t, J=7.20 Hz, 2 H) 7.05-7.13 (m, 2H) 7.60 (t, J=7.78 Hz, 1 H) 7.66 (d, J=8.85 Hz, 1 H) 7.75 (d, J=9.16 Hz, 2 H) 7.84-7.91 (m, 2H) 8.08 (dd, J=8.70, 2.29 Hz, 1 H) 8.27 (s, 1 H) 8.30-8.35 (m, 1 H) 8.78 (d, J=2.44 Hz, 1H) 8.88 (s, 1 H) 10.06 (s, 1 H).

Example 101

9-{2-[(dimethylamino)methyl]phenyl}-N-[4-(4-methylpiperazin-1-yl)phenyl]-6-propyl-6H-pyrimido[5,4-c][2,1]benzothiazin-2-amine 5,5-dioxide The title compound was prepared as described in Example 97 substituting phenylboronic acid with 2-(dimethylamino)methyl)phenylboronic acid. MS (ESI) m/e 598 (M+H)$^+$. $^1$H NMR (400 MHz, DMSO-d$_6$) δ ppm 0.87 (t, J=7.48 Hz, 3 H) 1.58-1.75 (m, 2 H) 2.59 (s, 6 H) 2.84-2.87 (m, 3 H) 3.17-3.54 (m, 8 H) 3.97 (t, J=7.32 Hz, 2 H) 4.30 (s, 2H) 6.88-7.00 (m, 2 H) 7.41-7.48 (m, 1 H) 7.52-7.67 (m, 5H) 7.69-7.79 (m, 2 H) 8.38 (d, J=2.14 Hz, 1 H) 8.89 (s, 1 H) 9.94 (s, 1 H).

Example 102

N-[5-(4-methylpiperazin-1-yl)pyridin-2-yl]-6-(prop-2-en-1-yl)-6H-pyrido[2,3-c]pyrimido[4,5-e][1,2]thiazin-2-amine 5,5-dioxide The title compound was prepared as described in Example 3B, substituting Example 32E for Example 3A, and substituting 1-methyl-4-(6-aminopyridin-3-yl)piperazine for 4-[2-(diethylamino)ethoxy]aniline. MS (ESI) m/e 465 (M+H)$^+$. $^1$H NMR (400 MHz, DMSO-d$_6$) δ ppm 10.73 (s, 1 H), 9.11 (s, 1 H), 8.82 (m, 1 H), 8.74 (m, 1 H), 8.17 (m, 1 H), 8.12 (d, 1 H), 7.61 (m, 1 H), 7.51 (m, 1H), 6.03 (m, 1 H), 5.20 (m, 2 H), 4.80 (d, 2 H), 3.89 (m, 2 H), 2.15 (m, 6H), 2.88 (s, 3H).

Example 103

N-[5-(piperazin-1-yl)pyridin-2-yl]-6-(prop-2-en-1-yl)-6H-pyrido[2,3-c]pyrimido[4,5-e][1,2]thiazin-2-amine 5,5-dioxide The title compound was prepared as described in Example 25, substituting Example 32E for Example 3A, and substituting 1-Boc-4-(6-aminopyridin-3-yl)piperazine for 4-(4-aminophenyl)piperazine-1-carboxylic acid tert-butyl ester. MS (ESI) m/e 451 (M+H)$^+$. $^1$H NMR (400 MHz, DMSO-d$_6$) δ ppm 10.73 (s, 1 H), 9.11 (s, 1 H), 8.82 (m, 2 H), 8.74 (m, 1 H), 8.15 (m, 2 H), 7.60 (m, 1 H), 7.51 (m, 1 H), 6.03 (m, 1 H), 5.20 (m, 2 H), 4.80 (d, 2 H), 3.41 (m, 4H), 3.29 (m, 4 H).

Example 104

Wee1 Assay

Wee1 kinase was assayed using a time-resolved fluorescence equilibrium binding assay monitoring displacement of a rapidly reversible Oregon Green-labeled ATP-competitive kinase probe (N-(2-(2-(2-(4-(4-(5-chloro-4-(2-(1-hydroxycyclobutyl)thiazol-5-yl)-1H-pyrrolo[2,3-b]pyridin-2-yl)phenyl)piperazin-1-yl)ethoxy)ethoxy)ethyl)-2',7'-difluoro-3',6'-dihydroxy-3-oxo-3H-spiro[isobenzofuran-1,9'-xanthene]-5-carboxamide) by competitive Wee1 inhibitors. GST-tagged-Wee1 kinase (Carnabio #05-177, 2 nM final concentration), was mixed with fluorescent probe (300 nM final concentration, K$_d$=137 nM) and terbium-labeled anti-GST antibody (1 nM final concentration, Invitrogen #PV3551) and then inhibitor (0.003 to 10 micromolar) in final volume of 18 μl kinase buffer (20 mM HEPES, pH 7.5, 10 mM MgCl$_2$, 100 μM Na$_3$VO$_4$, 0.0075% Triton X-100, 1 mM DTT, 2% DMSO), incubated (1 hour) to allow attainment of equilibrium and time-resolved fluorescence measured using an Envision plate reader (Perkin Elmer; ex=337 nM, em=495/520 nM).

Table 1 depicts enzyme inhibition data (K$_i$) for exemplary compounds.

| Example | Wee-1 binding (K$_i$ nM) |
|---|---|
| 1 | 1.8 |
| 2 | 1.7 |
| 3 | 4.8 |
| 4 | NA |
| 5 | 9 |
| 6 | 47 |
| 7 | 1230 |
| 8 | 106 |
| 9 | 50 |
| 10 | 5 |
| 11 | 31 |
| 12 | 738 |
| 13 | 2080 |
| 14 | 1440 |
| 15 | 166 |
| 16 | 7 |
| 17 | 2040 |
| 18 | 4 |
| 19 | 1.2 |
| 20 | 283 |
| 21 | 3140 |
| 22 | 1.7 |
| 23 | 3140 |
| 24 | 220 |
| 25 | 1.5 |
| 26 | 1.0 |
| 27 | 30 |
| 28 | 1.1 |
| 29 | 413 |
| 30 | 21 |
| 31 | 1.7 |
| 32 | 1450 |
| 33 | 3 |
| 34 | 2 |
| 35 | 48 |
| 36 | 9 |
| 37 | 5 |
| 38 | 51 |
| 39 | 15 |
| 40 | 5 |
| 41 | 2370 |
| 42 | 2 |
| 43 | 56 |
| 44 | 487 |
| 45 | 3 |
| 46 | 2 |
| 47 | 1.3 |
| 48 | 2 |
| 49 | 45 |
| 50 | 5 |
| 51 | 14 |
| 52 | 12 |
| 53 | 1.1 |
| 54 | 1.2 |
| 55 | 8 |
| 56 | 9 |
| 57 | 12 |
| 58 | 11 |
| 59 | 141 |
| 60 | 9 |
| 61 | 11 |
| 62 | 37 |
| 63 | 3140 |
| 64 | 2 |
| 65 | 256 |
| 66 | 6 |
| 67 | 4 |
| 68 | 92 |

| Example | Wee-1 binding ($K_i$ nM) |
|---|---|
| 69 | 4 |
| 70 | 5 |
| 71 | 4 |
| 72 | 7 |
| 73 | 3 |
| 74 | 20 |
| 75 | 14 |
| 76 | 5 |
| 77 | 57 |
| 78 | 6 |
| 79 | 6 |
| 80 | 14 |
| 81 | 13 |
| 82 | 10 |
| 83 | 23 |
| 84 | 8 |
| 85 | 5 |
| 86 | 4 |
| 87 | 5 |
| 88 | 2 |
| 89 | 63 |
| 90 | NA |
| 91 | 2700 |
| 92 | 14 |
| 93 | 45 |
| 94 | 7 |
| 95 | 591 |

NA = not available

Table 2 depicts enzyme inhibition data (K) for exemplary compounds.

| Example | Wee-1 binding ($K_i$ nM) | Example | Wee-1 binding ($K_i$ nM) | Example | Wee-1 binding ($K_i$ nM) |
|---|---|---|---|---|---|
| 96 | 2 | 98 | 2.4 | 100 | 4 |
| 97 | 6 | 99 | 3 | 101 | 7.6 |
| 102 | 210 | 103 | 110 | | |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound of formula (I):

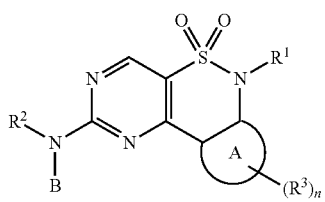

formula (I)

wherein
A is aryl or heteroaryl;
B is
(a) phenyl, wherein the phenyl is substituted with heterocycloalkyl and optionally one or two $R^4$, wherein $R^4$ is halo, $C_{1-6}$-alkyl, $C_{1-6}$ haloalkyl, or $OR^g$, wherein the heterocycloalkyl is optionally substituted with one, two, or three $R^{10}$; wherein $R^{10}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; or
(b) 5-16 membered monocyclic, bicyclic, or tricyclic heterocyclyl, wherein the heterocyclyl is optionally substituted with one or more $R^5$;
$R^1$ is H, $C_{1-8}$-alkyl, $C_{2-8}$-alkenyl, $C_{2-8}$-alkynyl, $C_{3-8}$-cycloalkyl, aryl, heteroaryl, aryl-$C_{1-6}$-alkyl-, $C_{3-8}$ cycloalkyl-$C_{1-6}$-alkyl-, or heteroaryl-$C_{1-6}$-alkyl-; wherein the $C_{1-8}$-alkyl, $C_{2-8}$-alkenyl, $C_{2-8}$-alkynyl, alone or as part of another moiety, are optionally substituted with one or more substituents selected from the group consisting of CN, $NO_2$, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$; and (b) the $C_{3-8}$-cycloalkyl, aryl, and heteroaryl, are optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$;
$R^2$ is H or $C_{1-6}$-alkyl;
$R^3$ is CN, $NO_2$, halo, $C_{1-6}$-alkyl, $C_{1-6}$-haloalkyl, $C_{1-6}$-hydroxyalkyl, $N(C_{1-6}$-alkyl$)_2$-$C_{1-6}$-alkyl, $C_{3-7}$ cycloalkyl, aryl, heteroaryl, heterocycloalkyl, —$OR^6$, —$C(O)R^6$, —$C(O)OR^6$, —$OC(O)R^6$, —$SR^6$, —$S(O)R^6$, —$SO_2R^6$, —$NR^7R^8$, —$NHC(O)R^6$, —$NHC(O)NHR^7$, —$NHC(O)OR^6$, —$NHSO_2R^6$, —$C(O)NHR^7$, or —$SO_2NHNR^7$, wherein the $R^3$ $C_{3-7}$ cycloalkyl, aryl, heteroaryl, heterocycloalkyl are optionally substituted with one or more $R^9$;
$R^4$ is CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, aryl-$C_{1-6}$-alkyl-, cycloalkyl-$C_{1-6}$-alkyl-, heteroaryl-$C_{1-6}$-alkyl-, or heterocycloalkyl-$C_{1-6}$-alkyl-; wherein the aryl, cycloalkyl, heteroaryl, or heterocycloalkyl, alone or as part of another moiety, are optionally substituted with one or more $R^{10}$;
$R^5$ is CN, $NO_2$, halo, $C_{1-6}$-alkyl, $C_{1-6}$-haloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$;
$R^6$ is hydrogen, $C_{1-6}$-alkyl, aryl, $C_{3-8}$ cycloalkyl, aryl, heteroaryl, or heterocycloalkyl, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl)$_2$;
$R^7$ is hydrogen, $C_{1-6}$-alkyl, aryl, $C_{3-8}$ cycloalkyl, aryl, heteroaryl, or heterocycloalkyl, wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, aryl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^8$ is hydrogen or $C_{1-6}$-alkyl;

$R^9$ is CN, $NO_2$, halo, $C_{1-6}$-alkyl, $C_{1-6}$-haloalkyl, $OR^m$, $SR^m$, $C(O)R^m$, $C(O)NR^nR^o$, $C(O)OR^m$, $NR^nR^o$, $NR^nC(O)R^m$, $S(O)_2R^m$, $NR^nS(O)_2R^m$, or $S(O)_2NR^nR^o$;

$R^{10}$ is CN, $NO_2$, halo, $C_{1-6}$-alkyl, $C_{1-6}$-haloalkyl, $OR^p$, $SR^p$, $C(O)R^p$, $C(O)NR^qR^r$, $C(O)OR^p$, $NR^qR^r$, $NR^qC(O)R^p$, $S(O)_2R^p$, $NR^qS(O)_2R^p$, or $S(O)_2NR^qR^r$;

$R^a$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^d$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^g$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^j$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^k$ and $R^l$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl$)_2$;

$R^m$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^n$ and $R^o$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^p$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^q$ and $R^r$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

n is 0, 1 or 2;

or a pharmaceutically acceptable salt or solvate thereof.

2. The compound of claim 1 of formula (I) wherein A is phenyl, pyridyl, or thiophenyl.

3. The compound of claim 1 of formula (I) wherein A is

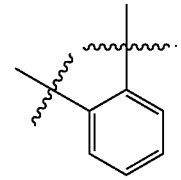

4. The compound of claim 1 of formula (I) wherein A is

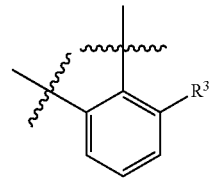 or 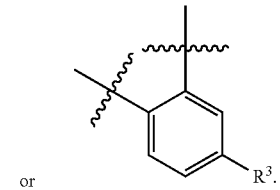

5. The compound of claim 1 of formula (I) wherein A is

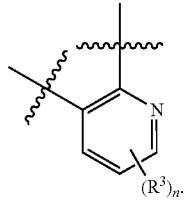

6. The compound of claim 1 of formula (I) wherein A is

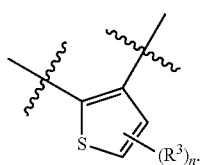

7. The compound of any one of claims 1, 2, 5, and 6 of formula (I) wherein n is 0.

8. The compound of any one of claims 1, 2, and 4-6 of formula (I) wherein $R^3$ is halo, —$OR^6$, —$C(O)OR^6$, —$C(O)NHR^7$, or —$NR^7R^8$.

9. The compound of any one of claims 1, 2, and 4-6 of formula (I) wherein $R^3$ is aryl or heteroaryl, wherein the aryl or heteroaryl is optionally substituted with one or more $R^9$, and $R^9$ is halo, $C_{1-6}$-alkyl, $C_{1-6}$-haloalkyl, $OR^m$, $C(O)R^m$, $C(O)NR''R^o$, $C(O)OR^m$, $NR''R^o$, or $NR''C(O)R^m$.

10. The compound of any one of claims 1-6 of formula (I) wherein $R^1$ is $C_{2-8}$ alkenyl.

11. The compound of any one of claims 1-6 of formula (I) wherein $R^1$ is $C_{1-8}$ alkyl.

12. The compound of any one of claims 1-6 of formula (I) wherein $R^1$ is aryl or aryl-$C_{1-6}$-alkyl, wherein the aryl, alone or a as part of another moiety, is optionally substituted with one or more substituents selected from the group consisting of $C_{1-6}$-alkyl, $C_{1-6}$-haloalkyl, and halogen.

13. The compound of any of claims 1-6 of formula (I), wherein B is phenyl.

14. The compound of any of claims 1-6, wherein B is

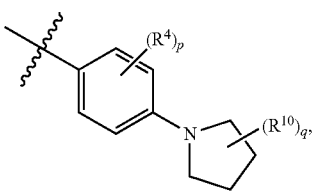

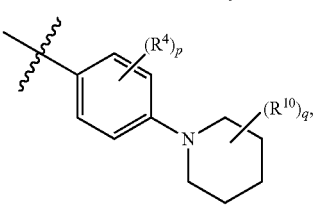

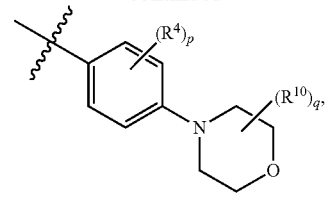

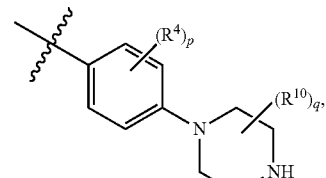

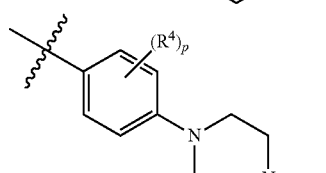

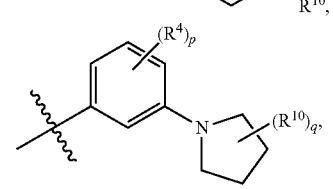

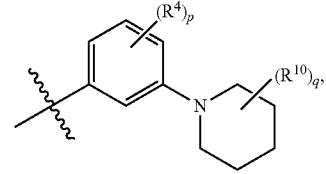

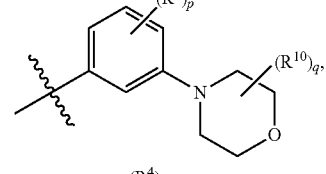

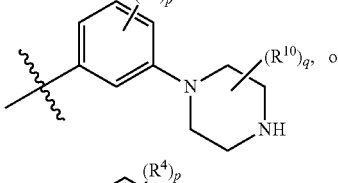

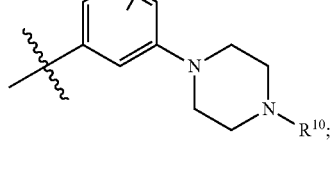

wherein $R^4$ is halo, $C_{1-6}$-alkyl, $C_{1-6}$ haloalkyl, or $OR^g$; p is 0 or 1; $R^{10}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and q is 0 or 1.

15. The compound of any of claims 1-6, wherein B is a monocyclic heterocyclyl, wherein the heterocyclyl is a 5-7 membered heteroaryl which is optionally substituted with one, two or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

16. The compound of any of claims 1-6, wherein B is a bicyclic heterocyclyl, wherein the heterocyclyl is a 7-11 membered bicyclic heterocyclyl which is optionally substituted with one, two or three $R^5$, and $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

17. The compound of any of claims 1-6, wherein B is a tricyclic heterocyclyl, wherein the heterocyclyl is a 10-15 membered tricyclic heterocyclyl which is optionally substituted with one, two or three $R^5$, and $R^5$ is $R^5$ is halo, $C_{1-6}$-alkyl, $C_{1-6}$-haloalkyl, $OR^j$, $C(O)R^j$, $C(O)OR^j$, $NR^kR^l$, or $S(O)_2R^j$.

18. The compound of claim 1 selected from the group consisting of

- 6-allyl-N-[4-(4-methylpiperazin-1-yl)phenyl]-6H-pyrimido[5,4-c][2,1]benzothiazin-2-amine 5,5-dioxide,
- N-[4-(4-methylpiperazin-1-yl)phenyl]-6-[(1E)-prop-1-en-1-yl]-6H-pyrimido[5,4-c][2,1]benzothiazin-2-amine 5,5-dioxide,
- 1-{6-[(6-allyl-5,5-dioxido-6H-pyrimido[5,4-c][2,1]benzothiazin-2-yl)amino]-2,3-dihydro-1H-indol-1-yl}ethanone,
- 6-[(6-allyl-5,5-dioxido-6H-pyrimido[5,4-c][2,1]benzothiazin-2-yl)amino]-2H-1,4-benzoxazin-3(4H)-one,
- 6-allyl-N-(1-methyl-1,2,3,4-tetrahydroquinolin-7-yl)-6H-pyrimido[5,4-c][2,1]benzothiazin-2-amine 5,5-dioxide,
- 6-allyl-N-[4-(4-methylpiperidin-1-yl)phenyl]-6H-pyrimido[5,4-c][2,1]benzothiazin-2-amine 5,5-dioxide,
- 1-(4-{4-[(6-allyl-5,5-dioxido-6H-pyrimido[5,4-c][2,1]benzothiazin-2-yl)amino]phenyl}piperazin-1-yl)ethanone,
- 6-allyl-N-[4-(piperidin-1-yl)phenyl]-6H-pyrimido[5,4-c][2,1]benzothiazin-2-amine 5,5-dioxide,
- 6-allyl-N-[2-(4-methylpiperazin-1-yl)phenyl]-6H-pyrimido[5,4-c][2,1]benzothiazin-2-amine 5,5-dioxide,
- 6-allyl-N-[4-(1H-imidazo[4,5-c]pyridin-2-yl)phenyl]-6H-pyrimido[5,4-c][2,1]benzothiazin-2-amine 5,5-dioxide,
- 6-allyl-N-[2-methoxy-4-(4-methylpiperazin-1-yl)phenyl]-6H-pyrimido[5,4-c][2,1]benzothiazin-2-amine 5,5-dioxide,
- 6-allyl-N-[4-(morpholin-4-yl)phenyl]-6H-pyrimido[5,4-c][2,1]benzothiazin-2-amine 5,5-dioxide,
- 6-allyl-N-[3-(4-methylpiperazin-1-yl)phenyl]-6H-pyrimido[5,4-c][2,1]benzothiazin-2-amine 5,5-dioxide,
- 6-allyl-N-[4-(1-methylpiperidin-4-yl)phenyl]-6H-pyrimido[5,4-c][2,1]benzothiazin-2-amine 5,5-dioxide,
- 6-allyl-N-[4-(1H-benzimidazol-2-yl)phenyl]-6H-pyrimido[5,4-c][2,1]benzothiazin-2-amine 5,5-dioxide,
- 6-allyl-N-[4-(1-methyl-1H-benzimidazol-2-yl)phenyl]-6H-pyrimido [5,4-c][2,1]benzothiazin-2-amine 5,5-dioxide,
- 6-allyl-N-(2,4,4-trimethyl-1,2,3,4-tetrahydroisoquinolin-7-yl)-6H-pyrimido[5,4-c][2,1]benzothiazin-2-amine 5,5-dioxide,
- 6-allyl-N-[4-(piperazin-1-yl)phenyl]-6H-pyrimido[5,4-c][2,1]benzothiazin-2-amine 5,5-dioxide,
- 6-allyl-N-(1,2,3,4-tetrahydroisoquinolin-7-yl)-6H-pyrimido[5,4-c][2,1]benzothiazin-2-amine 5,5-dioxide,
- 6-allyl-N-(pyridin-4-yl)-6H-pyrimido[5,4-c][2,1]benzothiazin-2-amine 5,5-dioxide,
- 6-allyl-N-(2'-methyl-2',3'-dihydro-1H-spiro[cyclopropane-1,4'-isoquinolin]-7'-yl)-6H-pyrimido [5,4-c][2,1]benzothiazin-2-amine 5,5-dioxide,
- 6-allyl-N-(1,2,3,4-tetrahydroquinolin-7-yl)-6H-pyrimido[5,4-c][2,1]benzothiazin-2-amine 5,5-dioxide,
- 6-allyl-N-[3-fluoro-4-(piperazin-1-yl)phenyl]-6H-pyrimido[5,4-c][2,1]benzothiazin-2-amine 5,5-dioxide,
- 6-allyl-N-(1,2,3,4-tetrahydroisoquinolin-7-yl)-6H-pyrido[2,3-c]pyrimido[4,5-e][1,2]thiazin-2-amine 5,5-dioxide,
- 6-allyl-N-[4-(piperazin-1-yl)phenyl]-6H-pyrido[2,3-c]pyrimido[4,5-e][1,2]thiazin-2-amine 5,5-dioxide,
- 1-{6-[(6-allyl-5,5-dioxido-6H-pyrido[2,3-c]pyrimido[4,5-e][1,2]thiazin-2-yl)amino]-2,3-dihydro-1H-indol-1-yl}ethanone,
- 6-allyl-N-[3-fluoro-4-(piperazin-1-yl)phenyl]-6H-pyrido[2,3-c]pyrimido[4,5-e][1,2]thiazin-2-amine 5,5-dioxide,
- 6-allyl-N-[4-(piperidin-4-yl)phenyl]-6H-pyrido[2,3-c]pyrimido[4,5-e][1,2]thiazin-2-amine 5,5-dioxide,
- 6-allyl-N-(1,2,3,4-tetrahydroquinolin-7-yl)-6H-pyrido[2,3-c]pyrimido[4,5-e][1,2]thiazin-2-amine 5,5-dioxide,
- 6-allyl-N-[4-(4-methylpiperazin-1-yl)phenyl]-6H-pyrido[2,3-c]pyrimido[4,5-e][1,2]thiazin-2-amine 5,5-dioxide,
- 6-allyl-N-[3-chloro-4-(4-methylpiperazin-1-yl)phenyl]-6H-pyrido[2,3-c]pyrimido[4,5-e][1,2]thiazin-2-amine 5,5-dioxide,
- 6-allyl-N-[3-methyl-4-(piperazin-1-yl)phenyl]-6H-pyrido[2,3-c]pyrimido[4,5-e][1,2]thiazin-2-amine 5,5-dioxide,
- {4-[(6-allyl-5,5-dioxido-6H-pyrido[2,3-c]pyrimido[4,5-e][1,2]thiazin-2-yl)amino]phenyl}(4-methylpiperazin-1-yl)methanone,
- 6-allyl-N-[2-methyl-4-(4-methylpiperazin-1-yl)phenyl]-6H-pyrido[2,3-c]pyrimido[4,5-e][1,2]thiazin-2-amine 5,5-dioxide,
- 6-allyl-N-[4-(pyrrolidin-3-yl)phenyl]-6H-pyrido[2,3-c]pyrimido[4,5-e][1,2]thiazin-2-amine 5,5-dioxide,
- 6-allyl-N-(1,2,3,4-tetrahydroisoquinolin-6-yl)-6H-pyrido[2,3-c]pyrimido[4,5-e][1,2]thiazin-2-amine 5,5-dioxide,
- 6-allyl-N-(2'-methyl-2',3'-dihydro-1H-spiro[cyclopropane-1,4'-isoquinolin]-7'-yl)-6H-pyrido [2,3-c]pyrimido[4,5-e][1,2]thiazin-2-amine 5,5-dioxide,
- 6-allyl-N-[4-(hexahydropyrrolo[1,2-a]pyrazin-2(1H)-yl)phenyl]-6H-pyrido[2,3-c]pyrimido[4,5-e][1,2]thiazin-2-amine 5,5-dioxide,
- 6-allyl-N-(1-methyl-1,2,3,4-tetrahydroquinolin-7-yl)-6H-pyrido[2,3-c]pyrimido[4,5-e][1,2]thiazin-2-amine 5,5-dioxide,
- 6-allyl-N-[3-methyl-4-(4-methylpiperazin-1-yl)phenyl]-6H-pyrido[2,3-c]pyrimido[4,5-e][1,2]thiazin-2-amine 5,5-dioxide,
- 6-allyl-N-[4-(piperazin-1-yl)-3-(trifluoromethyl)phenyl]-6H-pyrido[2,3-c]pyrimido[4,5-e][1,2]thiazin-2-amine 5,5-dioxide,
- 6-allyl-N-[4-(morpholin-4-yl)phenyl]-6H-pyrido[2,3-c]pyrimido[4,5-e][1,2]thiazin-2-amine 5,5-dioxide,
- 6-allyl-N-[3-methyl-4-(4-methyl-1,4-diazepan-1-yl)phenyl]-6H-pyrido[2,3-c]pyrimido[4,5-e][1,2]thiazin-2-amine 5,5-dioxide,
- 6-allyl-N-(2',3'-dihydro-1H-spiro[cyclopropane-1,4'-isoquinolin]-7'-yl)-6H-pyrido[2,3-c]pyrimido[4,5-e][1,2]thiazin-2-amine 5,5-dioxide,
- 6-methyl-N-[4-(4-methylpiperazin-1-yl)phenyl]-6H-pyrimido[4,5-e]thieno[3,2-c][1,2]thiazin-2-amine 5,5-dioxide,
- 6-methyl-N-[4-(4-methylpiperazin-1-yl)phenyl]-6H-pyrimido[5,4-c][2,1]benzothiazin-2-amine 5,5-dioxide,
- 6-methyl-N-[4-(morpholin-4-yl)phenyl]-6H-pyrimido[5,4-c][2,1]benzothiazin-2-amine 5,5-dioxide, 6-allyl-2-{[4-(4-methylpiperazin-1-yl)phenyl]amino}-6H-pyrimido [5,4-c][2,1]benzothiazine-7-carboxylic acid 5,5-dioxide, methyl 6-allyl-2-{[4-(4-methylpiperazin-1-yl)phenyl]amino}-6H-pyrimido [5,4-c][2,1]benzothiazine-7-carboxylate 5,5-dioxide, 6-allyl-N-methyl-2-{[4-(4-methylpiperazin-1-yl)phenyl]amino}-6H-pyrimido[5,4-c][2,1]benzothiazine-7-carboxamide 5,5-dioxide, 6-allyl-N-(2-hydroxyethyl)-2-{[4-(4-methylpiperazin-1-yl)phenyl]amino}-6H-pyrimido [5,4-c][2,1]benzothiazine-7-carboxamide 5,5-dioxide, 6-allyl-8-bromo-N-[4-(4-methylpiperazin-1-yl)phenyl]-6H-pyrimido[5,4-c][2,1]benzothiazin-2-amine 5,5-dioxide, methyl 2-{[4-(4-methylpiperazin-1-yl)phenyl]amino}-6H-pyrimido [5,4-c][2,1]benzothiazine-8-carboxylate 5,5-dioxide, 8-bromo-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-8-phenyl-6-propyl-6H-pyrimido[5,4-c][2,1]benzothiazin-2-amine 5,5-dioxide, N-[4-(4-methylpiperazin-1-yl)phenyl]-6-propyl-8-(pyridin-3-yl)-6H-pyrimido[5,4-c][2,1]benzothiazin-2-amine 5,5-dioxide, N-[4-(4-methylpiperazin-1-yl)phenyl]-6-propyl-8-(1H-pyrazol-4-yl)-6H-pyrimido[5,4-c][2,1]benzothiazin-2-amine 5,5-dioxide, 4-(2-{[4-(4-methylpiperazin-1-yl)phenyl]amino}-5,5-dioxido-6-propyl-6H-pyrimido[5,4-c][2,1]benzothiazin-8-yl)benzamide, N-cyclopropyl-4-(2-{[4-(4-methylpiperazin-1-yl)phenyl]amino}-5,5-dioxido-6-propyl-6H-pyrimido[5,4-c][2,1]benzothiazin-8-yl)benzamide, 8-(2-aminopyrimidin-5-yl)-N-[4-(4-methylpiperazin-1-yl)phenyl]-6-propyl-6H-pyrimido [5,4-c][2,1]benzothiazin-2-amine 5,5-dioxide, N-[4-(4-methylpiperazin-1-yl)phenyl]-6-propyl-8-(3-thienyl)-6H-pyrimido[5,4-c][2,1]benzothiazin-2-amine 5,5-dioxide, 4-(2-{[4-(4-methylpiperazin-1-yl)phenyl]amino}-5,5-dioxido-6-propyl-6H-pyrimido[5,4-c][2,1]benzothiazin-8-yl)phenol, N-[4-(4-methylpiperazin-1-yl)phenyl]-6-propyl-8-(pyridin-4-yl)-6H-pyrimido[5,4-c][2,1]benzothiazin-2-amine 5,5-dioxide, N-[4-(4-methylpiperazin-1-yl)phenyl]-6-propyl-8-(1H-pyrrolo[2,3-b]pyridin-3-yl)-6H-pyrimido [5,4-c][2,1]benzothiazin-2-amine 5,5-dioxide, methyl 2-{[4-(4-methylpiperazin-1-yl)phenyl]amino}-6-propyl-6H-pyrimido [5,4-c][2,1]benzothiazine-8-carboxylate 5,5-dioxide, 2-{[4-(4-methylpiperazin-1-yl)phenyl]amino}-6-propyl-6H-pyrimido [5,4-c][2,1]benzothiazine-8-carboxamide 5,5-dioxide, 2-(2-{[4-(4-methylpiperazin-1-yl)phenyl]amino}-5,5-dioxido-6-propyl-6H-pyrimido [5,4-c][2,1]benzothiazin-8-yl)propan-2-ol, N-cyclohexyl-2-{[4-(4-methylpiperazin-1-yl)phenyl]amino}-6-propyl-6H-pyrimido [5,4-c][2,1]benzothiazine-8-carboxamide 5,5-dioxide, N-methyl-2-{[4-(4-methylpiperazin-1-yl)phenyl]amino}-6-propyl-6H-pyrimido [5,4-c][2,1]benzothiazine-8-carboxamide 5,5-dioxide, N,N-dimethyl-2-{[4-(4-methylpiperazin-1-yl)phenyl]amino}-6-propyl-6H-pyrimido [5,4-c][2,1]benzothiazine-8-carboxamide 5,5-dioxide, N-(2-hydroxyethyl)-2-{[4-(4-methylpiperazin-1-yl)phenyl]amino }-6-propyl-6H-pyrimido [5,4-c][2,1]benzothiazine-8-carboxamide 5,5-dioxide, N-(2-methoxyethyl)-2-{[4-(4-methylpiperazin-1-yl)phenyl]amino }-6-propyl-6H-pyrimido [5,4-c][2,1]benzothiazine-8-carboxamide 5,5-dioxide, N-(trans-4-aminocyclohexyl)-2-{[4-(4-methylpiperazin-1-yl)phenyl]amino }-6-propyl-6H-pyrimido[5,4-c][2,1]benzothiazine-8-carboxamide 5,5-dioxide, 2-{[4-(4-methylpiperazin-1-yl)phenyl]amino}-6-propyl-N-(pyridin-3-ylmethyl)-6H-pyrimido [5,4-c][2,1]benzothiazine-8-carboxamide 5,5-dioxide, methyl 2-{[4-(4-methylpiperazin-1-yl)phenyl]amino}-6-phenyl-6H-pyrimido[5,4-c][2,1]benzothiazine-8-carboxylate 5,5-dioxide, methyl 6-(3-methylphenyl)-2-{[4-(4-methylpiperazin-1-yl)phenyl]amino}-6H-pyrimido [5,4-c][2,1]benzothiazine-8-carboxylate 5,5-dioxide, methyl 6-(3,5-dichlorophenyl)-2-{[4-(4-methylpiperazin-1-yl)phenyl]amino}-6H-pyrimido [5,4-c][2,1]benzothiazine-8-carboxylate 5,5-dioxide, methyl 6-[3,5-bis(trifluoromethyl)phenyl]-2-{[4-(4-methylpiperazin-1-yl)phenyl]amino}-6H-pyrimido[5,4-c][2,1]benzothiazine-8-carboxylate 5,5-dioxide, 8-(1H-imidazol-1-yl)-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-6-propyl-8-(1H-pyrrol-1-yl)-6H-pyrimido[5,4-c][2,1]benzothiazin-2-amine 5,5-dioxide, N-[4-(4-methylpiperazin-1-yl)phenyl]-6-propyl-8-(1H-1,2,4-triazol-1-yl)-6H-pyrimido [5,4-c][2,1]benzothiazin-2-amine 5,5-dioxide, methyl 6-(2,6-dichlorobenzyl)-2-{[4-(4-methylpiperazin-1-yl)phenyl]amino}-6H-pyrimido [5,4-c][2,1]benzothiazine-8-carboxylate 5,5-dioxide, 9-bromo-N-[4-(4-methylpiperazin-1-yl)phenyl]-6-propyl-6H-pyrimido[5,4-c][2,1]benzothiazin-2-amine 5,5-dioxide, N-[4-(4-methylpiperazin-1-yl)phenyl]-9-phenyl-6-propyl-6H-pyrimido[5,4-c][2,1]benzothiazin-2-amine 5,5-dioxide, N-[4-(4-methylpiperazin-1-yl)phenyl]-6-propyl-9-(pyridin-3-yl)-6H-pyrimido[5,4-c][2,1]benzothiazin-2-amine 5,5-dioxide, N-[4-(4-methylpiperazin-1-yl)phenyl]-6-propyl-9-(pyridin-4-yl)-6H-pyrimido[5,4-c][2,1]benzothiazin-2-amine 5,5-dioxide, N-methyl-3-(2-{[4-(4-methylpiperazin-1-yl)phenyl]amino}-5,5-dioxido-6-propyl-6H-pyrimido [5,4-c][2,1]benzothiazin-9-yl)benzamide, 9-{2-[(dimethylamino)methyl]phenyl}-N-[4-(4-methylpiperazin-1-yl)phenyl]-6-propyl-6H-pyrimido[5,4-c][2,1]benzothiazin-2-amine 5,5-dioxide, N-[5-(4-methylpiperazin-1-yl)pyridin-2-yl]-6-(prop-2-en-1-yl)-6H-pyrido[2,3-c]pyrimido[4,5-e][1,2]thiazin-2-amine 5,5-dioxide, and N-[5-(piperazin-1-yl)pyridin-2-yl]-6-(prop-2-en-1-yl)-6H-pyrido[2,3-c]pyrimido[4,5-e][1,2]thiazin-2-amine 5,5-dioxide.

19. A pharmaceutical composition comprising a compound or pharmaceutically acceptable salt of any of claim 1-6, or 18 and a pharmaceutically acceptable excipient.

* * * * *

UNITED STATES PATENT AND TRADEMARK OFFICE
CERTIFICATE OF CORRECTION

PATENT NO. : 8,716,297 B2
APPLICATION NO. : 13/547314
DATED : May 6, 2014
INVENTOR(S) : Woods et al.

It is certified that error appears in the above-identified patent and that said Letters Patent is hereby corrected as shown below:

In the Claims

Column 88, line 59, claim 14: "$C_{i\text{-}6}$" to read as --$C_{1\text{-}6}$--

Column 89, line 61, claim 18: "1H" to read as --1′H--

Column 90, line 37, claim 18: "1H" to read as --1′H--

Column 90, line 58, claim 18: "1H" to read as --1′H--

Signed and Sealed this
Seventeenth Day of February, 2015

Michelle K. Lee
*Deputy Director of the United States Patent and Trademark Office*